United States Patent
Knight et al.

(10) Patent No.: US 10,287,343 B2
(45) Date of Patent: May 14, 2019

(54) TAU-BINDING ANTIBODIES

(71) Applicant: UCB BIOPHARMA SPRL, Brussels (BE)

(72) Inventors: David Edward Ormonde Knight, Slough (GB); Terence Seward Baker, Slough (GB); David James McMillan, Slough (GB); Robert Anthony Griffin, Slough (GB); Georges Mairet-Coello, Brussels (BE); Patrick Downey, Brussels (BE); Jean-Philippe Courade, Brussels (BE)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/742,087

(22) PCT Filed: Jul. 5, 2016

(86) PCT No.: PCT/EP2016/065813
§ 371 (c)(1),
(2) Date: Jan. 5, 2018

(87) PCT Pub. No.: WO2017/005734
PCT Pub. Date: Jan. 12, 2017

(65) Prior Publication Data
US 2018/0201666 A1    Jul. 19, 2018

(30) Foreign Application Priority Data
Jul. 6, 2015  (EP) .................................. 15175522

(51) Int. Cl.
*C07K 16/18* (2006.01)
*A61K 39/00* (2006.01)
*C07K 14/47* (2006.01)
*A61P 25/28* (2006.01)

(52) U.S. Cl.
CPC .............. *C07K 16/18* (2013.01); *A61P 25/28* (2018.01); *C07K 14/4711* (2013.01); *C07K 2317/24* (2013.01); *C07K 2317/34* (2013.01); *C07K 2317/524* (2013.01); *C07K 2317/526* (2013.01); *C07K 2317/55* (2013.01); *C07K 2317/56* (2013.01); *C07K 2317/565* (2013.01); *C07K 2317/70* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,816,397 A | 3/1989 | Boss et al. |
| 4,816,567 A | 3/1989 | Cabilly et al. |
| 5,225,539 A | 7/1993 | Winter |
| 2017/0355756 A1* | 12/2017 | Julien ................... C07K 16/18 |
| 2018/0194832 A1 | 7/2018 | Tyson et al. |

FOREIGN PATENT DOCUMENTS

| EP | 0125023 | 6/1991 |
| EP | 0519596 | 12/1992 |
| EP | 0120694 | 7/1993 |
| EP | 0194276 | 8/1993 |
| EP | 0239400 | 8/1994 |
| WO | WO 86/01533 | 3/1986 |
| WO | WO 91/09967 | 7/1991 |
| WO | WO 92/22583 | 12/1992 |
| WO | WO 2005/003169 | 1/2005 |
| WO | WO 2005/003170 | 1/2005 |
| WO | WO 2005/003171 | 1/2005 |
| WO | WO 2005/113605 | 12/2005 |
| WO | WO 2007/024715 | 3/2007 |
| WO | WO 2008/012543 | 1/2008 |
| WO | WO2008068048 | * 6/2008 |
| WO | WO 2009/040562 | 4/2009 |
| WO | WO 2010/035012 | 4/2010 |
| WO | WO 2010/142423 | 12/2010 |
| WO | WO 2011/030107 | 3/2011 |
| WO | WO 2013/068571 | 5/2013 |
| WO | WO 2013/096380 | 6/2013 |
| WO | WO 2014/008404 | 1/2014 |
| WO | WO 2014/028777 | 2/2014 |
| WO | WO 2017/005732 | 1/2017 |

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" embo 14(12):2784-2794 (Year: 1995).*
Braak, H. et al. "Staging of Alzheimer's Disease-Related Neurofibrillary Changes" *Neurobiology of Aging*, May 1, 1995, pp. 271-278, vol. 16, No. 3.
Buée, L. et al. "Tau protein isoforms, phosphorylation and role in neurodegenerative disorders" *Brain Research Reviews*, Aug. 1, 2000, pp. 95-130, vol. 33, No. 1.
Clavaguera, F. et al, ""Prion-Like" Templated Misfolding in Tauopathies" *Brain Pathology*, Apr. 16, 2013, pp. 342-349, vol. 23, No. 3.
Maccioni, R. B. et al. "Anomalously phosphorylated tau and Aβ fragments in the CSF correlates with cognitive impairment in MCI subjects" *Neurobiology of Aging*, Feb. 1, 2006, pp. 237-244, vol. 27, No. 2.
Mercken, M. et al. "Monoclonal antibodies with selective specificity for Alzheimer Tau are directed against phosphatase-sensitive epitopes" *Acta Neuropathologica*, Jan. 1, 1992, pp. 265-272, vol. 84, No. 3.

(Continued)

*Primary Examiner* — Adam Weidner
(74) *Attorney, Agent, or Firm* — Saliwanchik, Lloyd & Eisenschenk

(57) ABSTRACT

The present invention relates to Tau-binding antibodies and binding fragments thereof.

32 Claims, 23 Drawing Sheets

Specification includes a Sequence Listing.

(56) References Cited

OTHER PUBLICATIONS

Yanamandra, K. et al. "Anti-tau antibody reduces insoluble tau and decreases brain atrophy" *Annals of Clinical and Translational Neurology*, Jan. 23, 2015, pp. 278-288, vol. 2, No. 3.

Written Opinion in International Application No. PCT/EP2016/065813, dated Sep. 12, 2016, pp. 1-10.

Allowed claims of U.S. Appl. No. 15/742,070, 2018, pp. 1-6.

Adair, J.R. et al. "Therapeutic Antibodies" *Drug Design Reviews*, 2005, pp. 1-11, vol. 2, No. 3.

Angal, S. et al. "A Single Amino Acid Substitution Abolishes the Heterogeneity of Chimeric Mouse/Human (IgG4) Antibody" *Molecular Immunology*, 1993, pp. 105-108, vol. 30, No. 1.

Garber, E. et al. "A broad range of Fab stabilities within a host of therapeutic IgGs" *Biochemical and Biophysical Research Communications*, 2007, pp. 751-757, vol. 355.

Holliger, P. et al. "Engineered antibody fragments and the rise of single domains" *Nature Biotechnology*, Sep. 2005, pp. 1126-1136, vol. 23, No. 9.

Riechmann, L. et al. "Reshaping human antibodies for therapy" *Nature*, Mar. 24, 1988, pp. 323-327, vol. 332.

Verma, R. et al. "Antibody engineering: Comparison of bacterial, yeast, insect and mammalian expression systems" *Journal of Immunological Methods*, 1998, pp. 165-181, vol. 216.

\* cited by examiner

Figure 1

VL_AB1

DIVMTQTPVSLSVTLGDQASISCRSSQSLEYSDGYTYLEWYLQKPGQSPQLLIYEVS
NRFSGVPDRFIGSGSGTDFTLKISRVEPEDLGVYYCFQATHNPYTFGAGTKLEIK

IGKV2_29

DIVMTQTPLSLSVTPGQPASISCKSSQSLLHSDGKTYLYWYLQKPGQSPQLLIYEVS
SRFSGVPDRFSGSGSGTDFTLKISRVEAEDVGVYYCMQGIHLPYTFGQGTKLEIK gVL3_AB1

DIVMTQTPLSLSVTPGQPASISCRSSQSLEYSDGYTYLEWYLQKPGQSPQLLIYEVS
NRFSGVPDRFSGSGSGTDFTLKISRVEAEDVGVYYCFQATHNPYTFGQGTKLEIK

Figure 2

VH_AB1

EVKLEESGPGLMQPSETLSLTCTVSGFSLTSNDIAWVRQPLGKGLVWMGTIWTDGSTNYN
SAVQSRLSISRDTSKSQFFLKMNSLQPEDTGTYYCARHRLYYGAFDYWGQGTMVTVSS

IGHV4-59

QVQLQESGPGLVKPSETLSLTCTVSGGSISSYYWSWIRQPPGKGLEWIGYIYYSGSTNYN
PSLKSRVTISVDTSKNQFSLKLSSVTAADTAVYYCAR-----DAFDWGQGTMVTVSS gVH17_AB1

EVQLQESGPGLVKPSETLSLTCTVSGFSLTSNDIAWIRQPPGKGLEWMGTIWTDGSTNYN
AAVQSRVTISVDTSKNQFSLKLSSVTAADTAVYYCARHRLYYGAFDYWGQGTMVTVSS gVH18_AB1

EVQLQESGPGLVKPSETLSLTCTVSGFSLTSNDIAWIRQPPGKGLEWMGTIWTDGSTNYN
TAVQSRVTISVDTSKNQFSLKLSSVTAADTAVYYCARHRLYYGAFDYWGQGTMVTVSS

Figure 4
A
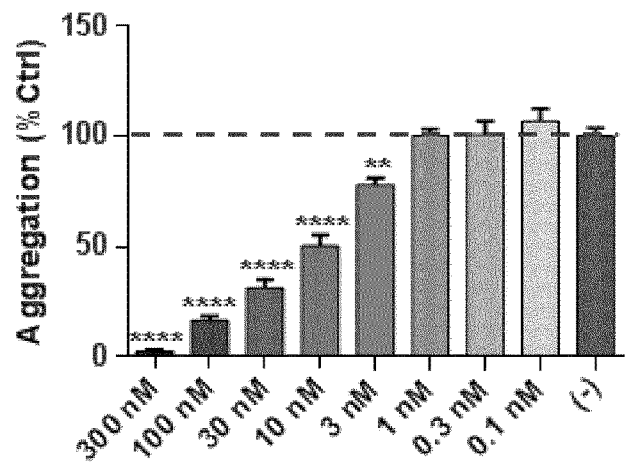
B
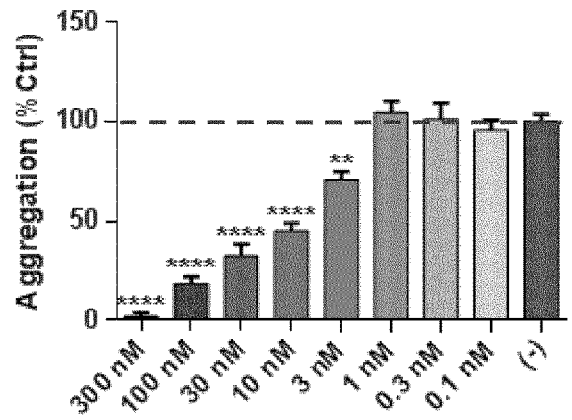
C
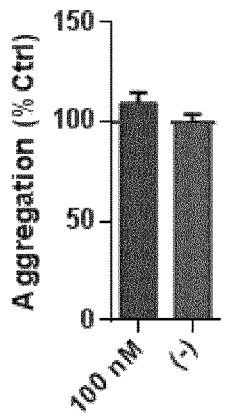

A)

Figure 5:
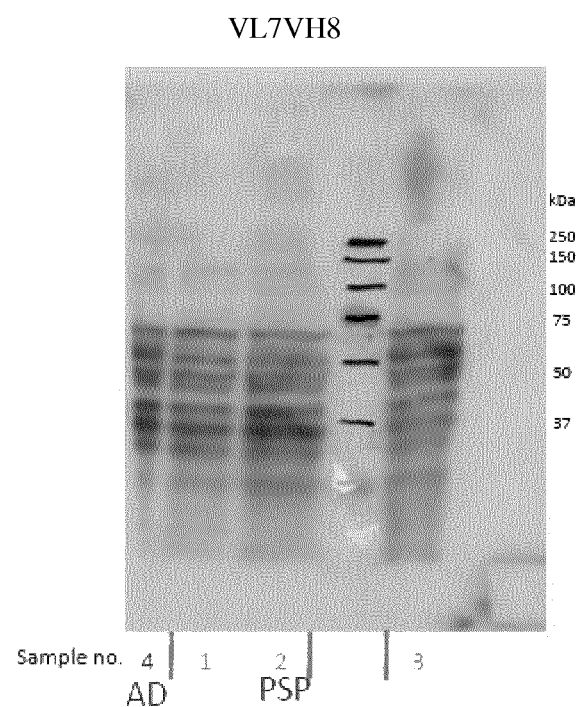

Figure 5 (continued)
B)
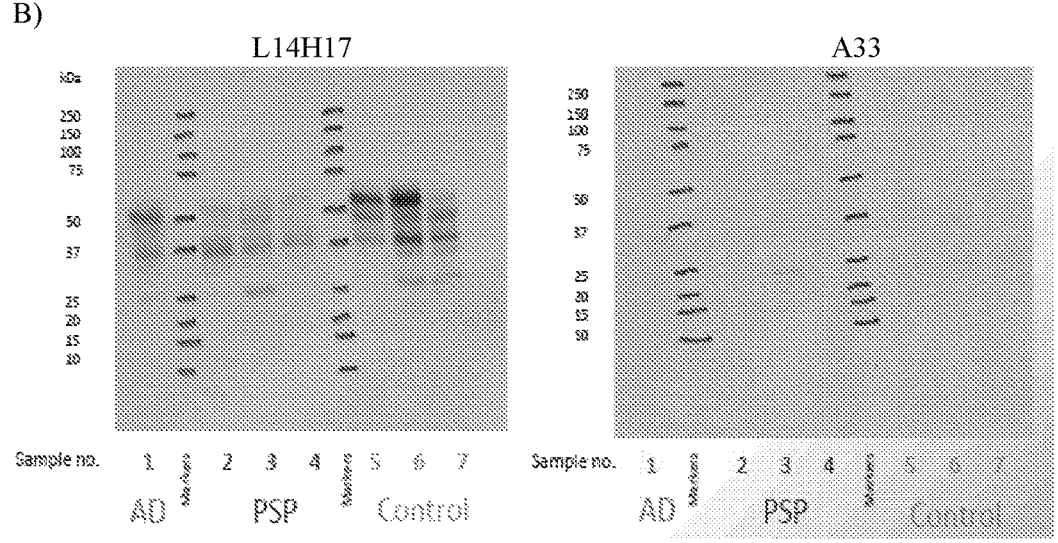
C)
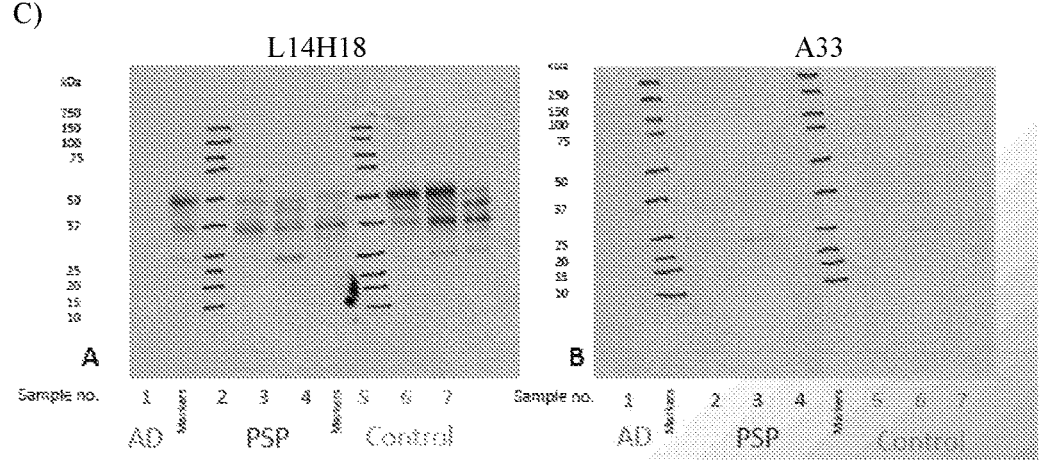

Figure 7

DNA contruct encoding human Tau isoform 2 for E. coli expression (pET 6His TEV-hTau iso 2 (1-441)) (SEQ ID No.:39)

```
TGGCGAATGGGACGCGCCCTGTAGCGGCGCATTAAGCGCGGCGGGTGTGGTGGTTACGCGCAGCGTGA
CCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCA
CCTCGACCCCAAAAAACTTGATTAGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACTGGAACAACACTC
AACCCTATCTCGGTCTATTCTTTTGATTTATAAGGGATTTTGCCGATTTCGGCCTATTGGTTAAAAAA
TGAGCTGATTTAACAAAAATTTAACGCGAATTTTAACAAAATATTAACGTTTACAATTTCAGGTGGCA
CTTTTCGGGGAAATGTGCGCGGAACCCCTATTTGTTTATTTTTCTAAATACATTCAAATATGTATCCG
CTCATGAGACAATAACCCTGATAAATGCTTCAATAATATTGAAAAAGGAAGAGTATGAGTATTCAACA
TTTCCGTGTCGCCCTTATTCCCTTTTTTGCGGCATTTTGCCTTCCTGTTTTTGCTCACCCAGAAACGC
TGGTGAAAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCCGCATACACTATT
CTCAGAATGACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACAACGATCGG
AGGACCGAAGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGCAGCAATGGCAACA
ACGTTGCGCAAACTATTAACTGGCGAACTACTTACTCTAGCTTCCCGGCAACAATTAATAGACTGGAT
GGAGGCGGATAAAGTTGCAGGACCACTTCTGCGCTCGGCCCTTCCGGCTGGCTGGTTTATTGCTGATA
AATCTGGAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACTTTAGATTG
ATTTAAAACTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGATCTTCTTG
AGATCCTTTTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGCAGATACCA
AATACTGTCCTTCTAGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTGTCTTACCGGGTTGG
ACTCAAGACGATAGTTACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTATGAGAAAGCGCCACGCT
TCCCGAAGGGAGAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCTGACTTGAGCGT
CGATTTTTGTGATGCTCGTCAGGGGGGCGGAGCCTATGGAAAAACGCCAGCAACGCGGCCTTTTTACG
GTTCCTGGCCTTTTGCTGGCCTTTTGCTCACATGTTCTTTCCTGCGTTATCCCCTGATTCTGTGGATA
ACCGTATTACCGCCTTTGAGTGAGCTGATACCGCTCGCCGCAGCCGAACGACCGAGCGCAGCGAGTCA
GTGAGCGAGGAAGCGGAAGAGCGCCTGATGCGGTATTTTCTCCTTACGCATCTGTGCGGTATTTCACA
CCGCATATATGGTGCACTCTCAGTACAATCTGCTCTGATGCCGCATAGTTAAGCCAGTATACACTCCG
CTATCGCTACGTGACTGGGTCATGGCTGCGCCCCGACACCCGCCAACACCCGCTGACGCGCCCTGACG
GGCTTGTCTGCTCCCGGCATCCGCTTACAGACAAGCTGTGACCGTCTCCGGGAGCTGCATGTGTCAGA
GGTTTTCACCGTCATCACCGAAACGCGCGAGGCAGCTGCGGTAAAGCTCATCAGCGTGGTCGTGAAGC
GATTCACAGATGTCTGCCTGTTCATCCGCGTCCAGCTCGTTGAGTTTCTCCAGAAGCGTTAATGTCTG
GCTTCTGATAAAGCGGGCCATGTTAAGGGCGGTTTTTTCCTGTTTGGTCACTGATGCCTCCGTGTAAG
GGGGATTTCTGTTCATGGGGGTAATGATACCGATGAAACGAGAGAGGATGCTCACGATACGGGTTACT
GATGATGAACATGCCCGGTTACTGGAACGTTGTGAGGGTAAACAACTGGCGGTATGGATGCGGCGGGA
CCAGAGAAAAATCACTCAGGGTCAATGCCAGCGCTTCGTTAATACAGATGTAGGTGTTCCACAGGGTA
GCCAGCAGCATCCTGCGATGCAGATCCGGAACATAATGGTGCAGGGCGCTGACTTCCGCGTTTCCAGA
CTTTACGAAACACGGAAACCGAAGACCATTCATGTTGTTGCTCAGGTCGCAGACGTTTTGCAGCAGCA
GTCGCTTCACGTTCGCTCGCGTATCGGTGATTCATTCTGCTAACCAGTAAGGCAACCCCGCCAGCCTA
GCCGGGTCCTCAACGACAGGAGCACGATCATGCGCACCCGTGGGGCCGCCATGCCGGCGATAATGGCC
TGCTTCTCGCCGAAACGTTTGGTGGCGGGACCAGTGACGAAGGCTTGAGCGAGGGCGTGCAAGATTCC
```

Figure 7 (continued)

```
GAATACCGCAAGCGACAGGCCGATCATCGTCGCGCTCCAGCGAAAGCGGTCCTCGCCGAAAATGACCC
AGAGCGCTGCCGGCACCTGTCCTACGAGTTGCATGATAAAGAAGACAGTCATAAGTGCGGCGACGATA
GTCATGCCCCGCGCCCACCGGAAGGAGCTGACTGGGTTGAAGGCTCTCAAGGGCATCGGTCGAGATCC
CGGTGCCTAATGAGTGAGCTAACTTACATTAATTGCGTTGCGCTCACTGCCCGCTTTCCAGTCGGGAA
ACCTGTCGTGCCAGCTGCATTAATGAATCGGCCAACGCGCGGGGAGAGGCGGTTTGCGTATTGGGCGC
CAGGGTGGTTTTTCTTTTCACCAGTGAGACGGGCAACAGCTGATTGCCCTTCACCGCCTGGCCCTGAG
AGAGTTGCAGCAAGCGGTCCACGCTGGTTTGCCCCAGCAGGCGAAAATCCTGTTTGATGGTGGTTAAC
GGCGGGATATAACATGAGCTGTCTTCGGTATCGTCGTATCCCACTACCGAGATGTCCGCACCAACGCG
CAGCCCGGACTCGGTAATGGCGCGCATTGCGCCCAGCGCCATCTGATCGTTGGCAACCAGCATCGCAG
TGGGAACGATGCCCTCATTCAGCATTTGCATGGTTTGTTGAAAACCGGACATGGCACTCCAGTCGCCT
TCCCGTTCCGCTATCGGCTGAATTTGATTGCGAGTGAGATATTTATGCCAGCCAGCCAGACGCAGACG
CGCCGAGACAGAACTTAATGGGCCCGCTAACAGCGCGATTTGCTGGTGACCCAATGCGACCAGATGCT
CCACGCCCAGTCGCGTACCGTCTTCATGGGAGAAAATAATACTGTTGATGGGTGTCTGGTCAGAGACA
TCAAGAAATAACGCCGGAACATTAGTGCAGGCAGCTTCCACAGCAATGGCATCCTGGTCATCCAGCGG
ATAGTTAATGATCAGCCCACTGACGCGTTGCGCGAGAAGATTGTGCACCGCCGCTTTACAGGCTTCGA
CGCCGCTTCGTTCTACCATCGACACCACCACGCTGGCACCCAGTTGATCGGCGCGAGATTTAATCGCC
GCGACAATTTGCGACGGCGCGTGCAGGGCCAGACTGGAGGTGGCAACGCCAATCAGCAACGACTGTTT
GCCCGCCAGTTGTTGTGCCACGCGGTTGGGAATGTAATTCAGCTCCGCCATCGCCGCTTCCACTTTTT
CCCGCGTTTTCGCAGAAACGTGGCTGGCCTGGTTCACCACGCGGGAAACGGTCTGATAAGAGACACCG
GCATACTCTGCGACATCGTATAACGTTACTGGTTTCACATTCACCACCCTGAATTGACTCTCTTCGG
GCGCTATCATGCCATACCGCGAAAGGTTTTGCGCCATTCGATGGTGTCCGGGATCTCGACGCTCTCCC
TTATGCGACTCCTGCATTAGGAAGCAGCCCAGTAGTAGGTTGAGGCCGTTGAGCACCGCCGCCGCAAG
GAATGGTGCATGCAAGGAGATGGCGCCCAACAGTCCCCGGCCACGGGGCCTGCCACCATACCCACGC
CGAAACAAGCGCTCATGAGCCCGAAGTGGCGAGCCCGATCTTCCCCATCGGTGATGTCGGCGATATAG
GCGCCAGCAACCGCACCTGTGGCGCCGGTGATGCCGGCCACGATGCGTCCGGCGTAGAGGATCGAGAT
CGATCTCGATCCCGCGAAATTAATACGACTCACTATAGGGGAATTGTGAGCGGATAACAATTCCCCTC
TAGAAATAATTTTGTTTAACTTTAAGAAGGAGATATACAT
```
***ATGGGCTCAAGCCACCACCACCACCACC
ACAGCAGCGGCGAGAACTTGTACTTTCAAGGATCCGCAGAACCACGTCAAGAATTTGAGGTTATGGAA
GATCACGCGGGCACTTACGGTTTGGGTGATCGTAAAGACCAGGGCGGCTATACCATGCATCAAGATCA
AGAGGGCGACACCGATGCTGGCTTGAAAGAGTCGCCGCTGCAGACTCCGACCGAGGATGGCAGCGAAG
AGCCGGGCAGCGAGACTAGCGATGCGAAGTCGACCCCGACCGCCGAGGACGTTACCGCACCGCTGGTC
GACGAGGGTGCTCCGGGTAAACAGGCGGCTGCACAGCCGCACACGGAGATTCCGGAAGGCACCACCGC
AGAAGAGGCGGGTATCGGCGACACTCCGTCCCTGGAAGATGAGGCAGCCGGTCATGTCACGCAGGCGC
GTATGGTGAGCAAGAGCAAAGATGGTACGGGTAGCGACGACAAGAAGGCGAAGGGCGCAGATGGCAAG
ACCAAAATTGCGACGCCGCGTGGTGCGGCACCGCCAGGCCAGAAAGGTCAGGCGAATGCCACGCGCAT
CCCGGCAAAGACGCCACCGGCTCCGAAAACCCCGCCTTCCAGCGGTGAACCGCCGAAATCCGGTGACC
GCAGCGGTTATAGCTCTCCGGGTAGCCCGGGTACCCCAGGCAGCCGTAGCCGCACCCCGAGCCTGCCG
ACCCCACCGACCCGCGAGCCGAAGAAAGTGGCGGTGGTTCGTACGCCGCCAAAAAGCCCGAGCTCTGC
CAAGAGCCGTCTGCAAACCGCTCCTGTGCCGATGCCGGACCTGAAGAACGTTAAGTCTAAAATCGGTA
GCACCGAAAATCTGAAGCACCAACCTGGTGGCGGTAAGGTTCAAATCATCAACAAAAAGCTGGACTTG
AGCAATGTACAAAGCAAGTGTGGTAGCAAGGACAATATCAAACACGTCCCGGGTGGTGGTTCCGTCCA
GATTGTGTACAAACCGGTGGACCTGAGCAAGGTTACCAGCAAATGCGGTTCCCTGGGTAACATCCATC
ATAAACCGGGTGGCGGCCAAGTTGAGGTCAAGAGCGAGAAACTGGACTTCAAAGACCGCGTTCAGTCC
AAAATCGGTTCTCTGGACAACATTACGCACGTGCCTGGTGGTGGCAACAAGAAGATTGAAACCCATAA
ACTGACGTTTCGTGAAAATGCGAAGGCGAAAACCGACCACGGCGCAGAGATTGTCTACAAAAGCCCGG
TGGTGAGCGGTGATACCAGCCCGCGTCACCTGTCCAACGTCAGCAGCACGGGCAGCATTGATATGGTG
GATAGCCCGCAGTTGGCTACGCTGGCCGATGAGGTTAGCGCGAGCCTGGCGAAGCAGGGTCTGTGA***CT
```
CGAGCACCACCACCACCACCACTGAGATCCGGCTGCTAACAAAGCCCGAAAGGAAGCTGAGTTGGCTG
CTGCCACCGCTGAGCAATAACTAGCATAACCCCTTGGGGCCTCTAAACGGGTCTTGAGGGGTTTTTG
CTGAAAGGAGGAACTATATCCGGAT
```

Figure 8

A)
expressed sequence of pET 6His-TEV-hTau iso2 (1-441), incorporating 6His tag-TEV site (SEQ ID No.: 40)

```
MGSSHHHHHHSSGENLYFQGSAEPRQEFEVMEDHAGTYGLGDRKDQGGYTMHQDQEGDTDAGL
KESPLQTPTEDGSEEPGSETSDAKSTPTAEDVTAPLVDEGAPGKQAAAQPHTEIPEGTTAEEA
GIGDTPSLEDEAAGHVTQARMVSKSKDGTGSDDKKAKGADGKTKIATPRGAAPPGQKGQANAT
RIPAKTPPAPKTPPSSGEPPKSGDRSGYSSPGSPGTPGSRSRTPSLPTPPTREPKKVAVVRTP
PKSPSSAKSRLQTAPVPMPDLKNVKSKIGSTENLKHQPGGGKVQIINKKLDLSNVQSKCGSKD
NIKHVPGGGSVQIVYKPVDLSKVTSKCGSLGNIHHKPGGGQVEVKSEKLDFKDRVQSKIGSLD
NITHVPGGGNKKIETHKLTFRENAKAKTDHGAEIVYKSPVVSGDTSPRHLSNVSSTGSIDMVD
SPQLATLADEVSASLAKQGL
```

B)
Final expressed sequence from pET 6His-TEV-hTau iso2 (1-441) after TEV cleavage (SEQ ID No.: 41)

```
GSAEPRQEFEVMEDHAGTYGLGDRKDQGGYTMHQDQEGDTDAGLKESPLQTPTEDGSEEPGSE
TSDAKSTPTAEDVTAPLVDEGAPGKQAAAQPHTEIPEGTTAEEAGIGDTPSLEDEAAGHVTQA
RMVSKSKDGTGSDDKKAKGADGKTKIATPRGAAPPGQKGQANATRIPAKTPPAPKTPPSSGEP
PKSGDRSGYSSPGSPGTPGSRSRTPSLPTPPTREPKKVAVVRTPPKSPSSAKSRLQTAPVPMP
DLKNVKSKIGSTENLKHQPGGGKVQIINKKLDLSNVQSKCGSKDNIKHVPGGGSVQIVYKPVD
LSKVTSKCGSLGNIHHKPGGGQVEVKSEKLDFKDRVQSKIGSLDNITHVPGGGNKKIETHKLT
FRENAKAKTDHGAEIVYKSPVVSGDTSPRHLSNVSSTGSIDMVDSPQLATLADEVSASLAKQG
L
```

Figure 9

DNA contruct encoding human Tau isoform 3 for E. coli expression (pET 6His TEV-hTau iso 3 (1-383)) (SEQ ID No.:42).

```
TGGCGAATGGGACGCGCCCTGTAGCGGCGCATTAAGCGCGGCGGGTGTGGTGGTTACGCGCAGCGTGA
CCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCA
CCTCGACCCCAAAAAACTTGATTAGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACTGGAACAACACTC
AACCCTATCTCGGTCTATTCTTTTGATTTATAAGGGATTTTGCCGATTTCGGCCTATTGGTTAAAAAA
TGAGCTGATTTAACAAAAATTTAACGCGAATTTTAACAAAATATTAACGTTTACAATTTCAGGTGGCA
CTTTTCGGGGAAATGTGCGCGGAACCCCTATTTGTTTATTTTTCTAAATACATTCAAATATGTATCCG
CTCATGAGACAATAACCCTGATAAATGCTTCAATAATATTGAAAAAGGAAGAGTATGAGTATTCAACA
TTTCCGTGTCGCCCTTATTCCCTTTTTTGCGGCATTTTGCCTTCCTGTTTTTGCTCACCCAGAAACGC
TGGTGAAAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCCGCATACACTATT
CTCAGAATGACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACAACGATCGG
AGGACCGAAGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGCAGCAATGGCAACA
ACGTTGCGCAAACTATTAACTGGCGAACTACTTACTCTAGCTTCCCGGCAACAATTAATAGACTGGAT
GGAGGCGGATAAAGTTGCAGGACCACTTCTGCGCTCGGCCCTTCCGGCTGGCTGGTTTATTGCTGATA
AATCTGGAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACTTTAGATTG
ATTTAAAACTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGATCTTCTTG
AGATCCTTTTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGCAGATACCA
AATACTGTCCTTCTAGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTGTCTTACCGGGTTGG
ACTCAAGACGATAGTTACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTATGAGAAAGCGCCACGCT
TCCCGAAGGGAGAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCTGACTTGAGCGT
CGATTTTTGTGATGCTCGTCAGGGGGCGGAGCCTATGGAAAAACGCCAGCAACGCGGCCTTTTTACG
GTTCCTGGCCTTTTGCTGGCCTTTTGCTCACATGTTCTTTCCTGCGTTATCCCCTGATTCTGTGGATA
ACCGTATTACCGCCTTTGAGTGAGCTGATACCGCTCGCCGCAGCCGAACGACCGAGCGCAGCGAGTCA
GTGAGCGAGGAAGCGGAAGAGCGCCTGATGCGGTATTTTCTCCTTACGCATCTGTGCGGTATTTCACA
CCGCATATATGGTGCACTCTCAGTACAATCTGCTCTGATGCCGCATAGTTAAGCCAGTATACACTCCG
CTATCGCTACGTGACTGGGTCATGGCTGCGCCCCGACACCCGCCAACACCCGCTGACGCGCCCTGACG
GGCTTGTCTGCTCCCGGCATCCGCTTACAGACAAGCTGTGACCGTCTCCGGGAGCTGCATGTGTCAGA
GGTTTTCACCGTCATCACCGAAACGCGCGAGGCAGCTGCGGTAAAGCTCATCAGCGTGGTCGTGAAGC
GATTCACAGATGTCTGCCTGTTCATCCGCGTCCAGCTCGTTGAGTTTCTCCAGAAGCGTTAATGTCTG
GCTTCTGATAAAGCGGGCCATGTTAAGGGCGGTTTTTTCCTGTTTGGTCACTGATGCCTCCGTGTAAG
GGGGATTTCTGTTCATGGGGGTAATGATACCGATGAAACGAGAGAGGATGCTCACGATACGGGTTACT
GATGATGAACATGCCCGGTTACTGGAACGTTGTGAGGGTAAACAACTGGCGGTATGGATGCGGCGGGA
CCAGAGAAAAATCACTCAGGGTCAATGCCAGCGCTTCGTTAATACAGATGTAGGTGTTCCACAGGGTA
GCCAGCAGCATCCTGCGATGCAGATCCGGAACATAATGGTGCAGGGCGCTGACTTCCGCGTTTCCAGA
CTTTACGAAACACGGAAACCGAAGACCATTCATGTTGTTGCTCAGGTCGCAGACGTTTTGCAGCAGCA
GTCGCTTCACGTTCGCTCGCGTATCGGTGATTCATTCTGCTAACCAGTAAGGCAACCCCGCCAGCCTA
GCCGGGTCCTCAACGACAGGAGCACGATCATGCGCACCCGTGGGGCCGCCATGCCGGCGATAATGGCC
TGCTTCTCGCCGAAACGTTTGGTGGCGGGACCAGTGACGAAGGCTTGAGCGAGGGCGTGCAAGATTCC
GAATACCGCAAGCGACAGGCCGATCATCGTCGCGCTCCAGCGAAAGCGGTCCTCGCCGAAAATGACCC
AGAGCGCTGCCGGCACCTGTCCTACGAGTTGCATGATAAAGAAGACAGTCATAAGTGCGGCGACGATA
```

Figure 9 (continued)

```
GTCATGCCCCGCGCCCACCGGAAGGAGCTGACTGGGTTGAAGGCTCTCAAGGGCATCGGTCGAGATCC
CGGTGCCTAATGAGTGAGCTAACTTACATTAATTGCGTTGCGCTCACTGCCCGCTTTCCAGTCGGGAA
ACCTGTCGTGCCAGCTGCATTAATGAATCGGCCAACGCGCGGGGAGAGGCGGTTTGCGTATTGGGCGC
CAGGGTGGTTTTTCTTTTCACCAGTGAGACGGGCAACAGCTGATTGCCCTTCACCGCCTGGCCCTGAG
AGAGTTGCAGCAAGCGGTCCACGCTGGTTTGCCCCAGCAGGCGAAAATCCTGTTTGATGGTGGTTAAC
GGCGGGATATAACATGAGCTGTCTTCGGTATCGTCGTATCCCACTACCGAGATGTCCGCACCAACGCG
CAGCCCGGACTCGGTAATGGCGCGCATTGCGCCCAGCGCCATCTGATCGTTGGCAACCAGCATCGCAG
TGGGAACGATGCCCTCATTCAGCATTTGCATGGTTTGTTGAAAACCGGACATGGCACTCCAGTCGCCT
TCCCGTTCCGCTATCGGCTGAATTTGATTGCGAGTGAGATATTTATGCCAGCCAGCCAGACGCAGACG
CGCCGAGACAGAACTTAATGGGCCCGCTAACAGCGCGATTTGCTGGTGACCCAATGCGACCAGATGCT
CCACGCCCAGTCGCGTACCGTCTTCATGGGAGAAAATAATACTGTTGATGGGTGTCTGGTCAGAGACA
TCAAGAAATAACGCCGGAACATTAGTGCAGGCAGCTTCCACAGCAATGGCATCCTGGTCATCCAGCGG
ATAGTTAATGATCAGCCCACTGACGCGTTGCGCGAGAAGATTGTGCACCGCCGCTTTACAGGCTTCGA
CGCCGCTTCGTTCTACCATCGACACCACCACGCTGGCACCCAGTTGATCGGCGCGAGATTTAATCGCC
GCGACAATTTGCGACGGCGCGTGCAGGGCCAGACTGGAGGTGGCAACGCCAATCAGCAACGACTGTTT
GCCCGCCAGTTGTTGTGCCACGCGGTTGGGAATGTAATTCAGCTCCGCCATCGCCGCTTCCACTTTTT
CCCGCGTTTTCGCAGAAACGTGGCTGGCCTGGTTCACCACGCGGGAAACGGTCTGATAAGAGACACCG
GCATACTCTGCGACATCGTATAACGTTACTGGTTTCACATTCACCACCCTGAATTGACTCTCTTCCGG
GCGCTATCATGCCATACCGCGAAAGGTTTTGCGCCATTCGATGGTGTCCGGGATCTCGACGCTCTCCC
TTATGCGACTCCTGCATTAGGAAGCAGCCCAGTAGTAGGTTGAGGCCGTTGAGCACCGCCGCCGCAAG
GAATGGTGCATGCAAGGAGATGGCGCCCAACAGTCCCCGGCCACGGGGCCTGCCACCATACCCACGC
CGAAACAAGCGCTCATGAGCCCGAAGTGGCGAGCCCGATCTTCCCCATCGGTGATGTCGGCGATATAG
GCGCCAGCAACCGCACCTGTGGCGCCGGTGATGCCGGCACGATGCGTCCGGCGTAGAGGATCGAGAT
CGATCTCGATCCCGCGAAATTAATACGACTCACTATAGGGAATTGTGAGCGGATAACAATTCCCCTC
TAGAAATAATTTTGTTTAACTTTAAGAAGGAGATATACAT***ATGGGCTCAAGCCACCACCACCACCACC***
*ACAGCAGCGGCGAGAACTTGTACTTTCAAGGATCCGCAGAACCACGTCAAGAATTTGAGGTTATGGAA*
*GATCACGCGGGCACTTACGGTTTGGGTGATCGTAAAGACCAGGGCGGCTATACCATGCATCAAGATCA*
*AGAGGGCGACACCGATGCTGGCTTGAAAGCAGAAGAGGCGGGTATCGGCGACACTCCGTCCCTGGAAG*
*ATGAGGCAGCCGGTCATGTCACGCAGGCGCGTATGGTGAGCAAGAGCAAAGATGGTACGGGTAGCGAC*
*GACAAGAAGGCGAAGGGCGCAGATGGCAAGACCAAAATTGCGACGCCGCGTGGTGCGGCACCGCCAGG*
*CCAGAAAGGTCAGGCGAATGCCACGCGCATCCCGGCAAAGACGCCACCGGCTCCGAAAACCCCGCCTT*
*CCAGCGGTGAACCGCCGAAATCCGGTGACCGCAGCGGTTATAGCTCTCCGGGTAGCCCGGGTACCCCA*
*GGCAGCCGTAGCCGCACCCCGAGCCTGCCGACCCCACCGACCCGCGAGCCGAAGAAAGTGGCGGTGGT*
*TCGTACGCCGCCAAAAAGCCCGAGCTCTGCCAAGAGCCGTCTGCAAACCGCTCCTGTGCCGATGCCGG*
*ACCTGAAGAACGTTAAGTCTAAAATCGGTAGCACCGAAAATCTGAAGCACCAACCTGGTGGCGGTAAG*
*GTTCAAATCATCAACAAAAAGCTGGACTTGAGCAATGTACAAAGCAAGTGTGGTAGCAAGGACAATAT*
*CAAACACGTCCCGGGTGGTGGTTCCGTCCAGATTGTGTACAAACCGGTGGACCTGAGCAAGGTTACCA*
*GCAAATGCGGTTCCCTGGGTAACATCCATCATAAACCGGGTGGCGGCCAAGTTGAGGTCAAGAGCGAG*
*AAACTGGACTTCAAAGACCGCGTTCAGTCCAAAATCGGTTCTCTGGACAACATTACGCACGTGCCTGG*
*TGGTGGCAACAAGAAGATTGAAACCCATAAACTGACGTTTCGTGAAAATGCGAAGCGAAAACCGACC*
*ACGGCGCAGAGATTGTCTACAAAAGCCCGGTGGTGAGCGGTGATACCAGCCCGCGTCACCTGTCCAAC*
*GTCAGCAGCACGGGCAGCATTGATATGGTGGATAGCCCGCAGTTGGCTACGCTGGCCGATGAGGTTAG*
*CGCGAGCCTGGCGAAGCAGGGTCTGTGA*CTCGAGCACCACCACCACCACCACTGAGATCCGGCTGCTA
ACAAAGCCCGAAAGGAAGCTGAGTTGGCTGCTGCCACCGCTGAGCAATAACTAGCATAACCCCTTGGG
GCCTCTAAACGGGTCTTGAGGGGTTTTTTGCTGAAAGGAGGAACTATATCCGGAT
```

Figure 10

A)
Expressed sequence of pET 6His-TEV-hTau iso3 (1-383), incorporating 6His tag-TEV site (SEQ ID No.: 43)

```
MGSSHHHHHHSSGENLYFQGSAEPRQEFEVMEDHAGTYGLGDRKDQGGYTMHQDQEGDTDAGLKAEEA
GIGDTPSLEDEAAGHVTQARMVSKSKDGTGSDDKKAKGADGKTKIATPRGAAPPGQKGQANATRIPAK
TPPAPKTPPSSGEPPKSGDRSGYSSPGSPGTPGSRSRTPSLPTPPTREPKKVAVVRTPPKSPSSAKSR
LQTAPVPMPDLKNVKSKIGSTENLKHQPGGGKVQIINKKLDLSNVQSKCGSKDNIKHVPGGGSVQIVY
KPVDLSKVTSKCGSLGNIHHKPGGGQVEVKSEKLDFKDRVQSKIGSLDNITHVPGGGNKKIETHKLTF
RENAKAKTDHGAEIVYKSPVVSGDTSPRHLSNVSSTGSIDMVDSPQLATLADEVSASLAKQGL
```

B)
Final sequence of pET 6His-TEV-hTau iso3 (1-383) after TEV cleavage (SEQ ID No.: 44):

```
GSAEPRQEFEVMEDHAGTYGLGDRKDQGGYTMHQDQEGDTDAGLKAEEAGIGDTPSLEDEAAGHVTQA
RMVSKSKDGTGSDDKKAKGADGKTKIATPRGAAPPGQKGQANATRIPAKTPPAPKTPPSSGEPPKSGD
RSGYSSPGSPGTPGSRSRTPSLPTPPTREPKKVAVVRTPPKSPSSAKSRLQTAPVPMPDLKNVKSKIG
STENLKHQPGGGKVQIINKKLDLSNVQSKCGSKDNIKHVPGGGSVQIVYKPVDLSKVTSKCGSLGNIH
HKPGGGQVEVKSEKLDFKDRVQSKIGSLDNITHVPGGGNKKIETHKLTFRENAKAKTDHGAEIVYKSP
VVSGDTSPRHLSNVSSTGSIDMVDSPQLATLADEVSASLAKQGL
```

Figure 11

DNA contruct encoding human Tau isoform 4 for E. coli expression (pET 6His TEV-hTau iso 4 (1-352)) (SEQ ID No.:45).

```
TGGCGAATGGGACGCGCCCTGTAGCGGCGCATTAAGCGCGGCGGGTGTGGTGGTTACGCGCAGCGTGA
CCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCA
CCTCGACCCCAAAAAACTTGATTAGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACTGGAACAACACTC
AACCCTATCTCGGTCTATTCTTTTGATTTATAAGGGATTTTGCCGATTTCGGCCTATTGGTTAAAAAA
TGAGCTGATTTAACAAAATTTAACGCGAATTTTAACAAAATATTAACGTTTACAATTTCAGGTGGCA
CTTTTCGGGGAAATGTGCGCGGAACCCCTATTTGTTTATTTTTCTAAATACATTCAAATATGTATCCG
CTCATGAGACAATAACCCTGATAAATGCTTCAATAATATTGAAAAAGGAAGAGTATGAGTATTCAACA
TTTCCGTGTCGCCCTTATTCCCTTTTTTGCGGCATTTTGCCTTCCTGTTTTTGCTCACCCAGAAACGC
TGGTGAAAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCCGCATACACTATT
CTCAGAATGACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACAACGATCGG
AGGACCGAAGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGCAGCAATGGCAACA
ACGTTGCGCAAACTATTAACTGGCGAACTACTTACTCTAGCTTCCCGGCAACAATTAATAGACTGGAT
GGAGGCGGATAAAGTTGCAGGACCACTTCTGCGCTCGGCCCTTCCGGCTGGCTGGTTTATTGCTGATA
AATCTGGAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACTTTAGATTG
ATTTAAAACTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGATCTTCTTG
AGATCCTTTTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGCAGATACCA
AATACTGTCCTTCTAGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTGTCTTACCGGGTTGG
ACTCAAGACGATAGTTACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTATGAGAAAGCGCCACGCT
TCCCGAAGGGAGAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCTGACTTGAGCGT
CGATTTTTGTGATGCTCGTCAGGGGGCGGAGCCTATGGAAAAACGCCAGCAACGCGGCCTTTTTACG
GTTCCTGGCCTTTTGCTGGCCTTTTGCTCACATGTTCTTTCCTGCGTTATCCCCTGATTCTGTGGATA
ACCGTATTACCGCCTTTGAGTGAGCTGATACCGCTCGCCGCAGCCGAACGACCGAGCGCAGCGAGTCA
GTGAGCGAGGAAGCGGAAGAGCGCCTGATGCGGTATTTTCTCCTTACGCATCTGTGCGGTATTTCACA
CCGCATATATGGTGCACTCTCAGTACAATCTGCTCTGATGCCGCATAGTTAAGCCAGTATACACTCCG
CTATCGCTACGTGACTGGGTCATGGCTGCGCCCCGACACCCGCCAACACCCGCTGACGCGCCCTGACG
GGCTTGTCTGCTCCCGGCATCCGCTTACAGACAAGCTGTGACCGTCTCCGGGAGCTGCATGTGTCAGA
GGTTTTCACCGTCATCACCGAAACGCGCGAGGCAGCTGCGGTAAAGCTCATCAGCGTGGTCGTGAAGC
GATTCACAGATGTCTGCCTGTTCATCCGCGTCCAGCTCGTTGAGTTTCTCCAGAAGCGTTAATGTCTG
GCTTCTGATAAAGCGGGCCATGTTAAGGGCGGTTTTTTCCTGTTTGGTCACTGATGCCTCCGTGTAAG
GGGGATTTCTGTTCATGGGGGTAATGATACCGATGAAACGAGAGAGGATGCTCACGATACGGGTTACT
GATGATGAACATGCCCGGTTACTGGAACGTTGTGAGGGTAAACAACTGGCGGTATGGATGCGGCGGGA
CCAGAGAAAAATCACTCAGGGTCAATGCCAGCGCTTCGTTAATACAGATGTAGGTGTTCCACAGGGTA
GCCAGCAGCATCCTGCGATGCAGATCCGGAACATAATGGTGCAGGGCGCTGACTTCCGCGTTTCCAGA
CTTTACGAAACACGGAAACCGAAGACCATTCATGTTGTTGCTCAGGTCGCAGACGTTTTGCAGCAGCA
GTCGCTTCACGTTCGCTCGCGTATCGGTGATTCATTCTGCTAACCAGTAAGGCAACCCCGCCAGCCTA
GCCGGGTCCTCAACGACAGGAGCACGATCATGCGCACCCGTGGGGCCGCCATGCCGGCGATAATGGCC
TGCTTCTCGCCGAAACGTTTGGTGGCGGGACCAGTGACGAAGGCTTGAGCGAGGGCGTGCAAGATTCC
```

Figure 11 (continued)

```
GAATACCGCAAGCGACAGGCCGATCATCGTCGCGCTCCAGCGAAAGCGGTCCTCGCCGAAAATGACCC
AGAGCGCTGCCGGCACCTGTCCTACGAGTTGCATGATAAAGAAGACAGTCATAAGTGCGGCGACGATA
GTCATGCCCCGCGCCCACCGGAAGGAGCTGACTGGGTTGAAGGCTCTCAAGGGCATCGGTCGAGATCC
CGGTGCCTAATGAGTGAGCTAACTTACATTAATTGCGTTGCGCTCACTGCCCGCTTTCCAGTCGGGAA
ACCTGTCGTGCCAGCTGCATTAATGAATCGGCCAACGCGCGGGGAGAGGCGGTTTGCGTATTGGGCGC
CAGGGTGGTTTTTCTTTTCACCAGTGAGACGGGCAACAGCTGATTGCCCTTCACCGCCTGGCCCTGAG
AGAGTTGCAGCAAGCGGTCCACGCTGGTTTGCCCCAGCAGGCGAAAATCCTGTTTGATGGTGGTTAAC
GGCGGGATATAACATGAGCTGTCTTCGGTATCGTCGTATCCCACTACCGAGATGTCCGCACCAACGCG
CAGCCCGGACTCGGTAATGGCGCGCATTGCGCCCAGCGCCATCTGATCGTTGGCAACCAGCATCGCAG
TGGGAACGATGCCCTCATTCAGCATTTGCATGGTTTGTTGAAAACCGGACATGGCACTCCAGTCGCCT
TCCCGTTCCGCTATCGGCTGAATTTGATTGCGAGTGAGATATTTATGCCAGCCAGCCAGACGCAGACG
CGCCGAGACAGAACTTAATGGGCCCGCTAACAGCGCGATTTGCTGGTGACCCAATGCGACCAGATGCT
CCACGCCCAGTCGCGTACCGTCTTCATGGGAGAAAATAATACTGTTGATGGGTGTCTGGTCAGAGACA
TCAAGAAATAACGCCGGAACATTAGTGCAGGCAGCTTCCACAGCAATGGCATCCTGGTCATCCAGCGG
ATAGTTAATGATCAGCCCACTGACGCGTTGCGCGAGAAGATTGTGCACCGCCGCTTTACAGGCTTCGA
CGCCGCTTCGTTCTACCATCGACACCACCACGCTGGCACCCAGTTGATCGGCGCGAGATTTAATCGCC
GCGACAATTTGCGACGGCGCGTGCAGGGCCAGACTGGAGGTGGCAACGCCAATCAGCAACGACTGTTT
GCCCGCCAGTTGTTGTGCCACGCGGTTGGGAATGTAATTCAGCTCCGCCATCGCCGCTTCCACTTTTT
CCCGCGTTTTCGCAGAAACGTGGCTGGCCTGGTTCACCACGCGGGAAACGGTCTGATAAGAGACACCG
GCATACTCTGCGACATCGTATAACGTTACTGGTTTCACATTCACCACCCTGAATTGACTCTCTTCCGG
GCGCTATCATGCCATACCGCGAAAGGTTTTGCGCCATTCGATGGTGTCCGGGATCTCGACGCTCTCCC
TTATGCGACTCCTGCATTAGGAAGCAGCCCAGTAGTAGGTTGAGGCCGTTGAGCACCGCCGCCGCAAG
GAATGGTGCATGCAAGGAGATGGCGCCCAACAGTCCCCGGCCACGGGCCTGCCACCATACCCACGC
CGAAACAAGCGCTCATGAGCCCGAAGTGGCGAGCCCGATCTTCCCCATCGGTGATGTCGGCGATATAG
GCGCCAGCAACCGCACCTGTGGCGCCGGTGATGCCGGCCACGATGCGTCCGGCGTAGAGGATCGAGAT
CGATCTCGATCCCGCGAAATTAATACGACTCACTATAGGGGAATTGTGAGCGGATAACAATTCCCCTC
TAGAAATAATTTTGTTTAACTTTAAGAAGGAGATATACAT***ATGGGCTCAAGCCACCACCACCACCACC
ACAGCAGCGGCGAGAACTTGTACTTTCAAGGATCCGCAGAACCACGTCAAGAATTTGAGGTTATGGAA
GATCACGCGGGCACTTACGGTTTGGGTGATCGTAAAGACCAGGGCGGCTATACCATGCATCAAGATCA
AGAGGGCGACACCGATGCTGGCTTGAAAGCAGAAGAGGCGGGTATCGGCGACACTCCGTCCCTGGAAG
ATGAGGCAGCCGGTCATGTCACGCAGGCGCGTATGGTGAGCAAGAGCAAAGATGGTACGGGTAGCGAC
GACAAGAAGGCGAAGGCGCAGATGGCAAGACCAAAATTGCGACGCCGCGTGGTGCGGCACCGCCAGG
CCAGAAAGGTCAGGCGAATGCCACGCGCATCCCGGCAAAGACGCCACCGGCTCCGAAAACCCCGCCTT
CCAGCGGTGAACCGCCGAAATCCGGTGACCGCAGCGGTTATAGCTCTCCGGGTAGCCCGGGTACCCCA
GGCAGCCGTAGCCGCACCCCGAGCCTGCCGACCCCACCGACCCGCGAGCCGAAGAAAGTGGCGGTGGT
TCGTACGCCGCCAAAAAGCCCGAGCTCTGCCAAGAGCCGTCTGCAAACCGCTCCTGTGCCGATGCCGG
ACCTGAAGAACGTTAAGTCTAAAATCGGTAGCACCGAAAATCTGAAGCACCAACCTGGTGGCGGTAAG
GTCCAGATTGTGTACAAACCGGTGGACCTGAGCAAGGTTACCAGCAAATGCGGTTCCCTGGGTAACAT
CCATCATAAACCGGGTGGCGGCCAAGTTGAGGTCAAGAGCGAGAAACTGGACTTCAAAGACCGCGTTC
AGTCCAAAATCGGTTCTCTGGACAACATTACGCACGTGCCTGGTGGTGGCAACAAGAAGATTGAAACC
CATAAACTGACGTTTCGTGAAAATGCGAAGGCGAAAACCGACCACGGCGCAGAGATTGTCTACAAAAG
CCCGGTGGTGAGCGGTGATACCAGCCCGCGTCACCTGTCCAACGTCAGCAGCACGGGCAGCATTGATA
TGGTGGATAGCCCGCAGTTGGCTACGCTGGCCGATGAGGTTAGCGCGAGCCTGGCGAAGCAGGGTCTG
TGA***CTCGAGCACCACCACCACCACCACTGAGATCCGGCTGCTAACAAAGCCCGAAAGGAAGCTGAGTT
GGCTGCTGCCACCGCTGAGCAATAACTAGCATAACCCCTTGGGGCCTCTAAACGGGTCTTGAGGGGTT
TTTTGCTGAAAGGAGGAACTATATCCGGAT
```

Figure 12

A) Expressed amino acid sequence of pET 6His-TEV-hTau iso4(1-352), incorporating 6His tag-TEV site – hTau (1-352) (SEQ ID No.: 46)

MGSSHHHHHHSSGENLYFQGSAEPRQEFEVMEDHAGTYGLGDRKDQGGYTMHQDQEGDTDAGLKAEEA
GIGDTPSLEDEAAGHVTQARMVSKSKDGTGSDDKKAKGADGKTKIATPRGAAPPGQKGQANATRIPAK
TPPAPKTPPSSGEPPKSGDRSGYSSPGSPGTPGSRSRTPSLPTPPTREPKKVAVVRTPPKSPSSAKSR
LQTAPVPMPDLKNVKSKIGSTENLKHQPGGGKVQIVYKPVDLSKVTSKCGSLGNIHHKPGGGQVEVKS
EKLDFKDRVQSKIGSLDNITHVPGGGNKKIETHKLTFRENAKAKTDHGAEIVYKSPVVSGDTSPRHLS
NVSSTGSIDMVDSPQLATLADEVSASLAKQGL

B) Final sequence of pET 6His-TEV-hTau iso4(1-352) after TEV cleavage (SEQ ID No.: 47)

GSAEPRQEFEVMEDHAGTYGLGDRKDQGGYTMHQDQEGDTDAGLKAEEAGIGDTPSLEDEAAGHVTQA
RMVSKSKDGTGSDDKKAKGADGKTKIATPRGAAPPGQKGQANATRIPAKTPPAPKTPPSSGEPPKSGD
RSGYSSPGSPGTPGSRSRTPSLPTPPTREPKKVAVVRTPPKSPSSAKSRLQTAPVPMPDLKNVKSKIG
STENLKHQPGGGKVQIVYKPVDLSKVTSKCGSLGNIHHKPGGGQVEVKSEKLDFKDRVQSKIGSLDNI
THVPGGGNKKIETHKLTFRENAKAKTDHGAEIVYKSPVVSGDTSPRHLSNVSSTGSIDMVDSPQLATL
ADEVSASLAKQGL

Figure 13

DNA contruct encoding human Tau isoform 5 for E. coli expression (pET 6His TEV-hTau iso 5 (1-412)) (SEQ ID No.:48).

```
TGGCGAATGGGACGCGCCCTGTAGCGGCGCATTAAGCGCGGCGGGTGTGGTGGTTACGCGCAGCGTGA
CCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCA
CCTCGACCCCAAAAAACTTGATTAGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACTGGAACAACACTC
AACCCTATCTCGGTCTATTCTTTTGATTTATAAGGGATTTTGCCGATTTCGGCCTATTGGTTAAAAAA
TGAGCTGATTTAACAAAAATTTAACGCGAATTTTAACAAAATATTAACGTTTACAATTTCAGGTGGCA
CTTTTCGGGGAAATGTGCGCGGAACCCCTATTTGTTTATTTTTCTAAATACATTCAAATATGTATCCG
CTCATGAGACAATAACCCTGATAAATGCTTCAATAATATTGAAAAAGGAAGAGTATGAGTATTCAACA
TTTCCGTGTCGCCCTTATTCCCTTTTTTGCGGCATTTTGCCTTCCTGTTTTTGCTCACCCAGAAACGC
TGGTGAAAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCCGCATACACTATT
CTCAGAATGACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACAACGATCGG
AGGACCGAAGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGCAGCAATGGCAACA
ACGTTGCGCAAACTATTAACTGGCGAACTACTTACTCTAGCTTCCCGGCAACAATTAATAGACTGGAT
GGAGGCGGATAAAGTTGCAGGACCACTTCTGCGCTCGGCCCTTCCGGCTGGCTGGTTTATTGCTGATA
AATCTGGAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACTTTAGATTG
ATTTAAAACTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGATCTTCTTG
AGATCCTTTTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGCAGATACCA
AATACTGTCCTTCTAGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTGTCTTACCGGGTTGG
ACTCAAGACGATAGTTACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTATGAGAAAGCGCCACGCT
TCCCGAAGGGAGAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCTGACTTGAGCGT
CGATTTTTGTGATGCTCGTCAGGGGGCGGAGCCTATGGAAAAACGCCAGCAACGCGGCCTTTTTACG
GTTCCTGGCCTTTTGCTGGCCTTTTGCTCACATGTTCTTTCCTGCGTTATCCCCTGATTCTGTGGATA
ACCGTATTACCGCCTTTGAGTGAGCTGATACCGCTCGCCGCAGCCGAACGACCGAGCGCAGCGAGTCA
GTGAGCGAGGAAGCGGAAGAGCGCCTGATGCGGTATTTTCTCCTTACGCATCTGTGCGGTATTTCACA
CCGCATATATGGTGCACTCTCAGTACAATCTGCTCTGATGCCGCATAGTTAAGCCAGTATACACTCCG
CTATCGCTACGTGACTGGGTCATGGCTGCGCCCCGACACCCGCCAACACCCGCTGACGCGCCCTGACG
GGCTTGTCTGCTCCCGGCATCCGCTTACAGACAAGCTGTGACCGTCTCCGGGAGCTGCATGTGTCAGA
GGTTTTCACCGTCATCACCGAAACGCGCGAGGCAGCTGCGGTAAAGCTCATCAGCGTGGTCGTGAAGC
GATTCACAGATGTCTGCCTGTTCATCCGCGTCCAGCTCGTTGAGTTTCTCCAGAAGCGTTAATGTCTG
GCTTCTGATAAAGCGGGCCATGTTAAGGGCGGTTTTTTCCTGTTTGGTCACTGATGCCTCCGTGTAAG
GGGGATTTCTGTTCATGGGGGTAATGATACCGATGAAACGAGAGAGGATGCTCACGATACGGGTTACT
GATGATGAACATGCCCGGTTACTGGAACGTTGTGAGGGTAAACAACTGGCGGTATGGATGCGGCGGGA
CCAGAGAAAAATCACTCAGGGTCAATGCCAGCGCTTCGTTAATACAGATGTAGGTGTTCCACAGGGTA
GCCAGCAGCATCCTGCGATGCAGATCCGGAACATAATGGTGCAGGGCGCTGACTTCCGCGTTTCCAGA
CTTTACGAAACACGGAAACCGAAGACCATTCATGTTGTTGCTCAGGTCGCAGACGTTTTGCAGCAGCA
GTCGCTTCACGTTCGCTCGCGTATCGGTGATTCATTCTGCTAACCAGTAAGGCAACCCCGCCAGCCTA
GCCGGGTCCTCAACGACAGGAGCACGATCATGCGCACCCGTGGGCCGCCATGCCGGCGATAATGGCC
TGCTTCTCGCCGAAACGTTTGGTGGCGGGACCAGTGACGAAGGCTTGAGCGAGGGCGTGCAAGATTCC
```

Figure 13 (continued)

```
GAATACCGCAAGCGACAGGCCGATCATCGTCGCGCTCCAGCGAAAGCGGTCCTCGCCGAAAATGACCC
AGAGCGCTGCCGGCACCTGTCCTACGAGTTGCATGATAAAGAAGACAGTCATAAGTGCGGCGACGATA
GTCATGCCCCGCGCCCACCGGAAGGAGCTGACTGGGTTGAAGGCTCTCAAGGGCATCGGTCGAGATCC
CGGTGCCTAATGAGTGAGCTAACTTACATTAATTGCGTTGCGCTCACTGCCCGCTTTCCAGTCGGGAA
ACCTGTCGTGCCAGCTGCATTAATGAATCGGCCAACGCGCGGGGAGAGGCGGTTTGCGTATTGGGCGC
CAGGGTGGTTTTTCTTTTCACCAGTGAGACGGGCAACAGCTGATTGCCCTTCACCGCCTGGCCCTGAG
AGAGTTGCAGCAAGCGGTCCACGCTGGTTTGCCCCAGCAGGCGAAATCCTGTTTGATGGTGGTTAAC
GGCGGGATATAACATGAGCTGTCTTCGGTATCGTCGTATCCCACTACCGAGATGTCCGCACCAACGCG
CAGCCCGGACTCGGTAATGGCGCGCATTGCGCCCAGCGCCATCTGATCGTTGGCAACCAGCATCGCAG
TGGGAACGATGCCCTCATTCAGCATTTGCATGGTTTGTTGAAAACCGGACATGGCACTCCAGTCGCCT
TCCCGTTCCGCTATCGGCTGAATTTGATTGCGAGTGAGATATTTATGCCAGCCAGCCAGACGCAGACG
CGCCGAGACAGAACTTAATGGGCCCGCTAACAGCGCGATTTGCTGGTGACCCAATGCGACCAGATGCT
CCACGCCCAGTCGCGTACCGTCTTCATGGGAGAAAATAATACTGTTGATGGGTGTCTGGTCAGAGACA
TCAAGAAATAACGCCGGAACATTAGTGCAGGCAGCTTCCACAGCAATGGCATCCTGGTCATCCAGCGG
ATAGTTAATGATCAGCCCACTGACGCGTTGCGCGAGAAGATTGTGCACCGCCGCTTTACAGGCTTCGA
CGCCGCTTCGTTCTACCATCGACACCACCACGCTGGCACCCAGTTGATCGGCGCGAGATTTAATCGCC
GCGACAATTTGCGACGGCGCGTGCAGGGCCAGACTGGAGGTGGCAACGCCAATCAGCAACGACTGTTT
GCCCGCCAGTTGTTGTGCCACGCGGTTGGGAATGTAATTCAGCTCCGCCATCGCCGCTTCCACTTTTT
CCCGCGTTTTCGCAGAAACGTGGCTGGCCTGGTTCACCACGCGGGAAACGGTCTGATAAGAGACACCG
GCATACTCTGCGACATCGTATAACGTTACTGGTTTCACATTCACCACCCTGAATTGACTCTCTTCCGG
GCGCTATCATGCCATACCGCGAAAGGTTTTGCGCCATTCGATGGTGTCCGGGATCTCGACGCTCTCCC
TTATGCGACTCCTGCATTAGGAAGCAGCCCAGTAGTAGGTTGAGGCCGTTGAGCACCGCCGCCGCAAG
GAATGGTGCATGCAAGGAGATGGCGCCCAACAGTCCCCGGCCACGGGCCTGCCACCATACCCACGC
CGAAACAAGCGCTCATGAGCCCGAAGTGGCGAGCCCGATCTTCCCCATCGGTGATGTCGGCGATATAG
GCGCCAGCAACCGCACCTGTGGCGCCGGTGATGCCGGCCACGATGCGTCCGGCGTAGAGGATCGAGAT
CGATCTCGATCCCGCGAAATTAATACGACTCACTATAGGGGAATTGTGAGCGGATAACAATTCCCCTC
TAGAAATAATTTTGTTTAACTTTAAGAAGGAGATATACATATGGGCTCAAGCCACCACCACCACCACC
ACAGCAGCGGCGAGAACTTGTACTTTCAAGGATCCGCAGAACCACGTCAAGAATTTGAGGTTATGGAA
GATCACGCGGGCACTTACGGTTTGGGTGATCGTAAAGACCAGGGCGGCTATACCATGCATCAAGATCA
AGAGGGCGACACCGATGCTGGCTTGAAAGAGTCGCCGCTGCAGACTCCGACCGAGGATGGCAGCGAAG
AGCCGGGCAGCGAGACTAGCGATGCGAAGTCGACCCCGACCGCCGAGGCAGAAGAGGCGGGTATCGGC
GACACTCCGTCCCTGGAAGATGAGGCAGCCGGTCATGTCACGCAGGCGCGTATGGTGAGCAAGAGCAA
AGATGGTACGGGTAGCGACGACAAGAAGGCGAAGGGCGCAGATGGCAAGACCAAAATTGCGACGCCGC
GTGGTGCGGCACCGCCAGGCCAGAAAGGTCAGGCGAATGCCACGCGCATCCCGGCAAAGACGCCACCG
GCTCCGAAAACCCCGCCTTCCAGCGGTGAACCGCCGAAATCCGGTGACCGCAGCGGTTATAGCTCTCC
GGGTAGCCCGGGTACCCCAGGCAGCCGTAGCCGCACCCCGAGCCTGCCGACCCCACCGACCCGCGAGC
CGAAGAAAGTGGCGGTGGTTCGTACGCCGCCAAAAAGCCCGAGCTCTGCCAAGAGCCGTCTGCAAACC
GCTCCTGTGCCGATGCCGGACCTGAAGAACGTTAAGTCTAAAATCGGTAGCACCGAAAATCTGAAGCA
CCAACCTGGTGGCGGTAAGGTTCAAATCATCAACAAAAAGCTGGACTTGAGCAATGTACAAAGCAAGT
GTGGTAGCAAGGACAATATCAAACACGTCCCGGGTGGTGGTTCCGTCCAGATTGTGTACAAACCGGTG
GACCTGAGCAAGGTTACCAGCAAATGCGGTTCCCTGGGTAACATCCATCATAAACCGGGTGGCGGCCA
AGTTGAGGTCAAGAGCGAGAAACTGGACTTCAAAGACCGCGTTCAGTCCAAAATCGGTTCTCTGGACA
ACATTACGCACGTGCCTGGTGGTGGCAACAAGAAGATTGAAACCCATAAACTGACGTTTCGTGAAAAT
GCGAAGGCGAAAACCGACCACGGCGCAGAGATTGTCTACAAAAGCCCGGTGGTGAGCGGTGATACCAG
CCCGCGTCACCTGTCCAACGTCAGCAGCACGGGCAGCATTGATATGGTGGATAGCCCGCAGTTGGCTA
CGCTGGCCGATGAGGTTAGCGCGAGCCTGGCGAAGCAGGGTCTGTGACTCGAGCACCACCACCACCAC
CACTGAGATCCGGCTGCTAACAAAGCCCGAAAGGAAGCTGAGTTGGCTGCTGCCACCGCTGAGCAATA
ACTAGCATAACCCCTTGGGGCCTCTAAACGGGTCTTGAGGGGTTTTTTGCTGAAAGGAGGAACTATAT
CCGGAT
```

Figure 14

A) Expressed amino acid sequence of pET 6His-TEV-hTau iso5(1-412), incorporating 6His tag-TEV site – hTau (1-412) (SEQ ID No.: 49)

MGSSHHHHHHSSGENLYFQGSAEPRQEFEVMEDHAGTYGLGDRKDQGGYTMHQDQEGDTDAGLKESPL
QTPTEDGSEEPGSETSDAKSTPTAEAEEAGIGDTPSLEDEAAGHVTQARMVSKSKDGTGSDDKKAKGA
DGKTKIATPRGAAPPGQKGQANATRIPAKTPPAPKTPPSSGEPPKSGDRSGYSSPGSPGTPGSRSRTP
SLPTPPTREPKKVAVVRTPPKSPSSAKSRLQTAPVPMPDLKNVKSKIGSTENLKHQPGGGKVQIINKK
LDLSNVQSKCGSKDNIKHVPGGGSVQIVYKPVDLSKVTSKCGSLGNIHHKPGGGQVEVKSEKLDFKDR
VQSKIGSLDNITHVPGGGNKKIETHKLTFRENAKAKTDHGAEIVYKSPVVSGDTSPRHLSNVSSTGSI
DMVDSPQLATLADEVSASLAKQGL

B) Final sequence of pET 6His-TEV-hTau iso5(1-412) after TEV cleavage (SEQ ID No.: 50)

GSAEPRQEFEVMEDHAGTYGLGDRKDQGGYTMHQDQEGDTDAGLKESPLQTPTEDGSEEPGSETSDAK
STPTAEAEEAGIGDTPSLEDEAAGHVTQARMVSKSKDGTGSDDKKAKGADGKTKIATPRGAAPPGQKG
QANATRIPAKTPPAPKTPPSSGEPPKSGDRSGYSSPGSPGTPGSRSRTPSLPTPPTREPKKVAVVRTP
PKSPSSAKSRLQTAPVPMPDLKNVKSKIGSTENLKHQPGGGKVQIINKKLDLSNVQSKCGSKDNIKHV
PGGGSVQIVYKPVDLSKVTSKCGSLGNIHHKPGGGQVEVKSEKLDFKDRVQSKIGSLDNITHVPGGGN
KKIETHKLTFRENAKAKTDHGAEIVYKSPVVSGDTSPRHLSNVSSTGSIDMVDSPQLATLADEVSASL
AKQGL

Figure 15

DNA contruct encoding human Tau isoform 2 for mammalian expression (pMH-10His-TEV-hTau iso2(1-441)) (SEQ ID No.:51).

```
GCTGCTTCGCGATGTACGGGCCAGATATACGCGTTTTGAGATTTCTGTCGCCGACTAAATTCATGTCG
CGCGATAGTGGTGTTTATCGCCGATAGAGATGGCGATATTGGAAAAATCGGCGGCCGCCGATATTTGA
AAATATGGCATATTGAAAATGTCGCCGATGTGAGTTTCTGTGTAACTGACATCGCCATTTTTCCAAAA
GTGATTTTTGGGCATACGCGGTATCTGGCGATAGCGCTTATATCGTTTACGGGGGATGGCGATAGACG
ACTTTGGTGACTTGGGCGATTCTGTGTGTCGCAAATATCGCAGTTTCGATATAGGTGACAGACGATAT
GAGGCTATATCGCCGATAGAGGCGACATCAAGCTGGCACATGGCCAATGCATATCGATCTATACATTG
AATCAATATTGGCCATTAGCCATATTATTCATTGGTTATATAGCATAAATCAATATTGGCTATTGGCC
ATTGCATACGTTGTATCCATATCATAATATGTACATTTATATTGGCTCATGTCCAACATTACCGCCAT
GTTGACATTGATTATTGACTAGTTATTAATAGTAATCAATTACGGGGTCATTAGTTCATAGCCCATAT
ATGGAGTTCCGCGTTACATAACTTACGGTAAATGGCCCGCCTGGCTGACCGCCCAACGACCCCGCCC
ATTGACGTCAATAATGACGTATGTTCCCATAGTAACGCCAATAGGGACTTTCCATTGACGTCAATGGG
TGGAGTATTTACGGTAAACTGCCCACTTGGCAGTACATCAAGTGTATCATATGCCAAGTACGCCCCCT
ATTGACGTCAATGACGGTAAATGGCCCGCCTGGCATTATGCCCAGTACATGACCTTATGGGACTTTCC
TACTTGGCAGTACATCTACGTATTAGTCATCGCTATTACAATGGTGATGCGGTTTTGGCAGTACATCA
ATGGGCGTGGATAGCGGTTTGACTCACGGGGATTTCCAAGTCTCCACCCCATTGACGTCAATGGGAGT
TTGTTTTGGCACCAAAATCAACGGGACTTTCCAAAATGTCGTAACAACTCCGCCCCATTGACGCAAAT
GGGCGGTAGGCGTGTACGGTGGGAGGTCTATATAAGCAGAACTCGTTTAGTGAACCGTCAGATCGCCT
GGAGACGCCATCCACGCTGTTTTGACCTCCATAGAAGACACCGGGACCGATCCAGCCTCCGCGGCCGG
GAACGGTGCATTGGAACGCGGATTCCCCGTGCCAAGAGTGACGTAAGTACCGCCTATAGAGTCTATAG
GCCCACCCCATTGGCTTCTTATGCATGCTATACTGTTTTTGGCTTGGGGTCTATACACCCCCGCTTCC
TCATGTTATAGGTGATGGTATAGCTTAGCCTATAGGTGTGGGTTATTGACCATTATTGACCACTCCCC
TATTGGTGACGATACTTTCCATTACTAATCCATAACATGGCTCTTTGCCACAACTCTCTTTATTGGCT
ATATGCCAATACACTGTCCTTCAGAGACTGACACGGACTCTGTATTTTTACAGGATGGGGTCTCATTT
ATTATTTACAAATTCACATATACAACACCACCGTCCCCAGTGCCCGCAGTTTTTATTAAACATAACGT
GGGATCTCCACGCGAATCTAGGGTACGTGTTACGGACATGGGCTATTCTCAGGTAGCGGCGGAGCTTC
TACATCCGAGCCCTGCTCCCATGCCTCCAGCGAATCATGGTCGCTCGGCAGCTCCTTGCTCCTAACAG
TGGAGGCCAGACTTAGGCACAGCACGATGCCCACCACCACCAGTGTGCCGCACAAGGCCGTGGCGGTA
GGGTATGTGTCTGAAAATGAACTAGGGGAGCGGGCTTGCACCGCTGACGCATTTGGAAGACTTAAGGC
AGCGGCAGAAGAAGATGCAGGCAACTGAGTTGTTGTTCTGATAAGAGTCAGAGGTAACTCCCGTTG
CGGTGCTGTTAACGGTGGAGGGCAGTGTAGTCTGAGCAGTACTCGTTGCTGCCGCACGCGCCACCAGA
CATAATAGCTGACAGACTAACAGACTGTTCCTTTCAATGGGTCTTTTATGCAGTCACCGTCCTTGACA
CGAAGCTTGCCACCATGGGCTCAAGCCACCATCACCACCACCATCATCACCACCACAGCAGCGGCGAG
AACTTGTACTTTCAAGGATCCGCTGAGCCCCGCCAGGAGTTCGAAGTGATGGAAGATCACGCTGGGAC
GTACGGGTTGGGGGACAGGAAAGATCAGGGGGGCTACACCATGCACCAAGACCAAGAGGGTGACACGG
ACGCTGGCCTGAAAGAATCTCCCCTGCAGACCCCCACTGAGGACGGATCTGAGGAACCGGGCTCTGAA
ACCTCTGATGCTAAGAGCACTCCAACAGCGGAAGATGTGACAGCACCCTTAGTGGATGAGGGAGCTCC
CGGCAAGCAGGCTGCCGCGCAGCCCCACACGGAGATCCCAGAAGGAACCACAGCTGAAGAAGCAGGCA
TTGGAGACACCCCCAGCCTGGAAGACGAAGCTGCTGGTCACGTGACCCAAGCTCGCATGGTCAGTAAA
AGCAAAGACGGGACTGGAAGCGATGACAAAAAAGCCAAGGGGGCTGATGGTAAAACGAAGATCGCCAC
ACCGCGGGAGCAGCCCCTCCAGGCCAGAAGGGCCAGGCCAACGCCACCAGGATTCCAGCAAAAACCC
CGCCCGCTCCAAAGACACCACCCAGCTCTGGTGAACCTCCAAAATCAGGGGATCGCAGCGGCTACAGC
AGCCCCGGCTCCCCAGGCACTCCCGGCAGCCGCTCCCGCACCCCGTCCCTTCCAACCCCACCCACCCG
GGAGCCCAAGAAGGTGGCAGTGGTCCGTACTCCACCCAAGTCGCCGTCTTCCGCCAAGAGCCGCCTGC
AGACAGCCCCCGTGCCCATGCCAGACCTGAAGAATGTCAAGTCCAAGATCGGCTCCACTGAGAACCTG
AAGCACCAGCCGGGAGGCGGAAGGTGCAGATAATTAATAAGAAGCTGGATCTTAGCAACGTCCAGTC
CAAGTGTGGCTCAAAGGATAATATCAAACACGTCCCGGGAGGCGGCAGTGTGCAAATAGTCTACAAAC
CAGTTGACCTGAGCAAGGTGACCTCCAAGTGTGGCTCATTAGGCAACATCCATCATAAACCAGGAGGT
GGCCAGGTGGAAGTAAAATCTGAGAAGCTAGACTTCAAGGACAGAGTCCAGTCGAAGATTGGGTCCCT
GGACAATATCACCCACGTCCCTGGCGGAGGAAATAAAAAGATTGAAACCCACAAGCTGACCTTCCGCG
AGAACGCCAAAGCCAAGACAGACCACGGGCGGAGATCGTGTACAAGTCGCCAGTGGTGTCTGGGGAC
ACGTCTCCACGGCATCTCAGCAATGTCTCCTCCACCGGCAGCATCGACATGGTAGACTCGCCCCAGCT
CGCCACGCTAGCTGACGAGGTGTCTGCCTCCCTGGCCAAGCAGGGTTTGTGACTCGAGGAGAACTTGT
```

Figure 15 (continued)

```
ACTTCCAGGGAAGTGGTGGCAGTCATCACCATCACCATCACCATCACCATCACTGAGAATTCATTGAT
CATAATCAGCCATACCACATTTGTAGAGGTTTTACTTGCTTTAAAAAACCTCCCACACCTCCCCCTGA
ACCTGAAACATAAAATGAATGCAATTGTTGTTGTTAACTTGTTTATTGCAGCTTATAATGGTTACAAA
TAAAGCAATAGCATCACAAATTTCACAAATAAAGCATTTTTTTCACTGCATTCTAGTTGTGGTTTGTC
CAAACTCATCAATGTATCTTATCATGTCTGAATCCTCTACGCCGGACGCATCGTGGCCGGCATCACCG
GCGCCACAGGTGCGGTTGCTGGCGCCTATATCGCCGACATCACCGATGGGGAAGATCGGGCTCGCCAC
TTCGGGCTCATGAGCGCTTGTTTCGGCGTGGGTATGGTGGCAGGCCCCGTGGCCGGGGACTGTTGGG
CGCCATCTCCTTGCATGCACCATTCCTTGCGGCGGCGGTGCTCAACGGCCTCAACCTACTACTGGGCT
GCTTCCTAATGCAGGAGTCGCATAAGGGAGAGCGTCGACTGGGGCGCCCTCTGGTAAGGTTGGGAAGC
CCTGCAAAGTAAACTGGATGGCTTTCTCGCCGCCAAGCATCTGATGGCGCAGGGGATCAAGCTCTGAT
CAAGAGACAGGATGAGGATCGTTTCGCATGATTGAACAAGATGGATTGCACGCAGGTTCTCCGGCCGC
TTGGGTGGAGAGGCTATTCGGCTATGACTGGGCACAACAGACAATCGGCTGCTCTGATGCCGCCGTGT
TCCGGCTGTCAGCGCAGGGGCGCCCGGTTCTTTTTGTCAAGACCGACCTGTCCGGTGCCCTGAATGAA
CTGCAAGACGAGGCAGCGCGGCTATCGTGGCTGGCCACGACGGGCGTTCCTTGCGCAGCAGTGCTCGA
CGTTGTCACTGAAGCGGGAAGGGACTGGCTGCTATTGGGCGAAGTGCCGGGGCAGGATCTCCTGTCAT
CTCACCTTGCTCCTGCCGAGAAAGTATCCATCATGGCTGATGCAATGCGGCGGCTGCATACGCTTGAT
CCGGCTACCTGCCCATTCGACCACCAAGCGAAACATCGCATCGAGCGAGCACGTACTCGGATGGAAGC
CGGTCTTGTCGATCAGGATGATCTGGACGAAGAGCATCAGGGGCTCGCGCCAGCCGAACTGTTCGCCA
GGCTCAAGGCGAGCATGCCCGACGGCGAGGATCTCGTCGTGACCCACGGCGATGCCTGCTTGCCGAAT
ATCATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCTTCC
TCGTGCTTTACGGTATCGCCGCTCCCGATTCGCAGCGCATCGCCTTCTATCGCCTTCTTGACGAGTTC
TTCTGAATTATTAACGCTTACAATTTCCTGATGCGGTATTTTCTCCTTACGCATCTGTGCGGTATTTC
ACACCGCATCAGGTGGCACTTTTCGGGGAAATGTGCGCGGAACCCCTATTTGTTTATTTTTCTAAATA
CATTCAAATATGTATCCGCTCATGAGACAATAACCCTGATAAATGCTTCAATAATAGCACGTGCTAAA
ACTTCATTTTTAATTTAAAAGGATCTAGGTGAAGATCCTTTTTGATAATCTCATGACCAAAATCCCTT
AACGTGAGTTTTCGTTCCACTGAGCGTCAGACCCCGTAGAAAAGATCAAAGGATCTTCTTGAGATCCT
TTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTG
TTCTTCTAGTGTAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTTGAGCGTCGATTTT
TGTGATGCTCGTCAGGGGGCGGAGCCTATGGAAAAACGCCAGCAACGCGGCCTTTTTACGGTTCCTG
GCCTTTTGCTGGCCTTTTGCTCACATGTTCTT
```

Figure 16

A) Expressed amino acid sequence of pMH 10His-TEV-hTau iso2(1-441), incorporating 10His tag-TEV site – hTau (1-441) (SEQ ID No.: 52)

MGSSHHHHHHHHHHSSGENLYFQGSAEPRQEFEVMEDHAGTYGLGDRKDQGGYTMHQDQEGDTDAGLK
ESPLQTPTEDGSEEPGSETSDAKSTPTAEDVTAPLVDEGAPGKQAAAQPHTEIPEGTTAEEAGIGDTP
SLEDEAAGHVTQARMVSKSKDGTGSDDKKAKGADGKTKIATPRGAAPPGQKGQANATRIPAKTPPAPK
TPPSSGEPPKSGDRSGYSSPGSPGTPGSRSRTPSLPTPPTREPKKVAVVRTPPKSPSSAKSRLQTAPV
PMPDLKNVKSKIGSTENLKHQPGGGKVQIINKKLDLSNVQSKCGSKDNIKHVPGGGSVQIVYKPVDLS
KVTSKCGSLGNIHHKPGGGQVEVKSEKLDFKDRVQSKIGSLDNITHVPGGGNKKIETHKLTFRENAKA
KTDHGAEIVYKSPVVSGDTSPRHLSNVSSTGSIDMVDSPQLATLADEVSASLAKQGL

B) Final sequence of pMH 10His-TEV-hTau iso2(1-441) after TEV cleavage (SEQ ID No.: 53):

GSAEPRQEFEVMEDHAGTYGLGDRKDQGGYTMHQDQEGDTDAGLKESPLQTPTEDGSEEPGSETSDAK
STPTAEDVTAPLVDEGAPGKQAAAQPHTEIPEGTTAEEAGIGDTPSLEDEAAGHVTQARMVSKSKDGT
GSDDKKAKGADGKTKIATPRGAAPPGQKGQANATRIPAKTPPAPKTPPSSGEPPKSGDRSGYSSPGSP
GTPGSRSRTPSLPTPPTREPKKVAVVRTPPKSPSSAKSRLQTAPVPMPDLKNVKSKIGSTENLKHQPG
GGKVQIINKKLDLSNVQSKCGSKDNIKHVPGGGSVQIVYKPVDLSKVTSKCGSLGNIHHKPGGGQVEV
KSEKLDFKDRVQSKIGSLDNITHVPGGGNKKIETHKLTFRENAKAKTDHGAEIVYKSPVVSGDTSPRH
LSNVSSTGSIDMVDSPQLATLADEVSASLAKQGL

Figure 17
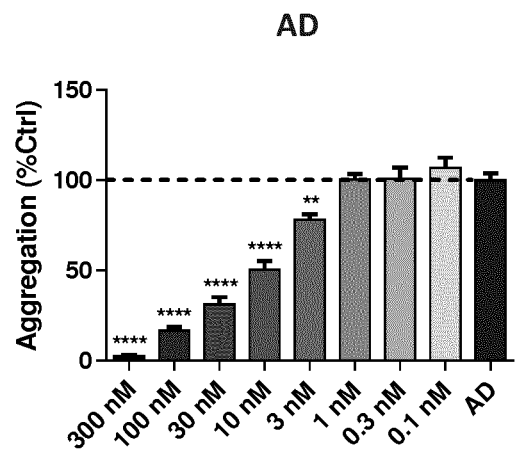
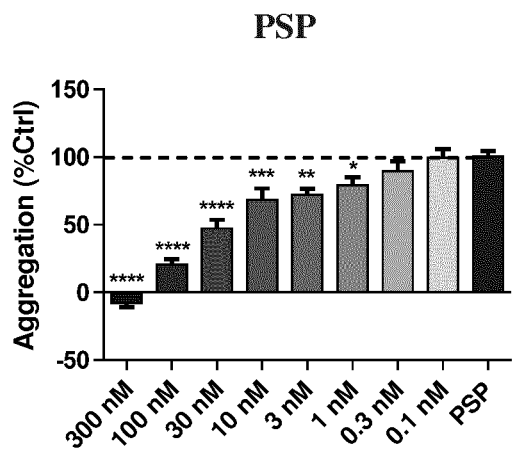
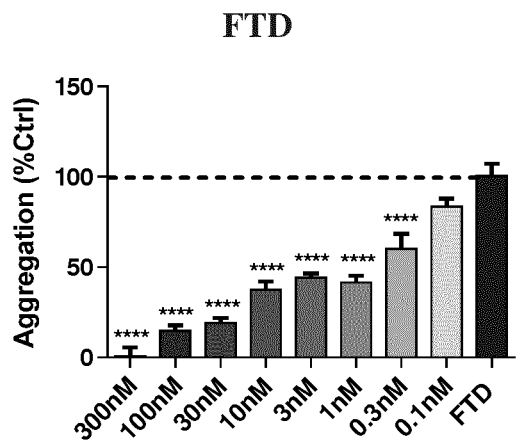

TAU-BINDING ANTIBODIES

CROSS-REFERENCE TO RELATED APPLICATION

This application is the U.S. national stage application of International Patent Application No. PCT/EP2016/065813, filed Jul. 5, 2016.

The Sequence Listing for this application is labeled "Seq-List.txt" which was created on Nov. 28, 2017 and is 134 KB. The entire content of the sequence listing is incorporated herein by reference in its entirety.

FIELD OF THE INVENTION

The present invention relates inter alia to therapeutic and diagnostic Tau-binding antibodies and binding fragments thereof, methods of making such antibodies and their use for treating and/or diagnosing tauopathies such as Alzheimer's disease; Amyotrophic lateral sclerosis/parkinsonism-dementia complex; Argyrophilic grain disease; Chronic traumatic encephalopathy; Corticobasal degeneration; Diffuse neurofibrillary tangles with calcification; Down syndrome; Familial British dementia; Familial Danish dementia; Frontotemporal dementia and parkinsonism linked to chromosome 17 caused by MAPT mutations; Gerstmann-Sträussler-Scheinker disease; Guadeloupean parkinsonism; Myotonic dystrophy; Neurodegeneration with brain iron accumulation; Niemann-Pick disease, type C; Non-Guamanian motor neuron disease with neurofibrillary tangles; Pick disease; Post-encephalitic parkinsonism; Prion protein cerebral amyloid angiopathy; Progressive subcortical gliosis; Progressive supranuclear palsy; SLC9A6-related mental retardation; Subacute sclerosing panencephalitis; Tangle-only dementia; White matter tauopathy with globular glial inclusions (Clavaguera et al. Brain Pathology 23 (2013) 342-349). The present invention also relates to methods of treating a human subject suffering from or being suspected to be prone to tauopathies described above, in particular tauopathies such as Alzheimer's disease and progressive supranuclear palsy.

BACKGROUND OF THE INVENTION

Alzheimer's disease (AD) and progressive supranuclear (PSP) are neurodegenerative diseases with high medical unmet needs, high cost for the societies' health systems, and high burden for the families affected. AD clinical signs include loss of memory, cognition, reasoning, judgment and emotional stability and ultimately death. PSP involves serious and progressive gait control and balance issues, falls, vertical eyes movement disturbances, cognitive problems, depression, apathy, and mild dementia. Late symptoms include blurring of vision, uncontrolled eye movement, slurred speech, difficulty swallowing and death.

For more than a decade AD disease modification programs have targeted the amyloid-beta-peptide through various mechanisms. In contrast, much less progress has been made in addressing intracellular Tau pathology, the second major hallmark for AD. Neurofibrillary inclusions or tangles containing aggregated, hyperphosphorylated Tau are defining characteristics of AD pathology and a number of other tauopathies, including PSP.

In these diseases there is a strong correlation between symptomatic progression and the level and distribution of intraneural Tau aggregates. In AD neuronal Tau tangles first appear in the transentorhinal cortex, from where they spread to the hippocampus and neocortex. The tangles observed in AD neurons consist of hyperphosphorylated, aggregated insoluble Tau. Direct toxic effects of the pathological Tau species and/or loss of axonal transport due to sequestration of functional Tau into hyperphosphorylated and aggregated forms, which are no longer capable of supporting axonal transport, have been proposed to contribute to the disease.

In its non-pathological state, Tau is a highly soluble cytoplasmic microtubule-binding protein, which occurs in the human central nervous system (CNS) in 6 main isoforms due to alternative splicing, ranging from 352 to 441 amino acids in length. These isoforms can have zero, one or two N-terminal inserts (0N, 1N, 2N), and either three or four C-terminal "repeat" sequences (3R or 4R). These 30-32 amino acid C-terminal repeat sequences, R1, R2, R3 and R4, together constitute the Tau microtubule-binding region (MTBR). Indeed the main role of Tau is believed to be in the assembly and stabilization of axonal microtubules. Microtubules form tracks for axonal transport and cytoskeletal elements for cell growth (Clavaguera et al., Brain Pathology 23 (2013) 342-349). Three Tau isoforms have been demonstrated to contain three microtubule binding regions (MTBR):

isoform 4, also referred to as 3R0N, NCBI Reference Sequence NP_058525.1 (352 amino acid),
isoform 7, also referred to as 3R1N, NCBI Reference Sequence NP_001190180.1 (381 amino acid)
isoform 8, also referred to as 3R2N, NCBI Reference Sequence NP_001190181.1 (410 amino acid).

Whereas the other three Tau isoforms contain four MTBRs:

isoform 2, also referred to as 4R2N, NCBI Reference Sequence NP_005901.2 (441 amino acid),
isoform 3, also referred to as 4R0N, NCBI Reference Sequence NP_058518.1 (383 amino acid), and
isoform 5, also referred to as 4R1N, NCBI Reference Sequence NP_001116539.1 (412 amino acid).

Only symptomatic treatments are currently available for these diseases with mild or no efficacy. No treatment is currently available for slowing or ideally stopping the development of the disease. Therefore there remains a need in the art for new compounds and compositions useful in the treatment of tauopathies.

Objectives and Summary of the Invention

It is an objective of the present invention to inter alia provide agents for treating or diagnosing tauopathies such as Alzheimer's disease (AD) or progressive supranuclear palsy (PSP). Further, it is an objective of the present invention to provide inter alia methods of treating or diagnosing tauopathies such as Alzheimer's disease (AD) or progressive supranuclear palsy (PSP).

These and other objectives as they will become apparent from the ensuing description hereinafter are attained by the subject matter of the independent claims. Some of the specific aspects and embodiments thereof contemplated by the present disclosure form the subject matter of the dependent claims. Yet other aspects and embodiments thereof as contemplated by the present disclosure may be taken from the ensuing description.

In a first aspect, the present disclosure provides an isolated Tau-binding antibody or binding fragment thereof, wherein said Tau-binding antibody or binding fragment thereof comprises a light chain variable region comprising a CDR1 selected from SEQ ID No.: 1 or sequences at least 90% identical thereto, a CDR2 selected from SEQ ID No.: 2 or sequences at least 90% identical thereto, and a CDR3 selected from SEQ ID No.: 3 or sequences at least 90% identical thereto; and/or a heavy chain variable region comprising a CDR1 selected from SEQ ID No.: 4 or sequences at least 90% identical thereto, a CDR2 selected from SEQ ID No.: 5 or sequences at least 90% identical thereto, and/or a CDR3 selected from SEQ ID No.: 6 or sequences at least 90% identical thereto.

In a second aspect, the present disclosure provides an isolated Tau-binding antibody or binding fragment thereof, wherein said Tau-binding antibody or binding fragment thereof comprises a light chain variable region comprising SEQ ID No.: 7 or sequences at least 80% identical thereto, and/or a heavy chain variable region comprising SEQ ID No.: 8 or sequences at least 80% identical thereto.

In a third aspect the present disclosure provides an isolated Tau-binding antibody or binding fragment thereof, wherein said Tau-binding antibody or binding fragment thereof comprises a light chain variable region comprising SEQ ID No.: 9 or sequences at least 80% identical thereto, and/or a heavy chain variable region comprising SEQ ID No.: 10 or sequences at least 80% identical thereto.

In a fourth aspect the present disclosure provides an isolated Tau-binding antibody or binding fragment thereof, wherein said Tau-binding antibody or binding fragment binds to an epitope comprising at least the amino acid residues of S238, A239, S241, T245, A246, of SEQ ID No.: 35.

As an embodiment of the first and fourth aspect, the disclosure provides for monoclonal antibodies or binding fragments thereof, which can be chimeric, humanized or fully human antibodies or binding fragments thereof.

As an embodiment of the second aspect, the disclosure provides for monoclonal antibodies or binding fragments thereof, which can be chimeric antibodies or binding fragments thereof.

As an embodiment of the third aspect, the disclosure provides for monoclonal antibodies or binding fragments thereof, which can be humanized antibodies or binding fragments thereof.

In a fifth aspect the present disclosure provides an isolated Tau-binding antibody or binding fragment thereof, wherein said Tau-binding antibody or binding fragment thereof competes for binding to Tau with a Tau-binding antibody or binding fragment thereof of any of the first to fourth aspects and the embodiments thereof.

In a sixth aspect the present disclosure provides an isolated Tau-binding antibody or binding fragment thereof, wherein said Tau-binding antibody or binding fragment thereof binds to substantially the same epitope of Tau as a Tau-binding antibody or binding fragment thereof of any of the first to fourth aspects and the embodiments thereof.

As an embodiment of the fifth and sixth aspect, the disclosure provides for monoclonal antibodies or binding fragments thereof, which can be humanized antibodies or binding fragments thereof.

Antibodies and binding fragments thereof of the first to sixth aspects and the embodiments thereof are capable of binding to soluble forms of human Tau, paired helical filaments (PHF) of human Tau or to both soluble forms of human Tau and paired helical filaments (PHF) of human Tau.

In a seventh aspect the present disclosure provides nucleic acid molecules comprising nucleic acid sequences such as DNA sequences coding for antibodies and binding fragments of the first to sixth aspects and the embodiments thereof.

In an eighth aspect the present disclosure provides cloning or expression vectors comprising these aforementioned nucleic acid molecules.

In a ninth aspect the present disclosure provides host cells comprising these afore mentioned nucleic acid molecules, cloning vectors or expression vectors.

In an tenth aspect the present disclosure provides methods of producing antibodies and binding fragments thereof of the first to sixth aspects and the embodiments thereof.

An eleventh aspect of the disclosure relates to the use of antibodies and binding fragments thereof of the first to sixth aspects and the embodiments thereof for treating tauopathies such as in particular AD and PSP.

Another aspect of the disclosure relates to the use of antibodies and binding fragments thereof of the first to sixth aspects and the embodiments thereof for diagnosing tauopathies such as in particular AD and PSP.

FIGURE LEGENDS

FIG. 1: A) depicts the donor VL of AB1 (VL_AB1) of SEQ ID No.: 7 with CDRs 1 (SEQ ID No.: 1), 2 (SEQ ID No.: 2) and 3 (SEQ ID No.: 3) being underlined. B) depicts the VL sequence of the human acceptor region IGKV2-29 of SEQ ID No.: 31 with acceptor CDRs 1, 2, and 3 being underlined. C) depicts the CDR grafted sequence gVL3_AB1 of SEQ No.: 9 with CDRs 1 (SEQ ID No.: 1), 2 (SEQ ID No.: 2) and 3 (SEQ ID No.: 3) being underlined.

FIG. 2: A) depicts the donor VH of AB1 (VH_AB1) of SEQ ID No.: 8 with CDRs 1 (SEQ ID No.: 4), 2 (SEQ ID No.: 36) and 3 (SEQ ID No.: 6) being underlined. B) depicts the VH sequence of the human acceptor region IGHV4-59 of SEQ ID No.: 32 with acceptor CDRs 1, 2, and 3 being underlined. C) depicts the CDR grafted sequence gVH17_AB1 of SEQ No.: 12 with CDRs 1 (SEQ ID No.: 4), 2 (SEQ ID No.: 37) and 3 (SEQ ID No.: 6) being underlined. Donor residues are shown in italic and highlighted: M48. Mutations in the framework are highlighted (E1). CDR2 comprises a S61A substitution compared to VH_AB1. D) depicts the CDR grafted sequence gVH18_AB1 of SEQ No.: 13 with CDRs 1 (SEQ ID No.: 4), 2 (SEQ ID No.: 38) and 3 (SEQ ID No.: 6) being underlined. Donor residues are shown in italic and highlighted (M48). Mutations in the framework are highlighted (E1). CDR2 comprises a S61T substitution compared to VH_AB1.

Figure 3:
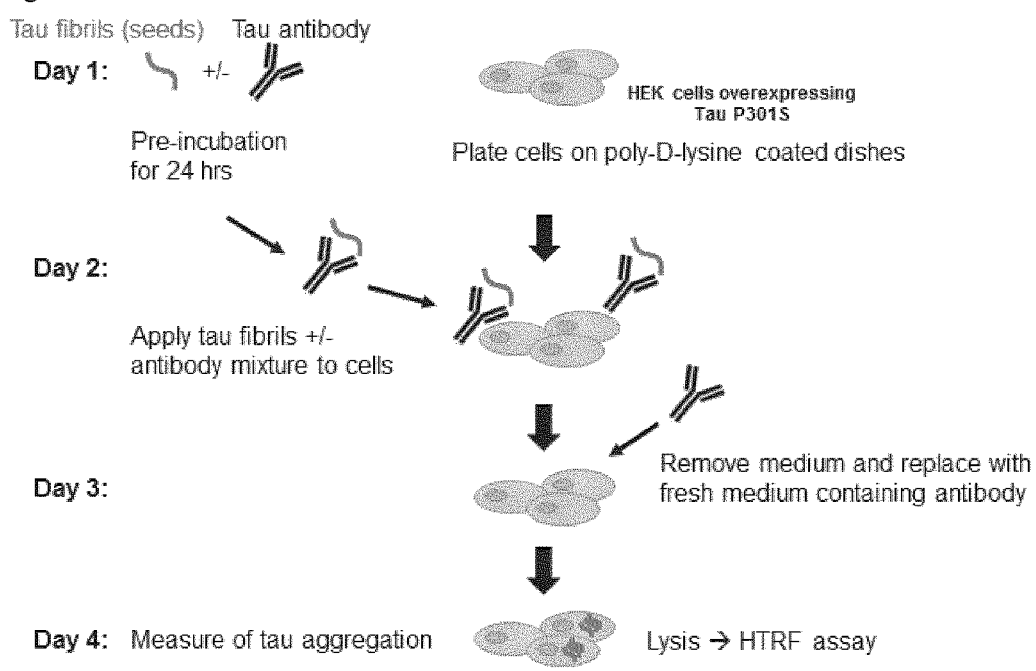

FIG. 3: Diagram illustrating the cellular aggregation assay of Experiment 3.1.

FIG. 4: Efficacy of Tau-binding antibodies having a light chain of SEQ ID No.: 14 and a heavy chain of SEQ ID No.:18 (A), and of a Tau-binding antibody having a light chain of SEQ ID No.: 14 and a heavy chain of SEQ ID No.:17 (B), or a negative control IgG4 antibody A33 (C) in a cellular Tau aggregation assay using human Tau pathological fibrils recovered from human AD patients (AD-PHF8) as seeds.

FIG. 5: Western blot showing binding properties of a Tau-binding antibody AB1 having VL of SEQ ID No.: 7 and VH of SEQ ID No.: 8 (A), and humanized antibodies having a light chain of SEQ ID No.: 14 and heavy chain of SEQ ID 17 (B), of a Tau-binding antibody having a light chain of SEQ ID No.: 14 and a heavy chain of SEQ ID No.:18 (C), to Tau recovered from fraction 8 samples from human AD, PSP or control patients. A33 antibody was used as a negative control.

Figure 6:
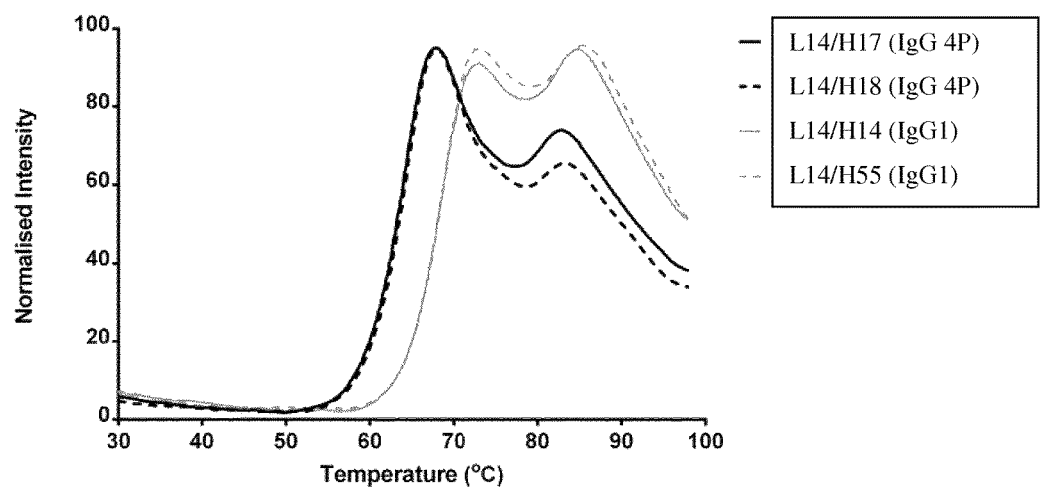

FIG. 6: Overlay of thermograms for Tau-binding antibody having a light chain of SEQ ID No.: 14 and heavy chain of SEQ ID 17, of a Tau-binding antibody having a light chain of SEQ ID No.: 14 and a heavy chain of SEQ ID No.:18, of a Tau-binding antibody having a light chain of SEQ ID No.: 14 and a heavy chain of SEQ ID No.:54, and of a Tau-binding antibody having a light chain of SEQ ID No.: 14 and a heavy chain of SEQ ID No.: 55.

FIG. 7: DNA construct encoding human Tau isoform 2 for *E. coli* expression (pET 6His TEV-hTau iso 2 (1-441)) (BioReg ID: D0003105) (SEQ ID No.: 39. BamHI/XhoI insert encoding amino acid sequence was sub-cloned into a modified pET32 vector cut with BamHI/XhoI. (6His-TEV-Tau coding sequence in bold italics).

FIG. 8: A) Expressed amino acid sequence from pET 6His TEV-hTau iso 2 (1-441) (SEQ ID No.: 40); B) final amino acid sequence expressed from pET 6His TEV-hTau iso 2 (1-441) after TEV cleavage (SEQ ID No.: 41).

FIG. 9: DNA construct encoding human Tau isoform 3 for *E. coli* expression (pET 6His TEV-hTau iso 3 (1-383)) (BioReg ID: D0003104) (SEQ ID No.: 42. BamHI/XhoI insert encoding amino acid sequence was sub-cloned into a modified pET32 vector cut with BamHI/XhoI. (6His-TEV-Tau coding sequence in bold italics).

FIG. 10: A) Expressed amino acid sequence from pET 6His TEV-hTau iso 3 (1-383) (SEQ ID No.: 43); B) final amino acid sequence expressed from pET 6His TEV-hTau iso 3 (1-383) after TEV cleavage (SEQ ID No.: 44).

FIG. 11: DNA construct encoding human Tau isoform 4 for *E. coli* expression (pET 6His TEV-hTau iso 4 (1-352)) (BioReg ID: D0003093) (SEQ ID No.: 45. BamHI/XhoI insert encoding amino acid sequence was sub-cloned into a modified pET32 vector cut with BamHI/XhoI. (6His-TEV-Tau coding sequence in bold italics).

FIG. 12: A) Expressed amino acid sequence from pET 6His TEV-hTau iso 4 (1-352) (SEQ ID No.: 46); B) final amino acid sequence expressed from pET 6His TEV-hTau iso 4 (1-352) after TEV cleavage (SEQ ID No.: 47).

FIG. 13: DNA construct encoding human Tau isoform 5 for *E. coli* expression (pET 6His TEV-hTau iso 5 (1-412)) (BioReg ID: D0003103) (SEQ ID No.: 48. BamHI/XhoI insert encoding amino acid sequence was sub-cloned into a modified pET32 vector cut with BamHI/XhoI. (6His-TEV-Tau coding sequence in bold italics).

FIG. 14: A) Expressed amino acid sequence from pET 6His TEV-hTau iso 5 (1-412) (SEQ ID No.: 49); B) final amino acid sequence expressed from pET 6His TEV-hTau iso 5 (1-412) after TEV cleavage (SEQ ID No.: 50).

FIG. 15: DNA construct encoding human Tau isoform 2 for expression in HEK293 cells (pMH-10His-TEV-hTau iso2 (1-441)) (BioReg ID: D0003109) (SEQ ID No.: 51. BamHI/XhoI insert encoding amino acid sequence was sub-cloned into mammalian expression vector pMH-10HisTEV cut with BamHI/XhoI. (10His-TEV-Tau coding sequence in bold italics, silent point mutation A1032T to remove restriction site underlined).

FIG. 16: A) Expressed amino acid sequence from pMH-10His-TEV-hTau iso2 (1-441) (SEQ ID No.: 52); B) final amino acid sequence expressed from pMH-10His-TEV-hTau iso2 (1-441) after TEV cleavage (SEQ ID No.: 53).

FIG. 17: Efficacy of Tau-binding antibodies having a light chain of SEQ ID NO: 14 and a heavy chain of SEQ ID NO: 18 in a cellular Tau aggregation assay using human Tau pathological fibrils recovered from human AD patients, or human PSP patients or human FTD patients as seeds.

DETAILED DESCRIPTION OF THE INVENTION

The present disclosure as illustratively described in the following may suitably be practiced in the absence of any element or elements, limitation or limitations, not specifically disclosed herein.

The present disclosure will be described with respect to particular aspects and embodiments thereof and with reference to certain figures and examples but the invention is not limited thereto but only by the claims.

Technical terms are used by their common sense unless indicated otherwise. If a specific meaning is conveyed to certain terms, definitions of terms will be given in the following in the context of which the terms are used.

Where the term "comprising" is used in the present description and claims, it does not exclude other elements. For the purposes of the present disclosure, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present disclosure, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. The terms "about" or "approximately" denote an interval of accuracy that the person skilled in the art will understand to still ensure the technical effect of the feature in question. The term typically indicates deviation from the indicated numerical value of ±10%, and preferably of ±5%.

It is to be understood that any reference to a Tau-binding antibody or binding fragment thereof as a preferred embodiment of the various aspects contemplates monoclonal Tau-binding antibodies or binding fragments thereof.

For various aspects the present disclosure mentions antibodies and binding fragments thereof comprising CDRs and variable regions of the respective light chain and/or heavy chain regions. Antibodies or binding fragments thereof comprising just a variable light chain region or variable heavy chain region may be useful e.g. for methods of manufacturing or e.g. for screening for variable regions that can effectively associate with a corresponding other variable region. It is, however, to be understood that wherever reference is made to antibodies and binding fragments thereof comprising CDRs and variable regions of the respective light chain and/or heavy chain regions, this always contemplates as a preferred embodiment antibodies and binding fragments thereof comprising CDRs and variable regions of the respective light chain and heavy chain regions.

As used herein, the terms "treatment", "treating" and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. Treatment thus covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A reference to a Tau-binding antibody or binding fragment thereof as "a therapeutically active agent" refers to the use of a Tau-binding antibody or binding fragment thereof in the treatment of a disease.

A "therapeutically effective amount" refers to the amount of a Tau-binding antibody or binding fragment thereof that, when administered to a mammal or other subject for treating a disease, is sufficient to effect such treatment for the disease. The therapeutically effective amount will vary depending on the Tau-binding antibody or binding fragment thereof, the disease and its severity and the age, weight, etc., of the subject to be treated.

A reference to a Tau-binding antibody or binding fragment thereof as "a diagnostically active agent" refers to the use of a Tau-binding antibody or binding fragment thereof in the diagnosis of a disease.

A "diagnostically effective amount" refers to the amount of a Tau-binding antibody or binding fragment thereof that, when used in a diagnostic test on a biological sample is sufficient to allow identification of a disease or of monitoring the amount of disease tissue as a means of monitoring the efficacy of therapeutic intervention.

The present application is based in part on the identification of an antibody designated AB1 that binds human Tau. As is customary in the field, Tau residue numbering in this text refers to Tau isoform 2 of SEQ ID No.: 35 (NCBI reference sequence: NP_005901.2). As will be laid out hereinafter AB1, which was isolated from an immunized rat, and recognizes an epitope comprising at least the amino acids residues of S238, A239, S241, T245, A246 of SEQ ID No.: 35. This region is just before the first MTBR repeat region present in all 6 isoforms of Tau that may be found in the central nervous system.

The examples establish that AB1 is capable of binding to both soluble forms of human Tau and paired helical filaments (PHF) of human Tau (see Example 2.3) and that AB1 was capable of detecting intraneuronal neurofibrillary tangles (NFT), extraneuronal NFT, neuritic plaque-like structures and neurophil threads in cryosections of human samples (see Example 3.2). In some of the assays and models tested AB1 displayed a lower IC50 than prior art antibodies. It seems reasonable to assume that this behavior is at least in part mediated by the complementarity determining regions (CDRs) of the variable light chain region (VL) and variable heavy chain region (VH) of AB1.

Against this background, the present disclosure provides for Tau-binding antibodies or binding fragments thereof comprising the CDRs or specificity determining residues of the VL region of AB1 (SEQ ID No.: 7) and/or the CDRs of the VH region of AB1 (SEQ ID No.: 8).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. However, according to Chothia (Chothia, C. and Lesk, A. M. J. Mol. Biol., 196, 901-917 (1987)) the loop equivalent to CDR-H1 extends from residue 26 to residue 32.

CDR1, CDR2, and CDR3 of VL of AB1 were thus identified to correspond to SEQ ID Nos.: 1, 2, and 3 respectively. CDR1, CDR2, and CDR3 of VH of AB1 were thus identified to correspond to SEQ ID Nos.: 4, 36, and 6 respectively. It is commonly known that one or more amino acid substitutions, additions and/or deletions may be made to the CDRs provided by the present disclosure invention without significantly altering the ability of the antibody to bind to Tau. The effect of any amino acid substitutions, additions and/or deletions can be readily tested by one skilled in the art, for example by using the methods described in the examples or known from the common general knowledge. In the originally identified CDR2 of VH (CDRH2), namely SEQ ID No.: 36, for example a potential asparagine deamidation site was identified and modified by replacing the contiguous Serine residue by either alanine or threonine. This lead to sequences SEQ ID No.: 37 and 38 respectively for CDRH2. For the sake of brevity the three sequences for CDRH2, namely SEQ ID Nos.: 36, 37, and 38 were combined as SEQ ID No.: 5.

It will be appreciated that further modifications such as substitutions, additions and/or deletions may be made to the CDRs without substantially changing e.g. the binding properties compared to AB1. This may be primarily achieved by e.g. replacing amino acids in the CDRs for similar amino acids. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Against this background the disclosure provides in one aspect for an isolated Tau-binding antibody or binding fragment thereof, wherein said Tau-binding antibody or binding fragment thereof comprises a light chain variable region comprising a CDR1 selected from SEQ ID No.: 1 or sequences at least 90% identical thereto, a CDR2 selected from SEQ ID No.: 2 or sequences at least 90% identical thereto, and a CDR3 selected from SEQ ID No.: 3 or sequences at least 90% identical thereto; and/or a heavy chain variable region comprising a CDR1 selected from SEQ ID No.: 4 or sequences at least 90% identical thereto, a CDR2 selected from SEQ ID No.: 5 or sequences at least 90% identical thereto, and/or a CDR3 selected from SEQ ID No.: 6 or sequences at least 90% identical thereto.

"Identity", as used herein, indicates that at any particular position in the aligned sequences, the amino acid residue is identical between the sequences. Degrees of identity can be readily calculated e.g. using the BLAST™ software available from NCBI (Altschul, S. F. et al., 1990, J. Mol. Biol. 215:403-410; Gish, W & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. K Madden, T. L. 1997, Genome Res. 7:649-656).

The identity of CDRL1, CDRL2, CDRL3, CDRH1, CDRH2, and CDRH3 to SEQ ID Nos.: 1, 2, 3, 4, 5, and 6 respectively may be at least 90%, but may also be higher such as at least 95%, 96%, 97%, 98% or 99% with an optional preference for higher identities. Positions of different identity may be selected according to similarity considerations.

In this context the disclosure specifically considers Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 5, and 6 respectively. The disclosure also considers Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 36, and 6 respectively, Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 37, and 6 respectively, and Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 38, and 6 respectively.

Tau-binding antibodies or binding fragments thereof as contemplated by said first aspect may comprise these CDRs embedded in framework regions of different origin. Thus, the CDRs may be comprised within the original framework regions of AB1, namely the rat VL region of SEQ ID No.: 7 and the rat VH region of SEQ ID No.: 8. However, the CDRs may also be embedded in framework regions of different species origin such as mice or human framework regions. Depending on the origin of framework regions and constant regions, which can be combined with such framework regions, one may obtain chimeric, humanized or fully human Tau-binding antibodies or binding fragments thereof.

Chimeric Tau-binding antibodies or binding fragments thereof will comprise the CDRs within framework regions of non-human origin combined with constant regions of human origin. Humanized Tau-binding antibodies or binding fragments thereof will comprise the CDRs within framework regions of human origin combined together with constant regions of human origin.

Against this background the disclosure provides in another aspect an isolated Tau-binding antibody or binding fragment thereof, wherein said Tau-binding antibody or binding fragment thereof comprises a light chain variable region comprising SEQ ID No.: 7 or sequences at least 80% identical thereto, and/or a heavy chain variable region comprising SEQ ID No.: 8 or sequences at least 80% identical thereto.

The identity of VL and VH to SEQ ID Nos.: 7 and 8 respectively may be at least 80%, but may also be higher such as at least 80%, 85%, 90%, 95%, 96%, 97%, 98% or 99% with an optional preference for higher identities. Positions of different identity may be selected according to similarity considerations. It will be appreciated that in term of identity there may be more flexibility for the framework regions vs. the CDRs.

In this context the disclosure specifically considers Tau-binding antibodies or binding fragments thereof comprising a VL of SEQ ID No.: 7 and a VH of SEQ ID No.: 8.

Humanized Tau-binding antibodies or binding fragments thereof are particularly contemplated by the present disclosure.

To this end the CDRs may be grafted onto human framework regions. It will be appreciated that identification of such humanized CDR-grafted Tau-binding antibody or binding fragment thereof may be achieved following established approaches of the art. When the CDRs or specificity determining residues are grafted, any appropriate acceptor human variable region framework sequence may be used having regard to the class/type of the donor antibody from which the CDRs are derived (see, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1).

Also, in a CDR-grafted antibody variable region of the present invention, the framework regions need not have exactly the same sequence as those of the acceptor antibody. CDRs may thus be grafted with or without framework changes. Introducing framework changes on the basis of a comparison between the framework regions of the donor variable regions and the acceptor framework regions may allow retaining e.g. the affinity of an antibody which otherwise may be reduced as a consequence of humanization. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. Residues for change may be selected using the protocol outlined by Adair et al. (1991) (Humanised antibodies. WO91/09967). In a CDR-grafted antibody of the present invention, the acceptor heavy and light chains do not necessarily need to be derived from the same antibody and may, if desired, comprise composite chains having framework regions derived from different chains.

Examples of human acceptor frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-ce.cam.ac.uk/ or see Worldwide Website: imgt.org). The present disclosure specifically considers to use the human V-region IGKV2-29 plus JK2 J-region of SEQ ID No.: 31 (IMGT, see Worldwide Website: imgt.org/) as an acceptor framework region for the light chain CDRs and the human V-region IGHV4-59 plus JH3 J-region SEQ ID No.: 32 (IMGT, see Worldwide Website: imgt.org/) as an acceptor framework region for the heavy chain CDRs. In SEQ ID No.: 32, positions 1 and 48 may e.g. be considered for residue changes in the framework regions. The glutamine residue in position 1 may be changed to glutamate or aspartate. The isoleucine residue in position 48 may be changed to methionine. Other positions in SEQ ID No.: 32 for residue changes in the framework regions may be positions 37 and/or 71. For example, the isoleucine residue in position 37 of SEQ ID NO: 32 may be changed to valine. The valine residue in position 71 may be changed to arginine. Positions in SEQ ID No.: 31 for residue changes in the framework regions may be position 68. The serine residue in position 68 of SEQ ID NO: 31 may be changed to isoleucine.

Against this background the disclosure provides in another aspect an isolated Tau-binding antibody or binding fragment thereof, wherein said Tau-binding antibody or binding fragment thereof comprises a light chain variable region comprising SEQ ID No.: 9 or sequences at least 80% identical thereto, and/or a heavy chain variable region comprising SEQ ID No.: 10 or sequences at least 80% identical thereto.

Such an isolated Tau-binding antibody or binding fragment thereof may comprise a light chain variable region comprising SEQ ID No.: 9 or sequences at least 80% identical thereto, and/or a heavy chain variable region comprising SEQ ID No.: 11, 12, 13 or sequences at least 80% identical thereto.

The identity of VL and VH to SEQ ID Nos.: 9 and 10 respectively may be at least 80%, but may also be higher such as at least 80%, 85%, 90%, 95%, 96%, 97%, 98% or 99% with an optional preference for higher identities. Positions of different identity may be selected according to similarity considerations. It will be appreciated that in term of identity there may be more flexibility for the framework regions vs. the CDRs.

In this context the application specifically considers Tau-binding antibodies or binding fragments thereof comprising a VL of SEQ ID No.: 9 and a VH of SEQ ID No.: 11, Tau-binding antibodies or binding fragments thereof comprising a VL of SEQ ID No.: 9 and a VH of SEQ ID No.: 12, and Tau-binding antibodies or binding fragments thereof comprising a VL of SEQ ID No.: 9 and a VH of SEQ ID No.: 13.

Humanized CDR grafted Tau-binding antibodies or binding fragments thereof may comprise constant regions of human origin. Depending on the amino acid sequence of the constant region of their heavy chains, antibodies or immunoglobulins are divided into the classes: IgA, IgD, IgE, IgG and IgM, and several of these may be further divided into subclasses (subtypes), e.g. IgG1, IgG2, IgG3, and IgG4, IgA1, and IgA2. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. The present disclosure specifically considers humanized antibodies of the IgG1 and IgG4 subtype.

It will be appreciated that sequence amendments of these constant region domains may also be used. For example one or more amino acid, such as 1 or 2 amino acid substitutions, additions and/or deletions may also be made to the antibody constant domains without significantly altering the ability of the antibody to bind to Tau. IgG4 molecules in which the serine at position 241 has been changed to proline as described in Angal et al; Molecular Immunology, 1993, 30 (I), 105-108 may be used as well.

Antibody effector functions include ADCC and CDC. ADCC refers to antibody-dependent cellular cytotoxicity. In order to determine whether an antibody is in principle capable of mediating ADDC, ADCC may be measured in vitro by e.g. so-called $Cr^{51}$, Eu, and $S^{35}$-release assays. A target cell containing the antigen of interest, i.e. Tau may be labeled with these compounds. After binding of the therapeutic antibody, the cells are washed and effector cells expressing Fc receptors such as FcγRIII are co incubated with the antibody-labeled target cells and lysis of the target cells can be monitored by release of the labels. Another approach uses the so-called aCella TOX™ assay. CDC refers to complement-dependent cellular cytotoxicity. In order to determine whether an antibody is in principle capable of mediating CDC, CDC may be measured in vitro as described e.g. in Delobel A et al, Methods Mol Biol. (2013); 988:115-43 or Current Protocols in Immunology, Chapter 13 Complement (Print ISSN: 1934-3671).

Against this background the disclosure provides in another aspect an isolated Tau-binding antibody or binding fragment thereof, wherein said Tau-binding antibody or binding fragment thereof comprises a light chain comprising SEQ ID No.: 14 or sequences at least 70% identical thereto, and/or a heavy chain comprising SEQ ID No.: 15 or sequences at least 70% identical thereto.

Such an isolated Tau-binding antibody or binding fragment thereof may comprise a light chain comprising SEQ ID No.: 14 or sequences at least 70% identical thereto, and/or a heavy chain comprising SEQ ID No.: 16, 17, 18 or sequences at least 70% identical thereto.

The identity of the light chain and heavy chain to SEQ ID Nos.: 14 and 15 respectively may be at least 70%, but may also be higher such as at least 70%, 75%, 80%, 85%, 90%, 95%, 96%, 97%, 98% or 99% with an optional preference for higher identities. Positions of different identity may be selected according to similarity considerations. It will be appreciated that in terms of identity there may be more flexibility for the framework regions vs. the CDRs and even more flexibility for the constant regions.

In this context the application specifically considers Tau-binding antibodies or binding fragments thereof comprising a light chain of SEQ ID No.: 14 and a heavy chain of SEQ ID No.: 16, Tau-binding antibodies or binding fragments thereof comprising a light chain of SEQ ID No.: 14 and a heavy chain of SEQ ID No.: 17, and Tau-binding antibodies or binding fragments thereof comprising a light chain of SEQ ID No.: 14 and a heavy chain of SEQ ID No.: 18.

Furthermore, the disclosure provides in another aspect an isolated Tau-binding antibody or binding fragment thereof, wherein said Tau-binding antibody or binding fragment thereof comprises a light chain comprising SEQ ID No.: 14 or sequences at least 70% identical thereto, and/or a heavy chain comprising SEQ ID No.: 54 or SEQ ID No.: 55 or sequences at least 70% identical thereto.

The identity of the light chain and heavy chain to SEQ ID No.: 14 and SEQ ID Nos.: 54 or 55, respectively may be at least 70%, but may also be higher such as at least 70%, 75%, 80%, 85%, 90%, 95%, 96%, 97%, 98% or 99% with an optional preference for higher identities. Positions of different identity may be selected according to similarity considerations. It will be appreciated that in terms of identity there may be more flexibility for the framework regions vs. the CDRs and even more flexibility for the constant regions.

Also provided by the present disclosure is a specific region or epitope of human Tau which is bound by an antibody or binding fragment thereof provided by the present disclosure, in particular an antibody or binding fragment thereof comprising any one of CDR-H1 (SEQ ID No.:4), CDR-H2 (SEQ ID No.:5), CDR-H3 (SEQ ID No.:6), CDR-L1 (SEQ ID No.:1), CDR-L2 (SEQ ID No.:2) or CDR-L3 (SEQ ID No.:3), for example antibodies comprising the VL of SEQ ID No.: 7 and the VL of SEQ ID No.: 8.

Further provided by the present disclosure is a specific region or epitope of human Tau, in particular an epitope within amino acids 235-250 of SEQ ID NO.: 35, which is bound by an antibody or binding fragment thereof provided in the present disclosure, in particular an antibody or binding fragment thereof comprising the VL of SEQ ID No.: 7 and the VL of SEQ ID No.: 8.

This specific region or epitope of Tau can be identified by any suitable epitope mapping method known in the art in combination with any one of the antibodies provided by the present disclosure. Examples of such methods include screening peptides of varying lengths derived from SEQ ID No.: 35 for binding to the Tau-binding antibodies or binding fragments thereof of the present disclosure with the smallest fragment that can specifically bind to the antibody containing the sequence of the epitope recognized by the Tau-binding antibodies or binding fragments thereof. Given the existence of different Tau isoforms in the central nervous system, it is to be understood that any such isoform may be used in the methods detailed herein. In a specific example the longest isoform of Tau may be used, i.e. isoform 2 as defined in SEQ ID No.: 35. The Tau peptides of SEQ ID No.: 35 may be produced recombinantly, synthetically or by proteolytic digestion of the Tau polypeptide. Peptides that bind the antibody can be identified by, for example, Western Blot or mass spectrometric analysis. In another example, NMR spectroscopy or X-ray crystallography can be used to identify the epitope bound by a Tau-binding antibody or binding fragment thereof. Once identified, the epitopic fragment which binds an antibody of the present invention can be used, if required, as an immunogen to obtain additional antibodies which bind the same epitope. Furthermore, the epitopic fragment which binds an antibody of the present invention can be used to obtain proteins that bind to the same epitope and, if required, inhibit at least one biological activity of Tau, such as protein or polypeptide compounds comprising more than 10 amino acids that are based on protein scaffolds e.g. from lipocalin ("anticalins"), fibronectin ("adnectins", trinectins), kunitz domains, C-type lectin, transferrin, gamma-crystalline, cysteine-nots, ankyrin repeats ("DARPins") or protein A, ("affibodies") as known in the art (Tomlinson, 2004; Mosavi et al., 2004; Gill and Damle, 2006; Nilsson and Tolmachev, 2007; Binz et al., 2004). Additionally, molecules that bind the same epitope include further organic molecules including peptides and cyclic peptides comprising not more than 10 amino acids as well as peptidomimetics. Peptidomimetics are compounds that are based on the amino acid sequences found at protein-protein interaction sites and are known in the art (Sillerud and Larson, 2005).

Against this background the disclosure provides in another aspect an isolated Tau-binding antibody or binding fragment thereof, wherein said Tau-binding antibody or binding fragment thereof binds to an epitope comprising at least the amino acid residues of S238, A239, S241, T245, A246 of SEQ ID No.: 35. The overall epitope seems to extend from amino acids 232 to 251 of SEQ ID No.: 35. In one example the epitope of human Tau bound by an antibody of the present invention comprises amino acids S238, A239, S241, T245, A246 and one or more residues selected from S235, S237, K240, R242, L243, Q244, V248, and M250 of SEQ ID No.: 35.

In another aspect the present disclosure provides an isolated Tau-binding antibody or binding fragment thereof wherein said Tau-binding antibody or binding fragment thereof binds to an epitope comprising at least the amino acid residues of S235, S238, A239, K240, S241, Q244, T245, and A246 of SEQ ID No.: 35. In one example the epitope of human Tau bound by an antibody of the present invention comprises amino acids S235, S238, A239, K240, S241, Q244, T245, A246 and one or more residues selected from S237, R242, L243, V248, and M250 of SEQ ID No.: 35.

In another aspect the present disclosure provides an isolated Tau-binding antibody or binding fragment thereof wherein said Tau-binding antibody or binding fragment thereof binds to an epitope comprising at least the amino acid residues of S235, S237, S238, A239, K240, S241, Q244, T245, and A246 of SEQ ID No.: 35. In one example the epitope of human Tau bound by an antibody of the present invention comprises amino acids S235, S237, S238, A239, K240, S241, Q244, T245, A246, and one or more residues selected from R242, L243, V248, and M250 of SEQ ID No.: 35.

In one example, the epitope of human Tau bound by an antibody of the present invention comprises amino acid residues S235, S237, S238, A239, K240, S241, R242, L243, Q244, T245, A246, V248, and M250 of SEQ ID No.: 35.

Tau-binding antibodies or binding fragments thereof comprising a VL of SEQ ID No.: 7 and a VH of SEQ ID No.: 8 are representatives of Tau-binding antibodies or binding fragments thereof binding to the afore-mentioned epitopes.

Such antibodies can be chimeric, humanized or fully human monoclonal antibodies or can be used to obtain chimeric, humanized or fully human monoclonal antibodies.

In another aspect the present disclosure provides an isolated neutralizing Tau-binding antibody or binding fragment thereof, wherein said neutralizing Tau-binding antibody or binding fragment thereof binds an epitope of Tau comprising amino acid residues S238, A239, S241, T245, A246 of SEQ ID No.: 35. In one example the epitope of human Tau bound by a neutralising antibody of the present invention comprises amino acids S238, A239, S241, T245, A246 and one or more residues selected from S235, S237, K240, R242, L243, Q244, V248, and M250 of SEQ ID No.: 35.

In another aspect the present disclosure provides an isolated neutralizing Tau-binding antibody or binding fragment thereof wherein said neutralizing Tau-binding antibody or binding fragment thereof binds to an epitope comprising at least the amino acid residues of S235, S238, A239, K240, S241, Q244, T245, and A246 of SEQ ID No.: 35. In one example the epitope of human Tau bound by a neutralising antibody of the present invention comprises amino acids S235, S238, A239, K240, S241, Q244, T245, and A246 and one or more residues selected from S237, 8242, L243, V248, and M250 of SEQ ID No.: 35.

In another aspect the present disclosure provides an isolated neutralizing Tau-binding antibody or binding fragment thereof wherein said neutralizing Tau-binding antibody or binding fragment thereof binds to an epitope comprising at least the amino acid residues of S235, S237, S238, A239, K240, S241, Q244, T245, and A246 of SEQ ID No.: 35. In one example the epitope of human Tau bound by a neutralizing antibody of the present invention comprises amino acids S235, S237, S238, A239, K240, S241, Q244, T245, A246, and one or more residues selected from 8242, L243, V248 and M250 of SEQ ID No.: 35.

In one example, the epitope of human Tau bound by a neutralizing antibody of the present invention comprises amino acid residues S235, S237, S238, A239, K240, S241, R242, L243, Q244, T245, A246, V248, and M250 of SEQ ID No.: 35.

Tau-binding antibodies or binding fragments thereof comprising a VL of SEQ ID No.: 7 and a VH of SEQ ID No.: 8 are representatives of neutralizing Tau-binding antibodies or binding fragments thereof binding to the afore-mentioned epitopes.

Such neutralizing antibodies can be chimeric, humanized or fully human monoclonal antibodies or can be used to obtain chimeric, humanized or fully human monoclonal antibodies.

In another aspect the present disclosure provides an isolated Tau-binding antibody or binding fragment thereof, wherein said Tau-binding antibody or binding fragment thereof binds to substantially the same epitope of Tau as a Tau-binding antibody or binding fragment thereof described above. Binding to the epitope may be determined as described for epitope mapping using e.g. a Tau-binding antibody or binding fragment thereof comprising a VL of SEQ ID No.: 7 and a VH of SEQ ID No.: 8 as reference.

Such antibodies can be chimeric, humanized or fully human monoclonal antibodies or can be used to obtain chimeric, humanized or fully human monoclonal antibodies.

Also provided by the present disclosure is a Tau-binding antibody or binding fragment thereof that specifically binds to a region or epitope of human Tau, in particular an epitope within amino acids 235-250 of SEQ ID NO.: 35, as determined by heteronuclear single quantum coherence nuclear magnetic resonance (HSQC NMR).

Such antibodies can be chimeric, humanized or fully human monoclonal antibodies or can be used to obtain chimeric, humanized or fully human monoclonal antibodies.

In another aspect the present disclosure provides an isolated Tau-binding antibody or binding fragment thereof, wherein said Tau-binding antibody or binding fragment thereof competes for binding to Tau with a Tau-binding antibody described above.

In this context the disclosure specifically contemplates an isolated Tau-binding antibody or binding fragment thereof, wherein said Tau-binding antibody or binding fragment thereof competes for binding to Tau with a Tau-binding antibody or binding fragment thereof comprising a VL of SEQ ID No.: 7 and a VH of SEQ ID No.: 8.

Such antibodies can be chimeric, humanized or fully human monoclonal antibodies or can be used to obtain chimeric, humanized or fully human monoclonal antibodies.

Competition for binding to Tau can be determined by a reduction in binding of the antibody or binding fragment thereof to Tau by at least about 50%, or at least about 70%, or at least about 80%, or at least about 90%, or at least about 95%, or at least about 99% or about 100% in the presence of the reference antibody or binding fragment thereof which may comprise a VL of SEQ ID No.: 7 and a VH of SEQ ID No.: 8. Binding may be measured using surface Plasmon resonance using BIAcore® equipment, various fluorescence detection technologies (e.g. Fluorescence correlation spectroscopy, fluorescence cross-correlation, Fluorescence Lifetime measurements etc.) or various types of radioimmunoassays or other assays used to follow antibody binding to a target molecule.

The term "Tau-binding antibody or binding fragment thereof" means that the antibody or binding fragments thereof binds specifically to Tau by way of its variable regions, i.e. binds the Tau antigen with greater affinity than other antigens which are not homologues of Tau. The "Tau-binding antibody or binding fragment thereof" binds to Tau b way of its variable regions with at least twice, at least five times, at least 10, 20, 100, $10^3$, $10^4$, $10^5$ or at least $10^6$ times the affinity than other antigens which are not homologues of Tau. It will be understood that Tau-binding antibodies and binding fragments thereof may nevertheless also interact with other proteins (for example, S. aureus protein A or other antibodies in ELISA techniques) through interactions with sequences outside the variable region of the Tau-binding antibodies and binding fragments thereof. Such latter binding properties which are mediated by sequences outside the variable regions of the Tau-binding antibodies and binding fragments thereof and in particular by the constant regions of the Tau-binding antibodies and binding fragments thereof are not meant to be encompassed by the term "Tau-binding antibody or binding fragment thereof". Screening assays to determine binding specificity of an antibody are well known and routinely practiced in the art. Tau-binding antibodies or binding fragments thereof may have an equilibrium dissociation constant ($K_D$) for the affinity of the binding of the antibody (or the binding fragment thereof) to its antigen in the nanomolar range. Thus the $K_D$ may be below about $1*10^{-6}$, e.g. about below $5*10^{-7}$ such as about $2*10^{-7}$ or lower and can be measured using e.g. surface plasmon resonance and the BIAcore device as described in the examples.

As mentioned above, the present disclosure provides Tau-binding antibodies or binding fragments thereof. A full-length antibody includes a constant domain and a variable region. The constant region may not need to be present in its full length in an antigen binding fragment of an antibody. It is, however, to be understood that wherever the application considers the use of antibodies mediating ADCC and/or CDC, a binding fragment must comprise a constant region of sufficient length to be still capable of mediating ADCC and/or CDC.

As mentioned above, the present disclosure also refers to human Tau-binding antibodies or binding fragments thereof, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art (Lonberg, 2005; Green, 1999; Kellermann and Green, 2002; Nicholson et al., 1999). Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. Other methods for obtaining human antibodies antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art (Winter et al., 1994; Hoogenboom, 2002; Kretzschmar and von Ruden, 2002; Groves and Osbourn, 2005; Dufner et al., 2006).

Human antibodies may also be generated from isolated human B cells that are ex vivo immunized with an antigen of interest and subsequently fused to generate hybridomas which can then be screened for the optimal human antibody (Grasso et al., 2004; Li et al., 2006). The term "Tau-binding antibody" or binding fragment thereof as used herein refers to an antibody or binding fragment thereof that binds to and inhibits at least one biological activity of Tau. Biological activities of Tau are known in the art and include but are not limited to the aggregation of Tau molecules forming different types of aggregates such as tangles or fibrils described above. In a particular embodiment a "neutralizing Tau-binding antibody" or binding fragment thereof as used herein refers to an antibody or binding fragment thereof that binds and inhibits Tau aggregation in an in vitro assay, such as for example in an in vitro assay such as described in experiment 3.1 below.

The term 'antibody' as used herein generally relates to intact (whole, full-length) antibodies i.e. comprising the elements of two heavy chains and two light chains. The antibody may comprise further additional binding domains, for example as per the molecule DVD-Ig as disclosed in WO 2007/024715, or the so-called (FabFv)2Fc described in WO2011/030107. Thus antibody as employed herein includes bi, tri or tetra-valent full length antibodies.

Binding fragments of antibodies include single chain antibodies (i.e. a full length heavy chain and light chain); Fab, modified Fab, Fab', modified Fab', F(ab')$_2$, Fv, Fab-Fv, Fab-dsFv, Fab-scFv, Fab-scFc, disulphide stabilized Fab-scFv, single domain antibodies (e.g. VH or VL or VHH), scFv, scFv-scFc, dsscFv, dsscFv-scFc, bi, tri or tetra-valent antibodies, Bis-scFv, diabodies, tribodies, triabodies, tetrabodies, domain antibodies (dAbs), such as sdAbs, VHH and VNAR fragments, and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilised versions thereof, the Fab-dsFv was first disclosed in WO2010/035012. A disulphide stabilized form of Fab-scFv was described in WO2013/068571. Antibody formats comprising scFc formats were first described in WO2008/012543. Other antibody fragments for use in the present invention include the Fab and Fab' fragments described in International patent applications WO2005/003169, WO2005/003170 and WO2005/003171.

Multi-valent antibodies may comprise multiple specificities e.g. bispecific or may be monospecific (see for example WO92/22583 and WO05/113605). One such example of the latter is a Tri-Fab (or TFM) as described in WO92/22583.

In one embodiment there is provided a Fab fragment.

In one embodiment there is provided a Fab' fragment.

A typical Fab' molecule comprises a heavy and a light chain pair in which the heavy chain comprises a variable region VH, a constant domain CH1 and a natural or modified hinge region and the light chain comprises a variable region VL and a constant domain CL. In one embodiment there is provided a dimer of a Fab' according to the present disclosure to create a F(ab')2 for example dimerisation may be through the hinge.

In one embodiment the antibody or binding fragment thereof comprises a binding domain. A binding domain will generally comprise 6 CDRs, three from a heavy chain and three from a light chain. In one embodiment the CDRs are in a framework and together form a variable region. Thus in one embodiment an antibody or binding fragment comprises a binding domain specific for antigen comprising a light chain variable region and a heavy chain variable region.

It will be appreciated that the affinity of Tau-binding antibodies or binding fragments thereof provided by the present disclosure may be altered using suitable methods known in the art. The present disclosure therefore also relates to variants of the antibody molecules of the present invention, which have an improved affinity for Tau. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The Tau-binding antibodies and binding fragments thereof may thus also encompass any of the e.g. foregoing specifically mentioned amino acid sequences of the light or heavy chains with one or more conservative substitutions (e.g., 1, 2, 3, 4, 5, 6, 7, 8, 9, 10, 11, 12, 13, 14, or 15 conservative substitutions). One can determine the positions of an amino acid sequence that are candidates for conservative substitutions, and one can select synthetic and naturally-occurring amino acids that effect conservative substitutions for any particular amino acids. Consideration for selecting conservative substitutions include the context in which any particular amino acid substitution is made, the hydrophobicity or polarity of the side-chain, the general size of the side chain, and the pK value of side-chains with acidic or basic character under physiological conditions. For example, lysine, arginine, and histidine are often suitably substituted for each other. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. Other groups of amino acids frequently suitably substituted for each other include, but are not limited to, the group consisting of glutamic and aspartic acids; the group consisting of phenylalanine, tyrosine, and tryptophan; and the group consisting of serine, threonine, and, optionally, tyrosine.

The Tau-binding antibodies and binding fragments thereof as they are mentioned in the context of the present invention may encompass derivatives of the exemplary antibodies, fragments and sequences disclosed herein. "Derivatives" include Tau-binding antibodies and binding fragments thereof, which have been chemically modified. Examples of chemical modification include covalent attachment of one or more polymers, such as water soluble polymers, N-linked, or O-linked carbohydrates, sugars, phosphates, and/or other such molecules such as detectable labels such as fluorophores.

If desired a Tau-binding antibody or binding fragment thereof for use in the present invention may thus be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al, 1999, Pharmacology and Therapeutics, 83, 67-123). These techniques for conjugating effector molecules may include site specific conjugation or non-site specific or random conjugation. Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745. Alternatively, a particular attachment site for the effector molecule may be engineered into the antibody or antigen binding fragment thereof of the invention, for example as described in WO 2008/038024. Furthermore a coupling agent may be used to link the effector molecule to the antibody or antigen binding fragment thereof of the invention, for example as described in WO 2005/113605. It will be understood by the skilled artisan that the above recited possibilities may be used by themselves or in combination.

The term effector molecule as used herein includes, for example, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. The effector molecule as used herein also includes therapeutic agents such as chemotherapeutic agents, therapeutic polypeptides, nanoparticles, liposomes or therapeutic nucleic acids.

Other effector molecules may include chelated radionuclides such as $^{111}$In and $^{90}$Y, $Lu^{177}$, $Bismuth^{213}$, $Californium^{252}$, $Ifidium^{192}$ and $Tungsten^{188}/Rhenium^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *Pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-I), interleukin-2 (IL-2), granulocyte macrophage colony stimulating factor (GM-CSF), granulocyte colony stimulating factor (G-CSF), nerve growth factor (NGF) or other growth factor and immunoglobulins, or other protein or polypeptide compounds comprising more than 10 amino acids that are based on protein scaffolds e.g. from lipocalin ("anticalins"), fibronectin ("adnectins", trinectins), kunitz domains, C-type lectin, transferrin, gamma-crystalline, cysteine-nots, ankyrin repeats ("DARPins"), Fyn SH3 domains ("fynomers") or protein A ("affibodies") as known in the art (Tomlinson, 2004; Mosavi et al., 2004; Gill and Damle, 2006; Nilsson and Tolmachev, 2007; Binz et al., 2004; Silacci et al. 2014).

Other effector molecules include peptides and proteins that enhance or facilitate blood-brain barrier penetration. For example, WO2010/043047, WO2010/063122, WO2010/063123 or WO2011/041897 describe peptide or polypeptides that may act as a vector capable of transporting a therapeutic molecule across the blood-brain barrier and method of conjugating them to a therapeutic molecule. Peptides and proteins of interest in the context of blood-brain barrier penetration include, but are not limited to, peptides and proteins that bind to a blood brain barrier receptor such as transferrin receptor, glucose receptor, insulin receptor, insulin-like growth factor receptor, low density lipoprotein receptor-related protein 8, low density lipoprotein receptor-related protein 1 and heparin-binding epidermal growth factor-like growth factor. Alternatively the effector molecule is an antibody fragment such as a domain antibody, camelid antibody or shark derived antibody (VNAR) that specifically binds to one of the above blood-brain barrier receptors.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals such as may be used in positron emission tomography or single-photon emission computed tomography, and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{124}$I $^{125}$I, $^{131}$I, $^{111}$In, $^{99}$Tc, $^{89}$Zr, $^{90}$Y, $^{64}$Cu, $^{68}$Ga and $^{18}$F. A particular type of effector molecules suitable as detectable substances useful for diagnosis include electron-deficient tetrazines and trans-cyclooctene (TCO) as described in Wyffels et al. 2014, Nuclear Medicine and biology 41 (2014):513-523, where a Tau-binding antibody of the invention linked to tetrazine may be administered and allowed to reach maximum uptake and sufficient clearance from non target sites, followed by subsequent administration of TCO or an optimized TCO analog labeled with a suitable radioactive nuclide, such that the TCO will covalently bind the tetrazine on the Tau-binding antibody of the invention, and allow its detection for example by positron emission tomography or single-photon emission computed tomography.

In one embodiment there is provided a Tau-binding Fab, Fab', or scFv linked to a radioactive nuclide or to tetrazine. Linkages to a radioactive nuclide or to tetrazine may be made via attachment through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971, WO2008/038024). In one example the Tau-binding antibody or binding fragment thereof of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. In one embodiment if the radionuclide is a metal ion such as $^{111}$In, $^{99}$Tc, $^{89}$Zr, $^{90}$Y, $^{64}$Cu, or $^{68}$Ga this may be bound by a macrocyle chelator for example as described by Turner et al. (Br. J. Cancer, 1994, 70:35-41; *Comparative biodistribution of indium-111-labelled macrocycle chimeric B72.3 antibody conjugates in tumour-bearing mice*) whereby the latter is in turn covalently linked to the aforementioned amino acid side-chain or terminal amino acid functional group or groups of the antibody or antibody fragment. In a further embodiment the latter macrocycle chelate with bound radionuclide may be the effector molecule described in WO05/113605 which is part of a cross linker that links two or more anti-Tau antibodies or fragments thereof.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, and albumin binding proteins or albumin binding compounds such as those described in WO05/117984.

Where such an effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as the brain or extend circulating half-life (for review see Chapman, 2002, Advanced Drug Delivery Reviews, 54, 531-545). Thus, for example, where the product is intended to leave the circulation and penetrate tissue.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is a Tau-binding antibody or binding fragment thereof and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971, WO2008/038024). In one example the Tau-binding antibody or binding fragment thereof of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In another aspect, the present disclosure provides nucleic acid molecules comprising nucleic acid sequences encoding for Tau-binding antibodies and binding fragments thereof, to nucleic acid molecules comprising nucleic acid sequences encoding for the variable light and/or heavy chains thereof and to nucleic acid molecules comprising nucleic acid sequences encoding for the CDR1, CDR2 and/or CDR3 of the variable light and/or heavy chains thereof.

By way of example, the VL of AB1 (SEQ ID No.: 7) may be encoded by SEQ ID No.: 19). The VH of AB1 (SEQ ID No.: 8) may be encoded by SEQ ID No.: 20).

The humanized VL of SEQ ID No.: 9 may be encoded by SEQ ID No.: 21. The humanized VH of SEQ ID No.: 12 may be encoded by SEQ ID No.: 22 and the humanized VH of SEQ ID No.: 13 may be encoded by SEQ ID No.: 23.

The humanized light chain of SEQ ID No.: 14 may be encoded by SEQ ID No.: 24. The humanized heavy chain of SEQ ID No.: 17 may be encoded by SEQ ID No.: 25 and the humanized heavy chain of SEQ ID No.: 18 may be encoded by SEQ ID No.: 26. The humanized heavy chain of SEQ ID No.: 54 may be encoded by SEQ ID No.: 56 and the humanized heavy chain of SEQ ID No.: 55 may be encoded by SEQ ID No.: 57.

The Tau-binding antibodies and binding fragments thereof may be encoded by a single nucleic acid (e.g., a single nucleic acid comprising nucleotide sequences that encode the light and heavy chain polypeptides of the antibody), or by two or more separate nucleic acids, each of which encode a different part of the antibody or antibody fragment. In this regard, the disclosure provides one or more nucleic acids that encode any of the forgoing antibodies, or binding fragments. The nucleic acid molecules may be DNA, cDNA, RNA and the like.

For example, DNA sequences coding for part or all of the antibody heavy and light chains may be synthesized as desired from the determined DNA sequences or on the basis of the corresponding amino acid sequences. DNA coding for acceptor framework sequences is widely available to those skilled in the art and can be readily synthesized on the basis of their known amino acid sequences.

Standard techniques of molecular biology may be used to prepare DNA sequences coding for the antibody molecule of the present invention. Desired DNA sequences may be synthesized completely or in part using oligonucleotide synthesis techniques. Site-directed mutagenesis and polymerase chain reaction (PCR) techniques may be used as appropriate.

Preferably, the encoding nucleic acid sequences are operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

The present disclosure in a further aspect thus provides cloning or expression vectors comprising such nucleic acid sequences encoding for Tau-binding antibodies and binding fragments thereof.

A "vector" is any molecule or composition that has the ability to carry a nucleic acid sequence into a suitable host cell where e.g. synthesis of the encoded polypeptide can take place. Typically and preferably, a vector is a nucleic acid that has been engineered, using recombinant DNA techniques that are known in the art, to incorporate a desired nucleic acid sequence (e.g., a nucleic acid of the invention). Expression vectors typically contain one or more of the following components (if they are not already provided by the nucleic acid molecules): a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element.

Vectors are typically selected to be functional in the host cell in which the vector will be used (the vector is compatible with the host cell machinery such that amplification of the gene and/or expression of the gene can occur).

The present disclosure in a further aspect thus provides host cells comprising cloning or expression vectors as described above and/or nucleic acid sequences encoding for Tau-binding antibodies and binding fragments thereof as described above.

The host cell can be any type of cell capable of being transformed with the nucleic acid or vector so as to produce a Tau-binding antibody or binding fragment thereof encoded thereby. The host cell comprising the nucleic acid or vector can be used to produce the Tau-binding antibody or binding fragment thereof, or a portion thereof (e.g., a heavy chain sequence, or a light chain sequence encoded by the nucleic acid or vector). After introducing the nucleic acid or vector into the cell, the cell is cultured under conditions suitable for expression of the encoded sequence. The antibody, antigen binding fragment, or portion of the antibody then can be isolated from the cell.

The host cells may be prokaryotic host cells (such as *E. coli*) or eukaryotic host cells (such as a yeast cell, an insect cell, or a vertebrate cell). The host cell, when cultured under appropriate conditions, expresses an antibody or binding fragment thereof which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are desirable or necessary for activity, such as glycosylation or phosphorylation, and ease of folding into a biologically active molecule. Selection of the host cell will depend in part on whether the antibody or binding fragment thereof is to be post-transcriptionally modified (e.g., glycosylated and/or phosphorylated). If so, yeast, insect, or mammalian host cells are preferable.

Suitable mammalian host cells include CHO, myeloma or hybridoma cells. Suitable types of Chinese Hamster Ovary (CHO cells) for use in the present invention may include CHO and CHO-K1 cells including dhfr-CHO cells, such as CHO-DG44 cells and CHODXB11 cells and which may be used with a DHFR selectable marker or CHOKI-SV cells which may be used with a glutamine synthetase selectable marker. Many are available from the American Type Culture Collection (ATCC), Manassas, Va. Examples include mammalian cells, such as Chinese hamster ovary cells (CHO) (ATCC No. CCL61), human embryonic kidney (HEK) 293 or 293T cells (ATCC No. CRL1573), 3T3 cells (ATCC No. CCL92), or PER.C6 cells. Other cell types of use in expressing antibodies include lymphocytic cell lines, e.g. NSO myeloma cells and SP2 cells, COS cells.

Another aspect of the present disclosure provides a process for the production of a Tau-binding antibody or binding fragment thereof comprising culturing a host cell containing e.g. a vector under conditions suitable for leading to expression of a Tau-binding antibody or binding fragment thereof from e.g. DNA encoding the Tau-binding antibody or binding fragment thereof, and isolating the antibody molecule.

The Tau-binding antibody or binding fragment thereof may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The Tau-binding antibody or binding fragment thereof antibodies and fragments according to the present disclosure are expressed at good levels from host cells. Thus the properties of the antibodies and/or fragments are conducive to commercial processing.

Thus there is provided a process for culturing a host cell and expressing the Tau-binding antibody or binding fragment thereof, isolating the latter and optionally purifying the same to provide an isolated Tau-binding antibody or binding fragment thereof. In one embodiment the process further comprises the step of conjugating an effector molecule to the isolated antibody or fragment, for example conjugating to a PEG polymer in particular as described herein.

The Tau-binding antibody or binding fragment thereof can be formulated in compositions, especially pharmaceutical or diagnostic compositions. Pharmaceutical compositions comprise a therapeutically or prophylactically effective amount of a Tau-binding antibody or binding fragment thereof in admixture with a suitable carrier, e.g., a pharmaceutically acceptable agent. Diagnostic compositions comprise a diagnostically effective amount of a Tau-binding antibody or binding fragment thereof in admixture with a suitable carrier, e.g., a diagnostically acceptable agent.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716).

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) and/or increased stability or half-life in a particular local environment. The compositions can include the formulation of antibodies, binding fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particle beads, liposomes, and implantable delivery devices that provide for the controlled or sustained release of the active agent which can then be delivered as a depot injection.

Alternatively or additionally, the compositions can be administered locally via implantation into the affected area of a membrane, sponge, or other appropriate material on to which an antibody, binding fragment, nucleic acid, or vector of the invention has been absorbed or encapsulated. Where an implantation device is used, the device can be implanted into any suitable tissue or organ, and delivery of an antibody, binding fragment, nucleic acid, or vector of the invention can be directly through the device via bolus, or via continuous administration, or via catheter using continuous infusion.

A pharmaceutical composition comprising a Tau-binding antibody or binding fragment thereof can be formulated for inhalation, such as for example, as a dry powder. Inhalation solutions also can be formulated in a liquefied propellant for aerosol delivery. In yet another formulation, solutions may be nebulized.

One aspect of the present disclosure relates to the use of Tau-binding antibodies and binding fragments thereof as a therapeutically active agent in the treatment of diseases.

Another aspect of the present disclosure relates to the use of Tau-binding antibodies and binding fragments thereof in the treatment of tauopathies. Tauopathies which have been described to contain Tau inclusions (Clavaguera et al. Brain Pathology 23 (2013) 342-349) include Alzheimer disease (AD); Amyotrophic lateral sclerosis/parkinsonism-dementia complex; Argyrophilic grain disease; Chronic traumatic encephalopathy; Corticobasal degeneration; Diffuse neurofibrillary tangles with calcification; Down syndrome; Familial British dementia; Familial Danish dementia; Frontotemporal dementia and parkinsonism linked to chromosome 17 caused by MAPT mutations; Gerstmann-Stäqussler-Scheinker disease; Guadeloupean parkinsonism; Myotonic dystrophy; Neurodegeneration with brain iron accumulation; Niemann-Pick disease, type C; Non-Guamanian motor neuron disease with neurofibrillary tangles; Pick disease; Post-encephalitic parkinsonism; Prion protein cerebral amyloid angiopathy; Progressive subcortical gliosis; Progressive supranuclear palsy (PSP); SLC9A6-related mental retardation; Subacute sclerosing panencephalitis; Tangle-only dementia; and White matter tauopathy with globular glial inclusions.

Another aspect of the present disclosure thus relates to the use of Tau-binding antibodies and binding fragments thereof in the treatment of Alzheimer's disease and/or progressive supranuclear palsy.

Correspondingly, the present disclosure also relates to methods of treating tauopathies, in particular Alzheimer's disease and/or progressive supranuclear palsy, by administering a therapeutically active amount of a Tau-binding antibody or binding fragment thereof to a subject in need thereof.

The present disclosure also relates to the use of a Tau-binding antibody or binding fragment thereof in the manufacture of a medicament for the treatment of tauopathies, in particular Alzheimer's disease and/or progressive supranuclear palsy.

In another aspect of the present disclosure the Tau-binding antibody or binding fragment thereof may be used either alone or in combination with other agents in a therapy. For instance, the Tau-binding antibody or binding fragment thereof may be co-administered with at least one additional therapeutic agent. In certain aspects, an additional therapeutic agent is a therapeutic agent affective to treat the same or different disorder as the Tau-binding antibody or binding fragment thereof is being used to treat. Exemplary additional therapeutic agents include, but are not limited to: cholinesterase inhibitors (such as donepezil, galantamine, rovastigmine, and tacrine), NMDA receptor antagonists (such as memantine), amyloid beta peptide aggregation inhibitors, antioxidants, gamma-secretase modulators, nerve growth factor (NGF) mimics or NGF gene therapy, PPARy agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide immunization, phosphodiesterase inhibitors, serotonin receptor antagonists and anti-amyloid beta peptide antibodies or further anti-tau antibodies. Additional exemplary neurological drugs may be selected from a growth hormone or neurotrophic factor; examples include but are not limited to brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alha, TGF-beta, vascular endothelial growth factor (VEGF), interleukin-1 receptor antagonist (IL-lra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF). In certain embodiments, the at least one additional therapeutic agent is selected for its ability to mitigate one or more side effects of the neurological drug. Such combination therapies noted above encompass combined administration (where two or more therapeutic agents are included in the same or separate formulations), and separate administration, in which case, administration of the Tau-binding antibody or binding fragment thereof can occur prior to, simultaneously, and/or following, administration of the additional therapeutic agent and/or adjuvant. Tau-binding antibodies or binding fragments thereof can also be used in combination with other interventional therapies such as, but not limited to, radiation therapy, behavioral therapy, or other therapies known in the art and appropriate for the neurological disorder to be treated or prevented.

Another aspect of the present disclosure relates to the use of Tau-binding antibodies and binding fragments thereof as a diagnostically active agent.

One aspect of the present disclosure also relates to the use of Tau-binding antibodies and binding fragments thereof in the diagnosis of tauopathies, in particular of Alzheimer's disease and/or progressive supranuclear palsy.

Such diagnostic testing may preferably be performed on biological samples. A "biological sample" encompasses a variety of sample types obtained from an individual and can be used in a diagnostic or monitoring assay. The definition encompasses cerebrospinal fluid, blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, blood fractions such as plasma and serum, and the like.

Diagnostic testing may preferably be performed on biological samples which are not in contact with the human or animal body. Such diagnostic testing is also referred to as in vitro testing.

In vitro diagnostic testing may rely on an in vitro method of detecting Tau in a biological sample which has been obtained from an individual comprising the steps of i) contacting the biological sample with a Tau-binding antibody or binding fragment thereof as described herein; and ii) detecting binding of the Tau-binding antibody or binding fragment thereof as described herein to Tau. By comparing the detected Tau level with a suitable control, one can then diagnose the presence or likely occurrence of a tauopathy such as Alzheimer's disease and/or progressive supranuclear palsy. Such a detection method can thus be used to determine whether a subject has, or is at risk of developing, a tauopathy including determining the stage (severity) of a tauopathy.

The present disclosure thus provides an in vitro method of diagnosing a tauopathy such as Alzheimer's disease and/or progressive supranuclear palsy in a subject comprising the steps of i) assessing the level or state of Tau in a biological sample obtained from the subject by using a Tau-binding antibody or binding fragment thereof as described herein; and ii) comparing the level or state of Tau to a reference, a standard, or a normal control value that indicates the level or state of Tau in normal control subjects. A significant difference between the level and/or state of Tau polypeptide in the biological sample and the normal control value indicates that the individual has a tauopathy such as Alzheimer's disease and/or progressive supranuclear palsy.

With respect to these various aspects and embodiments which have been described herein, the present disclosure contemplates inter alia:

1. An isolated Tau-binding antibody or binding fragment thereof, wherein said Tau-binding antibody or binding fragment thereof comprises a light chain variable region comprising a CDR1 selected from SEQ ID No.: 1 or sequences at least 90% identical thereto, a CDR2 selected from SEQ ID No.: 2 or sequences at least 90% identical thereto, and a CDR3 selected from SEQ ID No.: 3 or sequences at least 90% identical thereto; and/or a heavy chain variable region comprising a CDR1 selected from SEQ ID No.: 4 or sequences at least 90% identical thereto, a CDR2 selected from SEQ ID No.: 5 or sequences at least 90% identical thereto, and/or a CDR3 selected from SEQ ID No.: 6 or sequences at least 90% identical thereto.

2. A Tau-binding antibody or binding fragment thereof of embodiment 1, wherein said Tau-binding antibody or binding fragment thereof comprises
a light chain variable region comprising a CDR1 selected from SEQ ID No.: 1, a CDR2 selected from SEQ ID No.: 2, and a CDR3 selected from SEQ ID No.: 3; and
a heavy chain variable region comprising a CDR1 selected from SEQ ID No.: 4, a CDR2 selected from SEQ ID No.: 5, and/or a CDR3 selected from SEQ ID No.: 6.

3. A Tau-binding antibody or binding fragment thereof of embodiment 1, or 2, wherein $X_1$ of SEQ ID No.: 5 is A.

4. A Tau-binding antibody or binding fragment thereof of embodiment 1, or 2, wherein $X_1$ of SEQ ID No.: 5 is T.

5. A Tau-binding antibody or binding fragment thereof of any of embodiments 1, 2, 3, or 4, wherein said Tau-binding antibody or binding fragment thereof is a monoclonal antibody.

6. A Tau-binding antibody or binding fragment thereof of embodiment 5, wherein said Tau-binding antibody or binding fragment thereof is a chimeric, humanized or fully human antibody.

7. A Tau-binding antibody or binding fragment thereof of embodiment 6, wherein said Tau-binding antibody or binding fragment thereof is a humanized antibody of the IgG1 or IgG4 subtype.

8. A Tau-binding antibody or binding fragment thereof of any of embodiments 1, 2, 3, 4, 5, 6, or 7, wherein said Tau-binding antibody or binding fragment thereof binds to an epitope comprising the amino acid residues of A246, A239, S241, T245, S238 of SEQ ID No.: 35.

9. A Tau-binding antibody or binding fragment thereof of any of embodiments 1, 2, 3, 4, 5, 6, 7, or 8 wherein said Tau-binding antibody or binding fragment thereof binds to an epitope comprising amino acid residues S238, A239, S241, T245, A246 and one or more residues selected from S235, S237, K240, 8242, L243, Q244, V248, and M250 of SEQ ID No.: 35.

10. A Tau-binding antibody or binding fragment thereof of any of embodiments 1, 2, 3, 4, 5, 6, 7, 8, or 9, wherein said Tau-binding antibody or binding fragment binds to soluble human Tau.

11. A Tau-binding antibody or binding fragment thereof of any of embodiments 1, 2, 3, 4, 5, 6, 7, 8, or 9, wherein said Tau-binding antibody or binding fragment binds to paired helical filaments (PHF) of human Tau.

12. A Tau-binding antibody or binding fragment thereof of any of embodiments 1, 2, 3, 4, 5, 6, 7, 8, or 9, wherein said Tau-binding antibody or binding fragment binds to both soluble human and paired helical filaments (PHF) of human Tau.

13. An isolated Tau-binding antibody or binding fragment thereof, wherein said Tau-binding antibody or binding fragment thereof comprises
a light chain variable region comprising SEQ ID No.: 7 or sequences at least 80% identical thereto, and/or
a heavy chain variable region comprising SEQ ID No.: 8 or sequences at least 80% identical thereto.

14. A Tau-binding antibody or binding fragment thereof of embodiment 13, wherein said Tau-binding antibody or binding fragment thereof comprises
a light chain variable region comprising SEQ ID No.: 7, and
a heavy chain variable region comprising SEQ ID No.: 8.

15. A Tau-binding antibody or binding fragment thereof of embodiment 13, or 13, wherein $X_1$ of SEQ ID No.: 8 is A.

16. A Tau-binding antibody or binding fragment thereof of embodiment 13, or 13, wherein $X_1$ of SEQ ID No.: 8 is T.

17. A Tau-binding antibody or binding fragment thereof of any of embodiments 13, 14, 15, or 16, wherein said Tau-binding antibody or binding fragment thereof is a monoclonal antibody.

18. A Tau-binding antibody or binding fragment thereof of embodiment 17, wherein said Tau-binding antibody or binding fragment thereof is a chimeric antibody.

19. A Tau-binding antibody or binding fragment thereof of any of embodiments 13, 14, 15, 16, 17, or 18, wherein said Tau-binding antibody or binding fragment thereof binds to an epitope comprising the amino acid residues of A246, A239, S241, T245, S238, of SEQ ID No.: 35.

20. A Tau-binding antibody or binding fragment thereof of any of embodiments 13, 14, 15, 16, 17, 18, or 19, wherein said Tau-binding antibody or binding fragment thereof binds to an epitope comprising amino acid residues S238, A239, S241, T245, A246 and one or more residues selected from S235, S237, K240, 8242, L243, Q244, V248, and M250 of SEQ ID No.: 35.

21. A Tau-binding antibody or binding fragment thereof of any of embodiments 13, 14, 15, 16, 17, 18, 19, or 20, wherein said Tau-binding antibody or binding fragment binds to soluble human Tau.

22. A Tau-binding antibody or binding fragment thereof of any of embodiments 13, 14, 15, 16, 17, 18, 19, or 20, wherein said Tau-binding antibody or binding fragment binds to paired helical filaments (PHF) of human Tau.

23. A Tau-binding antibody or binding fragment thereof of any of embodiments 13, 14, 15, 16, 17, 18, 19, or 20, wherein said Tau-binding antibody or binding fragment binds to both soluble human and paired helical filaments (PHF) of human Tau.

24. An isolated Tau-binding antibody or binding fragment thereof, wherein said Tau-binding antibody or binding fragment thereof comprises
a light chain variable region comprising SEQ ID No.: 9 or sequences at least 80% identical thereto, and/or
a heavy chain variable region comprising SEQ ID No.: 10 or sequences at least 80% identical thereto.

25. A Tau-binding antibody or binding fragment thereof of embodiment 24, wherein said Tau-binding antibody or binding fragment thereof comprises
a light chain variable region comprising SEQ ID No.: 9, and
a heavy chain variable region comprising SEQ ID No.: 10.

26. A Tau-binding antibody or binding fragment thereof of embodiment 24, or 25, wherein $X_3$ of SEQ ID No.: 10 is A.

27. A Tau-binding antibody or binding fragment thereof of embodiment 24, or 25, wherein $X_3$ of SEQ ID No.: 10 is T.

28. A Tau-binding antibody or binding fragment thereof of embodiment 24, wherein the heavy chain variable region comprises SEQ ID No.: 11 or 12.

29. A Tau-binding antibody or binding fragment thereof of any of embodiments 24, 25, 26, 27, or 28, wherein said Tau-binding antibody or binding fragment thereof is a monoclonal antibody.

30. A Tau-binding antibody or binding fragment thereof of embodiment 29, wherein said Tau-binding antibody or binding fragment thereof is a humanized antibody.

31. A Tau-binding antibody or binding fragment thereof of embodiment 30, wherein said Tau-binding antibody or binding fragment thereof is of the IgG1 or IgG4 subtype.

32. A Tau-binding antibody or binding fragment thereof of any of embodiments 24, 25, 26, 27, 28, 29, 30, or 31, wherein said Tau-binding antibody or binding fragment thereof binds to an epitope comprising the amino acid residues of A246, A239, S241, T245, S238 of SEQ ID No.: 35.

33. A Tau-binding antibody or binding fragment thereof of any of embodiments 24, 25, 26, 27, 28, 29, 30, 31, or 32, wherein said Tau-binding antibody or binding fragment thereof binds to an epitope comprising amino acid residues S238, A239, S241, T245, A246 and one or more residues selected from S235, S237, K240, R242, L243, Q244, V248, and M250 of SEQ ID No.: 35.

34. A Tau-binding antibody or binding fragment thereof of any of embodiments 24, 25, 26, 27, 28, 29, 30, 31, or 32, wherein said Tau-binding antibody or binding fragment binds to soluble human Tau.

35. A Tau-binding antibody or binding fragment thereof of any of embodiments 24, 25, 26, 27, 28, 29, 30, 31, or 32, wherein said Tau-binding antibody or binding fragment binds to paired helical filaments (PHF) of human Tau.

36. A Tau-binding antibody or binding fragment thereof of any of embodiments 24, 25, 26, 27, 28, 29, 30, 31, or 32, wherein said Tau-binding antibody or binding fragment binds to both soluble human and paired helical filaments (PHF) of human Tau.

37. An isolated Tau-binding antibody or binding fragment thereof, wherein said Tau-binding antibody or binding fragment thereof comprises
a light chain comprising SEQ ID No.: 14 or sequences at least 70% identical thereto, and/or
a heavy chain comprising SEQ ID No.: 15 or sequences at least 70% identical thereto.

38. A Tau-binding antibody or binding fragment thereof of embodiment 37, wherein said Tau-binding antibody or binding fragment thereof comprises
a light chain comprising SEQ ID No.: 14, and
a heavy chain comprising SEQ ID No.: 15.

39. A Tau-binding antibody or binding fragment thereof of embodiment 37, or 38, wherein $X_3$ of SEQ ID No.: 15 is A.

40. A Tau-binding antibody or binding fragment thereof of embodiment 37, or 38, wherein $X_3$ of SEQ ID No.: 15 is T.

41. A Tau-binding antibody or binding fragment thereof of embodiment 37, wherein the heavy chain variable region comprises SEQ ID No.: 17 or 18.

42. A Tau-binding antibody or binding fragment thereof of any of embodiments 37, 38, 39, 40, or 41, wherein said Tau-binding antibody or binding fragment thereof is a monoclonal humanized antibody.

43. A Tau-binding antibody or binding fragment thereof of embodiment 42, wherein said Tau-binding antibody or binding fragment thereof is of the IgG1 or IgG4 subtype.

44. A Tau-binding antibody or binding fragment thereof of any of embodiments 37, 38, 39, 40, 41, 42, or 43, wherein said Tau-binding antibody or binding fragment thereof binds to an epitope comprising the amino acid residues of A246, A239, S241, T245, S238 of SEQ ID No.: 35.

45. A Tau-binding antibody or binding fragment thereof of any of embodiments 37, 38, 39, 40, 41, 42, 43, or 44, wherein said Tau-binding antibody or binding fragment thereof binds to an epitope comprising amino acid residues S238, A239, S241, T245, A246 and one or more residues selected from S235, S237, K240, R242, L243, Q244, V248, and M250 of SEQ ID No.: 35.

46. A Tau-binding antibody or binding fragment thereof of any of embodiments 37, 38, 39, 40, 41, 42, 43, 44, or 45, wherein said Tau-binding antibody or binding fragment binds to soluble human tau.

47. A Tau-binding antibody or binding fragment thereof of any of embodiments 37, 38, 39, 40, 41, 42, 43, 44, or 45, wherein said Tau-binding antibody or binding fragment binds to paired helical filaments (PHF) of human Tau.

48. A Tau-binding antibody or binding fragment thereof of any of embodiments 37, 38, 39, 40, 41, 42, 43, 44, or 45, wherein said Tau-binding antibody or binding fragment binds to both soluble human and paired helical filaments (PHF) of human Tau.

49. An isolated Tau-binding antibody or binding fragment thereof, wherein said Tau-binding antibody or binding fragment binds to an epitope comprising the amino acid residues of A246, A239, S241, T245, S238 of SEQ ID No.: 35.

50. A Tau-binding antibody or binding fragment thereof of embodiment 49, wherein said Tau-binding antibody or binding fragment thereof binds to an epitope comprising amino acid residues S238, A239, S241, T245, A246 and one or more residues selected from S235, S237, K240, 8242, L243, Q244, V248, and M250 of SEQ ID No.: 35.

51. A Tau-binding antibody or binding fragment thereof of embodiment 50, wherein said Tau-binding antibody or binding fragment thereof is a monoclonal antibody.

52. A Tau-binding antibody or binding fragment thereof of embodiment 50 or 51, wherein said Tau-binding antibody or binding fragment thereof is a chimeric, humanized or fully human antibody.

53. A Tau-binding antibody or binding fragment thereof of embodiment 52, wherein said Tau-binding antibody or binding fragment thereof is a monoclonal humanized antibody or binding fragment thereof of the IgG1 or IgG4 subtype.

54. A Tau-binding antibody or binding fragment thereof of any of embodiments 50, 51, 52, or 53, wherein said Tau-binding antibody or binding fragment binds to soluble human Tau.

55. A Tau-binding antibody or binding fragment thereof of any of embodiments 50, 51, 52, or 53, wherein said Tau-binding antibody or binding fragment binds to paired helical filaments (PHF) of human Tau.

56. A Tau-binding antibody or binding fragment thereof of any of embodiments 50, 51, 52, or 53, wherein said Tau-binding antibody or binding fragment binds to both soluble human Tau and paired helical filaments (PHF) of human Tau.

57. An isolated Tau-binding antibody or binding fragment thereof, wherein said Tau-binding antibody or binding fragment thereof competes for binding to Tau with a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56.

58. A Tau-binding antibody or binding fragment thereof of embodiment 57, wherein said Tau-binding antibody or binding fragment thereof competes for binding to Tau with a Tau-binding antibody or binding fragment comprising
a light chain variable region comprising SEQ ID No.: 9, and
a heavy chain variable region comprising SEQ ID No.: 12 or 13.

59. An isolated Tau-binding antibody or binding fragment thereof, wherein said Tau-binding antibody or binding fragment thereof binds to substantially the same epitope of Tau as a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56.

60. A Tau-binding antibody or binding fragment thereof of embodiment 59, wherein said Tau-binding antibody or binding fragment thereof binds to substantially the same epitope of Tau as a Tau-binding antibody or binding fragment a Tau-binding antibody or binding fragment comprising a light chain variable region comprising SEQ ID No.: 9, and a heavy chain variable region comprising SEQ ID No.: 12 or 13.

61. An isolated Tau-binding antibody or binding fragment thereof of any of embodiments 57, 58, 59, or 60, wherein said Tau-binding antibody or binding fragment thereof is a monoclonal antibody.

62. A Tau-binding antibody or binding fragment thereof of embodiment 61, wherein said Tau-binding antibody or binding fragment thereof is a chimeric, humanized or fully human antibody.

63. A Tau-binding antibody or binding fragment thereof of embodiment 62, wherein said Tau-binding antibody or binding fragment thereof is a humanized antibody of the IgG1 or IgG4 subtype.

64. A Tau-binding antibody or binding fragment thereof of any of embodiments 57, 58, 59, 60, 61, 62, or 63, wherein said Tau-binding antibody or binding fragment thereof binds to an epitope comprising the amino acid residues of A246, A239, S241, T245, S238 of SEQ ID No.: 35.

65. A Tau-binding antibody or binding fragment thereof of any of embodiments 57, 58, 59, 60, 61, 62, 63, or 64, wherein said Tau-binding antibody or binding fragment thereof binds to an epitope comprising amino acid residues S238, A239, S241, T245, A246 and one or more residues selected from S235, S237, K240, R242, L243, Q244, V248, and M250 of SEQ ID No.: 35.

66. A Tau-binding antibody or binding fragment thereof of any of embodiments 57, 58, 59, 60, 61, 62, 63, 64 or 65, wherein said Tau-binding antibody or binding fragment binds to soluble human Tau.

67. A Tau-binding antibody or binding fragment thereof of any of embodiments 57, 58, 59, 60, 61, 62, 63, 64 or 65, wherein said Tau-binding antibody or binding fragment binds to paired helical filaments (PHF) of human Tau.

68. A Tau-binding antibody or binding fragment thereof of any of embodiments 57, 58, 59, 60, 61, 62, 63, 64 or 65, wherein said Tau-binding antibody or binding fragment binds to both soluble human and paired helical filaments (PHF) of human Tau.

69. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68, wherein said Tau-binding antibody or binding fragment thereof is a Fab, Fab', a F(ab')$_2$, a Fd and a Fv, a scFv, a Fab-Fv, Fab-scFv, Fab-dsFv, Fab-scFc, scFv-scFc, dsscFv, dsscFv-scFc, a diabody, a triabody, a tetrabody, a linear antibody, or a VHH containing antibody.

70. An isolated nucleic acid molecule encoding the light and/or heavy chain of a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69.

71. A cloning or expression vector comprising one or more nucleic acid sequences of embodiment 70.

72. A host cell comprising one or more nucleic acid sequences of embodiment 70 or one or more cloning or expression vectors of embodiment 71.

73. A host cell of embodiment 72 which is not a human embryonic stem cell.

74. A method of producing a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 comprising at least the steps of a) culturing a host cell of embodiment 72 or 73, and b) isolating said Tau-binding antibody or binding fragment thereof.

75. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 for use as a therapeutically active agent.

76. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 for use in treating a tauopathy.

77. An isolated Tau-binding antibody or binding fragment thereof for use of embodiment 76, wherein said tauopathy is Alzheimer's disease.

78. An isolated Tau-binding antibody or binding fragment thereof for use of embodiment 76, wherein said tauopathy is progressive supranuclear palsy.

79. A method of treating a tauopathy comprising the step of administering a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 to a subject in need thereof.

80. A method of embodiment 79, wherein said tauopathy is Alzheimer's disease.

81. A method of embodiment 79, wherein said tauopathy is progressive supranuclear palsy.

82. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 for use as a diagnostic agent.

83. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 for use in diagnosing a tauopathy.

84. An isolated Tau-binding antibody or binding fragment thereof for use of embodiment 83, wherein said tauopathy is Alzheimer's disease.

85. An isolated Tau-binding antibody or binding fragment thereof for use of embodiment 83, wherein said tauopathy is progressive supranuclear palsy.

The invention is now described with respect to some examples which are however not be construed as limiting.

EXPERIMENTS

Experiment 1—Generation of Tau-Binding Antibodies 1.1 Recombinant Tau Expression Human Tau protein was expressed in two host systems, *E. coli* BL21 (DE3) and HEK293 cells (human embryonic kidney cell line). Four different isoforms of Tau were produced in *E. coli*, isoforms 2, 3, 4 & 5 and one isoform in HEK293 cells, isoform 2. Full sequence of all expression vectors and proteins produced are included in FIGS. 5 to 14.

Tau Production in *E. coli*

Genes encoding the different Tau isoforms were generated synthetically and codon optimised for expression in *E. coli*. Standard molecular biology techniques were used to sub-clone into a modified pET32 vector engineered to produce Tau with an N-terminal 6His-TEV tag.

*E. coli* BL 21 (DE3) cells were transformed with the above vector, and the protein was expressed using standard techniques.

*E. coli* cells were then recovered by centrifugation, lysed and Tau protein captured from the soluble fraction by affinity chromatography using NiNTA (Qiagen). The 6His tag was removed using TEV protease followed by a second NiNTA chromatography step. Purified Tau was buffer exchanged into suitable buffers dependent on application. Samples generated for immunisations had endotoxin removed using *Proteus* NoEndo™ columns (Vivaproducts).

Generation of isotopically labelled Tau for nuclear magnetic resonance (NMR) studies:

Protein expression was performed as described above except that minimal media was used for the incorporation of $^{15}N$, $^{13}C$ and $^2H$ into the protein. *E. coli* cell pellets were lysed and Tau protein was purified using a NiNTA (Qiagen) affinity chromatography step, the 6His tag was removed with TEV protease and Tau protein was then purified by Gel Filtration using a Superdex 200 unit (GE-Healthcare).

Tau Production in HEK293

A genes encoding Tau isoform 2 was generated synthetically using the wild-type DNA sequence. Standard molecular biology techniques were used to sub-clone it into expression vector pMV-10HisTEV (containing a CMV promotor) engineered to produce Tau with an N-terminal 10His-TEV tag (SEQ ID NO: 51).

The resulting vector was transfected using the Expi293™ Expression System (Invitrogen) following manufacturer's protocols. This system uses Expi293F human cells derived from the HEK293 cell line.

Tau protein accumulated in the culture media from where it was recovered using the immobilised metal ion affinity chromatography Ni Sepharose Excel (GE Healthcare). The 10His tag was then removed using TEV protease before reapplying to the Ni Sepharose column and collecting cleaved Tau in the flow through. Purified Tau was buffer exchanged into suitable buffers dependent on application.

Fibril Formation

Tau protein at 450 μM was sterile filtered and shaken in a 1.5 ml Eppendorf tube using a thermomixer (Eppendorf) at 750 rpm, 37° C. for 310 hours. Fibril formation was monitored using Thioflavin-T dye and reading absorbance on a Fluostar Omega spectrophotometer (BMG Labtech). Paired helical filament (PHF) formation was confirmed by negative stain electron microscopy.

1.2 Immunization 10 female Sprague Dawley rats (260-280 g) were immunised sub-cutaneously with 50 μg recombinant Tau protein, emulsified in an equal volume of complete Freund's adjuvant (CFA) by vigorously mixing with a syringe. Rats were given 3 booster injections at 14 day intervals using incomplete Freund's adjuvant (IFA) with bleeds also taken, from the tail. Termination occurred 14 days after the final boost with single cell suspensions of spleen and bone marrow prepared and frozen in 10% dimethyl sulfoxide (DMSO) in fetal calf serum (FCS) at −80° C. The recombinant human Tau protein was expressed in *E. coli* purified and aggregated in vitro prior to immunization. A final sample of an equimolar mix of four isoforms (2, 3, 4 & 5) of Tau containing a mix of soluble Tau and insoluble fibril Tau was used for immunization.

1.3 B Cell Culture

B cell cultures were prepared using a method similar to that described by Zubler et al. (1985). Briefly, PBMC-derived B cells from immunized rats were cultured at a density of approximately 3000 cells per well in bar-coded 96-well tissue culture plates with 200 μl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5 \times 10^4$/well) for seven days at 37° C. in an atmosphere of 5% $CO_2$. In total, approximately $1.2 \times 10^8$ B cells were sampled.

1.4 Primary Screening

The presence of Tau binding antibodies in B cell culture supernatants was determined using a homogeneous fluorescence-based binding assay using Superavidin™ beads (Bangs Laboratories) coated with biotinylated soluble or insoluble Tau obtained as described in section 1.1. The generated Tau had both a soluble and insoluble fraction. The insoluble Tau was removed from the mix via centrifugation using a bench top Eppendorf mini-spin plus centrifuge at 14,500 RPM for 10 minutes. Each fraction was biotinylated separately using EZ-link sulfo-NHS-LC-Biotinylation kit according to manufacturer's instructions. The soluble biotinylated fraction was removed from free biotin using Zeba spin desalting columns according to manufacturer's instructions. The insoluble fraction was removed from free biotin by centrifuging the mixture in an Eppendorf mini-spin plus centrifuge at 14,500 RPM for 10 minutes, recovering the Tau containing pellet and re-suspending it in 1.5 ml phosphate buffered saline (PBS) and repeating this process 5 times. The assay allowed to screen for supernatant showing binding to either soluble or insoluble Tau forms. $10_1 1.1$ of supernatant was transferred from barcoded 96-well tissue culture plates into barcoded 384-well black-walled assay plates containing soluble or insoluble Tau immobilised on beads (10 μl/well) using a Matrix Platemate liquid handler. Binding was revealed with a goat anti-rat IgG Fcγ-specific Cy-5 conjugate (Jackson). Plates were read on an Applied Biosystems 8200 cellular detection system.

1.5 Secondary Screening

Following primary screening, positive supernatants were consolidated on 96-well bar-coded master plates using an Aviso Onyx hit-picking robot and B cells in cell culture plates frozen at −800° C. Master plates were then screened in an ELISA assay on the soluble Tau fraction. This was done in order to determine, in a more stringent screen, the ability of the antibodies to bind Tau and to check they were not binding the beads in the primary screens. The ELISA assay involved the coating of soluble Tau onto 384-well Maxisorp plates (ThermoScientific/Nunc) at 3 µg/ml in a carbonate coating buffer (dH$_2$O+0.16% Na$_2$CO$_3$+0.3% NaHCO$_3$). Plates were blocked with 1% w/v casein+1% w/v BSA in PBS and then incubated with 10 µl/well of B cell culture supernatant. Secondary HRP-conjugated goat anti-rat IgG Fc antibody (Stratech Scientific Ltd/Jackson ImmunoResearch) was added to the plates, followed by visualisation of binding with TMB substrate (3,3',5,5'-Tetramethylbenzidine, from EMD Millipore; 10 µl/well). The optical density was measured at 630 nM using BioTek Synergy 2 microplate reader. B cell supernatants demonstrating specificity to Tau were selected for variable region recovery.

1.6 Variable Region Recovery

To allow recovery of antibody variable region genes from a selection of wells of interest, a deconvolution step had to be performed to enable identification of the antigen-specific B cells in a given well that contained a heterogeneous population of B cells. This was achieved using the Fluorescent foci method (Clargo et al., 2014). Briefly, Immunoglobulin-secreting B cells from a positive well were mixed with streptavidin beads (New England Biolabs) coated with biotinylated soluble Tau and a 1:1200 final dilution of a goat anti-rat Fcγ fragment-specific FITC conjugate (Jackson). After static incubation at 37° C. for 1 hour, antigen-specific B cells could be identified due to the presence of a fluorescent halo surrounding that B cell. These individual B cells, identified using an Olympus microscope, were then picked with an Eppendorf micromanipulator and deposited into a PCR tube.

Antibody variable region genes were recovered from single cells by reverse transcription (RT)-PCR using heavy and light chain variable region-specific primers. Two rounds of PCR were performed on an Aviso Onyx liquid handling robot, with the nested second PCR incorporating restriction sites at the 3' and 5' ends allowing cloning of the variable region into a mouse γ1 IgG (VH) or mouse kappa (VL) mammalian expression vector. Heavy and light chain constructs were co-transfected into HEK-293 cells using Fectin 293 (Invitrogen) and the recombinant antibody was expressed in a 125 ml Erlenmeyer flask in a volume of 30 ml. After 5-7 days of culture, the supernatants were harvested and the antibody was purified using affinity chromatography.

Experiment 2—Further Screening of Identified Antibodies 2.1 PHF Preparation

Paired helical filament (PHF)-Tau protein was purified from brain samples from donors with Alzheimer's disease or progressive supranuclear palsy or frontotemporal dementia according to the protocol published by Ksiezak-Reding and Wall (Neurobiology of Aging 15, 11-19, 1994). Fractions 8 (equivalent to crude PHF-Tau before sucrose gradient centrifugation in this reference) and 11 (equivalent to fraction A2, SDS soluble PHF as described in this reference) which have been previously described to be enriched in PHF-Tau were recovered and used for the BIAcore assay and the cellular assay of Experiment 3.

2.2 ELISA Screening

The ELISA assay involved capture of soluble Tau onto 384-well Maxisorp plates (ThermoScientific/Nunc) at 3 µg/ml in a carbonate coating buffer (dH$_2$O+0.16% Na$_2$CO$_3$+0.3% NaHCO$_3$). Plates were blocked with 1% w/v casein+1% w/v BSA in PBS and then incubated with 100/well purified antibody. Secondary HRP-conjugated goat anti-mouse IgG Fc antibody (Stratech Scientific Ltd/Jackson ImmunoResearch) was added to plates, followed by visualisation of binding with the HRP-substrate TMB substrate (3,3',5,5'-Tetramethylbenzidine, from EMD Millipore; 10 µl/well). The optical density was measured at 630 nM using BioTek Synergy 2 microplate reader.

2.3 BIAcore Screening

Selected monoclonal Fab fragments (mFab) were prepared from chimeric mIgG1 antibodies using the Pierce Ficin cleavage kit (Cat. No. 44980, Thermo Scientific) according to the protocol of the manufacturer.

Absorption at 280 nm was used to determine the concentration of the Fab stock solutions for the BIAcore analysis. An insoluble Tau protein preparation from Alzheimer's disease patients (AD-PHF, fraction 11), the HEK-derived Tau isoform-2 monomers (amino acids 1-441), and the isoform-2 monomers expressed in E. coli were amine immobilized onto the CM5 chip, and binding of anti-Tau mFabs was measured with the Biacore T200 instrument. The buffer HBS-EP from GE Healthcare was used for immobilizations apart from the AD-PHF for which 10 mM acetic acid (pH3.0) was used. The HBS-EP+buffer was supplemented with 300 mM NaCl and 1.25% CM-Dextran (Sigma) and used as the assay buffer. While flow cell (Fc) 1 was used as a reference, the following RU values were obtained for Fc2-4: 44 RU with 5 µg/ml E. coli Tau, 56 RU with 5 µg/m HEK Tau, and 500 RU with a 1:20 diluted solution of the AD-PHF material. Two 60s cycles of 10 mM Glycine (pH1.7) were used for regeneration. Flow rates of 10 µl/min were used for immobilization and regeneration while a 30 µl/min flow rate was used for analyte binding. For AD-PHF, multiple manual injections were applied to reach 500 RU, including EDC/NHS and EtoA capping. Five start-up cycles and 12 cycles per mFab sample or buffer control were applied, using 90 µl analyte injections for either 180s or 300 s for dissociation. 11 1:3 dilutions of a 600 nM solution plus buffer were used for each mFab. AB 1 was analyzed using the BIAcore test.

The results are depicted in Table 1 which shows the binding of mFab AB1 having a rat VL of SEQ ID No.: 7 and a rat VH of SEQ ID No.: 8 to monomeric Tau isoform-2 expressed in E. coli, to monomeric Tau isoform-2 derived from mammalian HEK293 cells, and to isolated Tau PHF fibrils from Alzheimer's disease patients (aggregated Tau). The binding profile of AB1 and above referenced prior art antibodies is shown in Table 3.

TABLE 1

| Ab | Tau source | Rmax (RU) | ka (1/Ms) | kd (1/s) | KD (M)* |
|---|---|---|---|---|---|
| 101.4 (isotype control) | Ecoli iso-2 | nb | — | — | — |
| | HEK iso-2 | nb | — | — | — |
| | AD-PHF | nb | — | — | — |
| AB1 | Ecoli iso-2 | 17 | 6.9E+04 | 1.1E−02 | 1.6E−07 |
| | | 17 | 7.3E+04 | 1.1E−02 | 1.6E−07 |
| | HEK iso-2 | 15 | 7.0E+04 | 1.1E−02 | 1.6E−07 |
| | | 15 | 6.6E+04 | 1.1E−02 | 1.7E−07 |
| | AD-PHF | 7 | 5.2E+04 | 9.6E−03 | 1.9E−07 |
| | | 6 | 4.4E+04 | 8.0E−03 | 1.8E−07 | nb = no binding
*major binding component values shown

Experiment 3—Further Characterization of Identified Antibodies 3.1 Cellular Assay
Preparation of Crude Soluble and Insoluble Fractions from Tau Transgenic Mice to Induce Tau Aggregation For these experiments transgenic mice expressing human Tau P301S (Allen et al., 2002 J. Neurosci. 22(21):9340-51, and P301L (Lewis et al., 2000 Nat Genet. (4):402-5; Götz J, et al., 2001 J Biol Chem. 276(1):529-34) were used.

Crude soluble and insoluble fractions were prepared from the brain of P301S and P301L Tau transgenic mice by differential centrifugation. Briefly, brain tissues from P301S (spinal cord and brainstem) and P301L (midbrain and brainstem) tau transgenic mice were homogenized in ice-cold TBS (Fisher Scientific) using the hand-held homogenizer Pellet Pestle Motor (Kontes) in 1.5 ml microcentrifuge tubes on ice. Then, homogenates (H) were centrifuged at 4,000 g for 10 min at 4° C. to remove tissue debris. Resulting supernatants (S0) were centrifuged at 20,000 g for 20 min at 4° C. to provide supernatants corresponding to the crude soluble fraction (S1). The remaining pellets (P1) were resuspended in 1 ml of 1% sarkosyl solution prepared in TBS, incubated for 1 h at room temperature, and then centrifuged at 100,000 g for 1 h at 4° C. The supernatants (S2) were discarded. The pellets (P2) were washed with 5 ml ice-cold TBS, and then resuspended in TBS to provide the crude insoluble fraction (P2').

Preparation of HEK-293-F Cells Expressing Human Tau with P301S Mutation

HEK-293-F cells (Life Technologies) were transfected with the pcDNA3.1(+) vector expressing human Tau isoform 2 with a P301S mutation, using 293fectin (Life Technologies) according to manufacturer's instructions. Aliquots of transfected cells were stored in liquid nitrogen.

Induction of Tau Aggregation

FIG. 3 illustrates the different steps of the cellular aggregation assay used to characterize the activity of Tau therapeutic antibodies. On day 1, HEK-293-F cells expressing human Tau isoform 2 with P301S mutation (P301S-tau) were defrosted at 37° C. and diluted in 293 Expression medium (Life Technologies) containing 10% fetal bovine serum and 1% Penicillin-Streptomycin (FFBS). Cells were counted using an automatic cell counter (Vi-CELL XR, Beckman Coulter), and then plated in poly-D-lysine pre-coated 96-well plates (Greiner Bio-One) at a density of 25,000 live cells per well. Cells were maintained at 37° C. in 5% $CO_2$. The same day, sonicated human insoluble Tau from patients with Alzheimer's disease (AD-PHF, fraction 8) or progressive supranuclear palsy (PSP-PHF, fraction 8) or frontotemporal dementia (FTD-PHF, fraction 8) or brain fractions from P301S or P301L transgenic mice brains, (used as seeds to induce Tau aggregation), were incubated with or without anti-Tau antibodies in FFBS medium at 4° C. with gentle agitation overnight. AD-PHF, fraction 8 was used at 80 ng/µl and 60 ng/µl for AD and PSP samples, respectively; soluble brain fraction from transgenic mice P301S and P301L were used at 0.1 µg/µl t 1.2 µg/µl, respectively. On day 2, seeds or seed/antibody mixtures were applied to cells for 24h. On day 3, the culture medium was replaced with fresh FFBS medium containing antibody, and cells were maintained in culture for an additional 24h. On day 4, Tau aggregation was measured using a tau aggregation assay kit (Cisbio) based on homogenous time-resolved fluorescence energy transfer (HTRF), according to manufacturer's instructions. Fluorescence was measured with SpectraMax Paradigm (Molecular Devices). Aggregation was reported as percent aggregation relative to control (−) which corresponds to the maximal aggregation response induced by exogenous fibrils or fractions in the absence of the antibody.

The effect of AB1 and other Tau-binding antibodies of the prior art on induced Tau aggregation were tested. The prior art antibodies were IPN002 of WO2014/028777A2, PT3 of WO2013/096380A2, mAb2.10.3 of WO2010/142423A2, and HJ8.5 of WO 2014/008404.

The results of this assay are summarized in Table 2 and FIG. 4.

Table 2 summarizes the potency ($IC_{50}$) and maximal efficacy ($I_{max}$ at 300 nM) of AB1 having a rat VL of SEQ ID NO: 7 and a rat VH of SEQ ID NO.:8, of a Tau-binding antibody having the light chain of SEQ ID No.: 14 and the heavy chain of SEQ ID No.:17 (L14H17), a Tau-binding antibody having a the light chain of SEQ ID No.: 14 and the heavy chain of SEQ ID No.:18 (L14H18), and competitor antibodies against a range of Tau seed from various brain extracts. Whereas FIG. 4 shows the efficacy of a Tau-binding antibody having the light chain of SEQ ID No.: 14 and the heavy chain of SEQ ID No.:17 (L14H17), and of a Tau-binding antibody having a the light chain of SEQ ID No.: 14 and the heavy chain of SEQ ID No.:18 (L14H18) in a cellular aggregation assay using human Tau pathological fibrils from human AD patients.

3.2 Histological Analysis

AB1 having a rat VL of SEQ ID NO: 7 and a rat VH of SEQ ID NO.:8 and the antibodies IPN002, PT3 and Mab2.10.3 of the prior art were assayed and optimal concentration determined using cryosections of human hippocampus from a donor with Alzheimer's disease that had previously been shown to contain pathological Tau structures using AT8 immunostaining (such as described in Braak & Braak, 1995, Neurobiol Aging; 16(3):271-8). AB1 and all prior art antibodies exhibited specific and concentration-dependent immunoreactivity, apart from 101.4 (negative control antibody). From these data a single, optimal concentration of antibody was selected and used to screen a panel of six human brain samples. Three samples originated from donors with Alzheimer's disease or from very elderly donors that exhibited high levels of Tau pathology (positive Tau pathology detected using AT8 immunostaining), and three from donors without Tau pathology (negative Tau pathology detected using AT8 immunostaining).

AB1 and IPN002, showed specific immunostaining of neurofibrillary tangles (intraneuronal NFT), cytoplasmic staining of neurofibrillary tangles (extraneuronal NFT), neuritic plaque-like structures, and neurophil threads within the Tau positive pathology samples. They also showed immunostaining in the samples classified with Tau negative pathology.

The results of Experiments 2 and 3 are summarized in Tables 2 and 3 below:

TABLE 2

| | Experiment 3.1 | | | | |
|---|---|---|---|---|---|
| mAB | Tg mice (P301S) $IC_{50}/I_{max}$ | Tg mice (P301L) $IC_{50}/I_{max}$ | Human AD samples $IC_{50}/I_{max}$ | Human PSP samples | Human FTD samples |
| AB1 | $IC_{50}$: 2 nM $I_{max}$: 93% | $IC_{50}$: 30 nM $I_{max}$: 89% | $IC_{50}$: 4 nM $I_{max}$: 98% | Not tested | $IC_{50}$: 3 nM $I_{max}$: 97% |
| L14H17 | Not tested | Not tested | $IC_{50}$: 11 nM $I_{max}$: 98% | Not tested | Not tested |
| L14H18 | Not tested | Not tested | $IC_{50}$: 12 nM $I_{max}$: 98% | $IC_{50}$: 42 nM $I_{max}$: 100% | $IC_{50}$: 1 nM $I_{max}$: 99% |
| IPN002 | $IC_{50}$: ND $I_{max}$: 22% | $IC_{50}$: 122 nM $I_{max}$: 73% | $IC_{50}$: ND $I_{max}$: 19% | $IC_{50}$: 207 nM $I_{max}$: 64% | $IC_{50}$: ND $I_{max}$: 50% |
| PT3 | $IC_{50}$: 350 nM $I_{max}$: 56% | $IC_{50}$: 26 nM $I_{max}$: 69% | $IC_{50}$: 32 nM $I_{max}$: 69% | $IC_{50}$: 47 nM $I_{max}$: 55% | $IC_{50}$: 1 nM $I_{max}$: 80% |
| Mab2.10.3 | $IC_{50}$: ND $I_{max}$: 35% | $IC_{50}$: ND $I_{max}$: 29% | $IC_{50}$: ND $I_{max}$: 16% | $IC_{50}$: ND $I_{max}$: 28%(*) | $IC_{50}$: ND $I_{max}$: 30% |
| HJ8.5 | $IC_{50}$: ND $I_{max}$: 43% | Not tested | $IC_{50}$: ND $I_{max}$: 46% | $IC_{50}$: 73 nM $I_{max}$: 79% | $IC_{50}$: ND $I_{max}$: 67% |

TABLE 3

| mAB | Experiment 3.2 | Experiment 2.3 | Experiment 3.3 |
|---|---|---|---|
| AB1 | AD[1] & ctrl.[2] | Monom.[3] & Agg.[4] | +AD, PSP, ctr |
| IPN002 | AD[1] & ctrl.[2] | Monom. & Agg. | +AD, PSP, ctr |
| PT3 | AD > ctr | Agg | Weak |
| Mab2.10.3 | AD > ctr | Agg | Weak |

[1] stands for detection of Tau in samples of confirmed Tau pathology.
[2] stands for detection of Tau in samples of Tau negative pathology.
[3] stands for the monomeric Tau form of monomeric Tau isoform-2 expressed in E. coli and monomeric Tau isoform-2 derived from mammalian HEK293 cells.
[4] stands for aggregated Tau form of isolated Tau PHF fibrils from Alzheimer's disease patients
ND: Not determined.
(*) maximal efficacy at 100 nM

3.3 Western Blot

Western blots performed using a chemiluminescent read out: homogenates prepared from AD, PSP or control humans was loaded onto 10% polyacrylamide gels (20 μg protein per lane). Proteins were separated by SDS-PAGE (sodium dodecyl sulfate Polyacrylamide gel electrophoresis) and electrotransferred on to PVDF (Polyvinylidene fluoride) membrane. Membranes were blocked in 4% BSA (bovine serum albumin (in TBST: 50 mM Tris, 150 mM NaCl, 0.05% Tween 20, Adjust pH with HCl to pH 7.6). Membranes were incubated overnight at 4° C. with primary antibody or non-immune IgG control antibody, rinsed in TBST, incubated with secondary antibody for 1 hour (mouse anti-biotin), rinsed in TBST, incubated with tertiary antibody for 1 hour (anti-mouse IgG-peroxidase), rinsed in TBST, and developed using ECL (enhanced chemiluminescence)-film exposures for 2 to 5 minutes.

Alternatively, western blots were performed using a fluorescent read out: Homogenates (H), soluble (S1) and insoluble (P2') fractions from tau transgenic mice or AD-PHF fraction 8 were loaded in NuPAGE® Novex 4-12% Bis-Tris gels (Life Technologies), and then separated by SDS-PAGE. The separated proteins were electrotransferred onto polyvinylidene difluoride membranes using Trans-Blot® Turbo™ Transfer System (Bio-Rad). The membranes were blocked with Odyssey® blocking buffer (LI-COR) and incubated overnight at 4° C. with different primary antibodies diluted in same buffer containing 0.1% Tween-20. IRDye secondary antibodies were diluted in Odyssey® blocking buffer containing 0.1% Tween-20 and 0.01% SDS (1:5,000; LI-COR) and incubated for 1 h at room temperature, and visualization was performed using Odyssey CLx imaging system (LI-COR). VR4295 (UCB Biopharma S.P.R.L), IPN002, PTR3 and Mab2.10.3 antibodies were used at 0.1-1 μg/ml. Anti-tau pS202/T205 (ATB; Thermo Scientific), anti-Tau pThr231 (AT180; Thermo Scientific) and anti-total Tau (HT7; Thermo Scientific) were used at 1:200 dilution. To control for loading, blots were analyzed for β-actin (1:2,000; Sigma). Signal intensities were quantified using Image Studio 3.1 (Li-COR).

AB1 having a rat VL of SEQ ID No: 7 and a rat VH of SEQ ID No.:8 and humanized versions having a light chain of SEQ ID No.: 14 and a heavy chain of SEQ ID No.: 17 or a light chain of SEQ ID No.: 14 and a heavy chain of SEQ ID No.: 18 bind to pathological Tau from P301S and P301L transgenic mice and from samples of human AD, PSP and control patients. All three antibodies display a similar pattern of binding by western blot and reveal in AD and PSP a typical band pattern between 50 and 75 kDa corresponding to pathological Tau from AD and PSP (see FIG. 5). IPN002 showed a similar behaviour, whereas PTR3 and Mab2.10.3 antibodies bind to pathological Tau from P301S and P301L transgenic mice and weakly bind human AD but exhibit a different pattern by western blot. The negative control 101.4 and A33 antibodies did not reveal any significant signal. Actin was used as a load control.

3.4 Defining the Epitope of AB1

Epitope binding of antibody AB1 having a VL of SEQ ID No.: 7 and a VH of SEQ ID No.: 8 was determined using heteronuclear single quantum coherence nuclear magnetic resonance (HSQC NMR) using a Fab fragment of the antibody.

Backbone Assignment of Tau Isoform 4

NMR samples were typically 350 μl in volume with a protein concentration of 270 μM of $^2H/^{13}C/^{15}N$ labelled human Tau isoform 4 in 5 mm Shigemi tubes. Buffer conditions were 100 mM NaCl, 25 mM Sodium Phosphate pH 6.4, 10 μM AEBSF, 0.02% NaN$_3$. All experiments were recorded at 20° C. on either 600 MHz Bruker DRX or 800 MHz Bruker Avance spectrometers fitted with cryogenically cooled probes. Sequential connections between backbone NMR signals of residues in the protein, $H_N(i)$-N(i)-N(i±1), were made using a 3D (H)N(CA)NNH experiment (Weisemann et al., 1993 3D Triple-resonance NMR techniques for the sequential assignment of NH and 15N resonances in 15N- and 13C-labelled proteins. J. Biomol. NMR 3. doi: 10.1007/BF00242479) recorded with spectral widths of 1640, 1640 and 7000 Hz and acquisition times of 120 (F1), 120 (F2) and 150 (F3) ms in the $^{15}$N, $^{15}$N and $^{1}$H dimensions, respectively, with 8 scans per increment and a 1.5 s relaxation delay. Non-uniform sampling was employed with a sampling density of 13% (5200 out of 40000 hypercomplex points) giving a total acquisition time of 3.5 days. Sequential connections were confirmed and residue types identified using HNCA (Grzesiek and Bax, 1992 Improved 3D triple-resonance NMR techniques applied to a 31 kDa protein. J. Magn. Reson. 96, 432-440. doi:10.1016/0022-2364(92)90099-S) and HNCACB (Wittekind and Mueller, 1993 HNCACB, a High-Sensitivity 3D NMR Experiment to Correlate Amide-Proton and Nitrogen Resonances with the Alpha- and Beta-Carbon Resonances in Proteins. J. Magn. Reson. Ser. B 101, 201-205. doi:10.1006/jmrb.1993.1033) experiments. The HNCA experiment was recorded with spectral widths of 1640, 4830 and 6600 Hz and acquisition times of 24 (F1), 6.6 (F2) and 80 (F3) ms in the $^{15}$N, $^{13}$C and $^{1}$H dimensions respectively (8 scans per increment, 1.5 s relaxation delay, 19 hours total acquisition time) whilst the HNCACB was recorded with spectral widths of 9800, 1640 and 6600 Hz and acquisition times of 6 (F1), 24 (F2) and 80 (F3) ms in the $^{13}$C, $^{15}$N and $^{1}$H dimensions respectively (8 scans per increment, 1.5 s relaxation delay, 1.5 days total acquisition time). NMR spectra were processed using NMRPipe (Delaglio et al., 1995 NMRPipe: a multidimensional spectral processing system based on UNIX pipes. J. Biomol. NMR 6, 277-93) with reconstruction of the NUS data performed using the Harvard iterative soft thresholding method (Hyberts et al., 2012). Data analysis was carried out using Sparky (Goddard and Kneller, D. G. SPARKY 3. In., University of California, San Francisco), resulting in the assignment of the amide proton and nitrogen resonances of 304 residues, corresponding to 96% of residues (excluding proline residues and the N-terminal glycine).

Mapping the Binding Site of AB1:

Mapping of the binding site of AB1 was carried out using samples of $^{2}$H/$^{13}$C/$^{15}$N labelled human Tau isoform 4 ranging in concentration from 80 to 150 µM and containing a 10% molar excess of the corresponding AB1 Fab. Samples were prepared in the same buffer as described above for the backbone assignment of the Tau. $^{1}$H, $^{15}$N and $^{13}$C chemical shift changes were determined from HNCO (Grzesiek and Bax, 1992 Improved 3D triple-resonance NMR techniques applied to a 31 kDa protein. J. Magn. Reson. 96, 432-440. doi:10.1016/0022-2364(92)90099-S) spectra recorded on the Tau/Fab complex samples as well as a sample of the free Tau (as described above). The HNCO experiments were recorded with spectral widths of 2190, 2210 and 8800 Hz and acquisition times of 25 (F1), 29 (F2) and 80 (F3) ms in the $^{15}$N, $^{13}$C and $^{1}$H dimensions respectively (8 scans per increment, 1.8 s relaxation delay), with NUS employed using sampling densities of 25-35%, reducing total acquisition times from 60 hours to 15-21 hours. Chemical shift changes were analysed using the minimal shift approach (Williamson et al., 1997 Mapping the binding site for matrix metalloproteinase on the N-terminal domain of the tissue inhibitor of metalloproteinases-2 by NMR chemical shift perturbation. Biochemistry 36, 13882-9. doi:10.1021/bi9712091), essentially as described previously (Veverka et al., 2008 Structural characterization of the interaction of mTOR with phosphatidic acid and a novel class of inhibitor: compelling evidence for a central role of the FRB domain in small molecule-mediated regulation of mTOR. Oncogene 27, 585-95. doi:10.1038/sj.onc.1210693), with the exception of a modification to the equation used to calculate the combined chemical shift change (Δs) to include the carbonyl chemical shift, resulting in the following equation:

$$\Delta\delta = \frac{\sqrt{(\Delta\delta HN)^2 + (\Delta\delta N\alpha N)^2 + (\Delta\delta C\alpha C)^2}}{3}$$

where $\Delta\delta_{HN}$, $\Delta\delta_{N}$ and $\Delta\delta_{C}$ are the differences in the $^{1}$H, $^{15}$N and $^{13}$C chemical shifts respectively. αN and αC correspond to scaling factors of 0.2 and 0.35, respectively, used to account for differences in the chemical shift ranges of the amide proton, nitrogen and carbonyl chemical shifts.

To identify the Fab binding sites (epitopes) on Tau, a histogram of combined minimal shift versus protein sequence was used to reveal regions of Tau containing significantly perturbed signals. If the size of the combined chemical shift change for individual amino acids exceeded a threshold value of the mean of the combined chemical shift change for all the amino acids plus one standard deviation from that mean, these residues were selected for further evaluation as possible contact residues in the Fab binding site.

Significantly perturbed residues were identified as those whose minimal shift was at least greater than the mean plus one standard deviation of all calculated shifts. Four different thresholds were applied to identify residues bound by the Fab. Residues that are involved in the binding site are scored with increasing stringency as: those whose minimal shift exceeds mean plus one standard deviations of all calculated shifts (being >0.009817); those whose minimal shift exceeds mean plus two standard deviations of all calculated shifts (being >0.016913); those whose minimal shift exceeds mean plus three standard deviations of all calculated shifts (being >0.024009); those whose minimal shift exceeds mean plus four standard deviations of all calculated shifts (being >0.031105). In this analysis Proline residues cannot be identified as they contain no amide proton.

The epitope for AB1 Fab is therefore defined with increasing stringency as mean plus one standard deviation of all calculated shifts: A246, A239, S241, T245, S238, S235, K240, Q244, S237, V248, L243, M250, R242; mean plus two standard deviation of all calculated shifts: A246, A239, S241, T245, S238, S235, K240, Q244, S237; mean plus three standard deviation of all calculated shifts: A246, A239, S241, T245, S238, S235, K240, Q244; mean plus four standard deviation of all calculated shifts: A246, A239, S241, T245, S238.

Using the amino acid numbering used in NCBI Reference Sequence NP_005901.2 (SEQ ID No.: 35) AB1 was found to bind at least the following residues (mean+3 SD) A246, A239, S241, T245, S238, S235, K240, Q244. The antibody may bind all of the following residues (mean+1 SD) A246, A239, S241, T245, S238, S235, K240, Q244, S237, V248, L243, M250, R242.

Experiment 4—Humanization of Identified Antibodies

Antibody AB1 having a VL of SEQ ID No.: 7 and a VH of SEQ ID No.: 8 was humanized by grafting the CDRs from the rat antibody V-regions onto human germline antibody V-region frameworks.

In order to recover the activity of the antibody, a number of framework residues from the rat or rabbit V-regions were also retained in the humanized sequence. These residues were selected using the protocol outlined by Adair et al.

(1991) (Humanised antibodies. WO91/09967). Alignments of the rat antibody (donor) V-region sequences with the human germline (acceptor) V-region sequences are shown in FIGS. 1, and 2 together with the designed humanized sequences. The CDRs grafted from the donor to the acceptor sequence are as defined by Kabat (Kabat et al., 1987), with the exception of CDR-H1 where the combined Chothia/Kabat definition is used (see Adair et al., 1991 Humanised antibodies, WO91/09967).

Human V-region IGKV2-29 plus JK2 J-region (IMGT, see Worldwide Website: imgt.org/) (SEQ ID No.: 31) was chosen as the acceptor for antibody AB1 light chain CDRs. The light chain framework residues in graft gVL3_AB1 (SEQ ID No.: 14) are all from the human germline gene.

Human V-region IGHV4-59 plus JH3 J-region (IMGT, see Worldwide Website: imgt.org/) (SEQ ID No.: 32) was chosen as the acceptor for the heavy chain CDRs of antibody AB1. The heavy chain framework residues in grafts gVH17_AB1 (SEQ ID No.: 17) and gVH18_AB1 (SEQ ID No.: 18) are all from the human germline gene, with the exception of residue 48 (Kabat numbering), where the donor residue Methionine (M48) was retained. Retention of residue M48 allowed for full potency of the humanized antibody. The Glutamine residue at position 1 of the human framework was replaced with Glutamic acid (E1) to afford the expression and purification of a homogeneous product: the conversion of Glutamine to pyroGlutamate at the N-terminus of antibodies and antibody fragments is widely reported. CDRH2 of SEQ ID No.: 37 and 38 was mutated in grafts gVH17_AB1 and gVH18_AB1 respectively to modify a potential deamidation site.

Genes encoding a number of variant heavy and light chain V-region sequences for the antibody were designed and constructed by an automated synthesis approach by DNA2.0 Inc. Further variants of heavy and light chain V-regions were created by modifying the VH and VK genes by oligonucleotide-directed mutagenesis, including, in some cases, mutations within CDRs to modify potential deamidation sites. For transient expression in mammalian cells, the humanized light chain V-region genes were cloned into the UCB human light chain expression vector pMhCK, which contains DNA encoding the human Kappa chain constant region (Km3 allotype). The humanized heavy chain V-region genes were cloned into the UCB human gamma-4 heavy chain expression vector pMhγ4P FL, which contains DNA encoding the human gamma-4 heavy chain constant region with the hinge stabilizing mutation S241P (Angal et al., Mol Immunol. 1993, 30(1):105-8). Alternatively, the humanized VH genes were cloned into the UCB human gamma-1 heavy chain expression vector pMhγ1FL, which contains DNA encoding the human gamma-1 heavy chain constant region (G1m17, 1 allotype). In order to assess the monovalent binding kinetics of the humanized antibodies, the humanized VH genes were also cloned into the UCB human Fab-HIS expression vector pMhFab10HIS, which contains DNA encoding the human gamma-1 CH1-hinge domain with a C-terminal tag of ten Histidine residues: the histidine tag facilitates purification of the expressed Fabs by affinity chromatography. Co-transfection of the resulting heavy and light chain vectors into HEK293 suspension cells was achieved using 293 Fectin (12347-019 Invitrogen), and gave expression of the humanized, recombinant antibodies in either the human IgG4P, IgG1 or Fab-HIS formats.

The variant humanized antibody chains, and combinations thereof, were expressed and assessed for their potency relative to the parent antibody, their biophysical properties and suitability for downstream processing.

For stable expression of the humanized recombinant antibodies in mammalian cells, the humanized light chain V-region gene was joined to a DNA sequence encoding the human C-Kappa constant region (Km3 allotype), to create a contiguous light chain gene. The humanized heavy chain genes were joined to DNA encoding either the human gamma-4P heavy chain constant region, or the human gamma-1 heavy chain constant region (G1m17, 1 allotype), to create contiguous heavy chain genes. Heavy and light chain genes were cloned into a mammalian expression vector.

Experiment 5—Thermal Stability Measurement

The melting temperature (Tm) or temperature at the midpoint of unfolding, was determined using the Thermofluor assay. In this method, the fluorescent dye SYPRO orange was used to monitor the protein unfolding process by binding to hydrophobic regions that become exposed as the temperature increases.

The reaction mix contained 5 µl of 30×SYPRO® Orange dye (Invitrogen), diluted with PBS from 5000× stock solution and 45 µl of sample at 0.12 mg/ml, (in PBS pH 7.4). 10 µl of the mix was dispensed in quadruplicate into a 384 PCR optical well plate and was run on a 7900HT Fast Real-Time PCR System (Applied Biosystems). The PCR system heating device was set at 20° C. to 99° C. with an increase rate of 1.1° C./min. A charge-coupled device monitored fluorescence changes in the wells. Intensity increases were plotted, and the inflection point of the slope(s) was used to calculate the Tm as described below.

Analysis of antibodies containing the light chain of SEQ ID No.: 14, and a heavy variable chain of SEQ ID No.: 12 or SEQ ID No.: 13 for isotypes IgG1 (light chain of SEQ ID No.: 14 and heavy chain of SEQ ID No.: 54 (L14/H54), or light chain of SEQ ID No.: 14 and heavy chain of SEQ ID No.: 55 (L14/H55)) and IgG4 (light chain of SEQ ID No.: 14 and heavy chain of SEQ ID No.: 17 (L14/H17), or light chain of SEQ ID No.: 14 and heavy chain of SEQ ID No. 18 (L14/H18)) is shown in FIG. 6 and Table 3 below. Two unfolding domains were observed for both isotypes. The first can be attributed to the Tm of the CH2 domain; for the IgG1 isotype this was found to be higher (more stable) than the IgG4 format, in accordance with the literature (Garber E, Demarest S J. Biochem Biophys Res Commun. 2007 Apr. 13; 355(3):751-7). The second unfolding domain can be attributed to an average of the Tm of the Fab unfolding domain and CH3 domain.

| Antibody | Fab/CH3 (mean) | Fab/CH3 (SD) | CH2 (mean) | CH2 (SD) |
|---|---|---|---|---|
| L14/H17 | 80.9° C. | 0.3° C. | 64.5° C. | 0.3° C. |
| L14/H18 | 81.4° C. | 0.7° C. | 64.5° C. | 0.5° C. |
| L14/H54 | 82.8° C. | 0.2° C. | 68.8° C. | 0.2° C. |
| L14/H55 | 83° C. | 0.1° C. | 68.8° C. | 0.2° C. |

Experiment 6—X-Ray Crystallography

The interaction between a Tau-binding antibody having the light chain of SEQ ID NO: 14 and the heavy chain of SEQ ID NO: 18 (L14H18) and a peptide consisting of residues 234 to 250 of Tau as defined in SEQ ID NO: 35 (peptide, N-acetyl-KSPSSAKSRLQTAPVPM-amide defined in SEQ ID NO: was studied by x-ray crystallography.

Crystallisation, Structure Determination and Refinement of the crystal structure of tau peptide complexed with L14H18 Fab.

Crystallisation

The L14H18 Fab/tau peptide 234-250 complex crystallized from a sitting drop through the vapour phase against a reservoir containing 30% w/v polyethylene glycol 4000, 0.1M HEPES, pH 7.5, 0.2 M Calcium Chloride dehydrate for 1-2 weeks in MRC plates.

The drops contained 400 nl of L14H18 Fab protein at 11 mg/ml with a 2 molar excess of tau peptide 234-250 and 400 nl of reservoir solution.

The crystals belong to the space group P 31 2 1, with two copies of the L14H18 Fab/tau peptide 234-250 in the asymmetric unit.

X-Ray Diffraction Collection

We collected the x-ray diffraction data through a single L14H18 Fab/tau peptide 234-250 crystal. The crystal was suspended in a litho loop and flash frozen under liquid nitrogen, after briefly passing through a cryoprotectant solution containing 30% polyethylene glycol 4000, 0.2M calcium chloride, 0.1M HEPES buffer pH 7.5 and 10% ethylene glycol. The diffraction data was collected on a Pilatis 6M at the 104-1 beamline station at the Diamond synchrotron, Didcot, Oxfordshire, UK. The wavelength of the monochromatic x-ray beam was 0.92819Å. The reciprocal space was sampled at 0.2° oscillation steps around the φ goniostat axis. The processed data XIA file provided from the synchrotron facility was used for structure determination Structure Determination The Fab position was located by the molecular replacement program Phaser (Read, R J, Acta Cryst. D57, 1373-1382 (2001)), using the Fab with PDB code 4HIX. The Matthews coefficient indicated a likely molecular weight of 100 kDa in the unit cell, the solution found 2 copies of the Fab in the asymmetric unit.

Model Building and Refinement

Using 2Fo-Fc and Fo-Fc electron density maps, residues in the Fab molecule were replaced according to the sequence of the L14H18 Fab with the positions guided by the electron density maps.

Fab chains C and D for the second copy of the Fab had clearer density than the first copy (chains H and L).

Extra electron density was visible adjacent to the CDRs of one copy of the Fab (chains C and D). This revealed a peptide chain with a helical structure into which part of the sequence of peptide 234-250 could be built. The peptide was aligned using clear density for arginine and lysine residues then built according to the known sequence. Further rounds of model building and refinement improved the density for the peptide region and showed some density for a peptide bound to the other copy of the Fab (chains H and L).

For model building the computer program Coot (Emsley P., Lohkamp B., Scott W. G., Cowton K. Acta Crystallography D Biol Crystallography, 2010 April; 66 (Pt 4): 486-501) was used. Refinement was carried out using the program REFMAC (Murshudov G. N., Skubak P., Lebedev A. A., Pannu N. S., Steiner R. A., Nicholls R. A., Winn M. D., Long F., Vagin A. A. Acta Crystallogr D Biol Crystallogr 2011 April; 67 (Pt 4): 355-67).

The model of L14H18 Fab/tau peptide 234-250 complex consists of residues 234-244 of the Tau peptide as defined in SEQ ID NO: 35, residues 2-219 of the heavy chain and 1-219 of the light chain.

The R-factor of the model is 0.234 and R-free is 0.291 for 36483 reflections. The rms deviation from standard geometry is 0.0145 for bond lengths and 1.930 for bond angles.

The Epitope

The interaction between antibody L14H18 and tau peptide, N-acetyl-KSPSSAKSRLQTAPVPM-amide (based on human tau isoform 2 sequence 234 to 250), was studied by x-ray crystallography using a co-complex prepared from L14H18 Fab fragment incubated with the peptide. The resulting structure revealed the major contact sites between L14H18 Fab and the tau peptide, and were identified as clustered mainly at the CDR loops of the antibody and peptide residues SPSSAKSRLQ corresponding to residues 235-244 of tau protein. According to the numbering sequence, as shown in SEQ ID NO. 35, the residues which interact most closely with the CDR region of L14H18 Fab within 5.0 A are S235, P236, S237, S238, A239, K240, R242, L243, Q244 and T245.

The invention claimed is:

1. An isolated monoclonal Tau-binding antibody or binding fragment thereof, wherein said Tau-binding antibody or binding fragment thereof comprises:
a light chain variable region comprising SEQ ID NO: 1 (CDR1), SEQ ID NO: 2 (CDR2), and SEQ ID NO: 3 (CDR3); and
a heavy chain variable region comprising SEQ ID NO: 4 (CDR1), SEQ ID NO: 5 (CDR2), and SEQ ID NO:6 (CDR3).

2. The isolated monoclonal Tau-binding antibody or binding fragment thereof of claim 1, wherein said Tau-binding antibody or binding fragment thereof comprises:
a) a light chain variable region comprising SEQ ID NO: 9 and a heavy chain variable region comprising SEQ ID NO: 10;
b) a light chain variable region comprising SEQ ID NO: 9 and a heavy chain variable region comprising SEQ ID NO: 11;
c) a light chain variable region comprising SEQ ID NO: 9 and a heavy chain variable region comprising SEQ ID NO: 12; or
d) a light chain variable region comprising SEQ ID NO: 9 and a heavy chain variable region comprising SEQ ID NO: 13.

3. The isolated monoclonal Tau-binding antibody or binding fragment thereof of claim 1, wherein the heavy chain variable region comprises SEQ ID NO: 11 or 12 or 13.

4. The isolated monoclonal Tau-binding antibody or binding fragment thereof of claim 1, wherein said Tau-binding antibody or binding fragment thereof comprises:
a light chain comprising SEQ ID NO: 14 and
a heavy chain comprising SEQ ID NO: 17 or 18.

5. The isolated monoclonal Tau-binding antibody or binding fragment thereof of claim 1, wherein said Tau-binding antibody or binding fragment thereof is a monoclonal humanized antibody.

6. An isolated nucleic acid molecule encoding the light and/or heavy chain of a Tau-binding antibody or binding fragment thereof of claim 1.

7. A cloning or expression vector comprising one or more nucleic acid molecule according to claim 6.

8. A host cell comprising one or more nucleic acid molecule according to claim 6 or a cloning or expression vector comprising one or more of said nucleic acid molecules.

9. A method of producing a Tau-binding antibody or binding fragment thereof comprising at least the steps of:
a) culturing a host cell of claim 8, and
b) isolating said Tau-binding antibody or binding fragment thereof.

10. A method of treating a tauopathy comprising administering a Tau-binding antibody or binding fragment thereof of claim 1 to a subject having a tauopathy.

11. The method of claim 10, wherein said tauopathy is Alzheimer's disease or progressive supranuclear palsy.

12. A method of diagnosing a tauopathy comprising contacting a biological sample with a Tau-binding antibody or binding fragment thereof of claim 1 and detecting the binding of said antibody to said Tau protein.

13. The method of claim 12, wherein said tauopathy is Alzheimer's disease or progressive supranuclear palsy.

14. The isolated monoclonal Tau-binding antibody or binding fragment thereof of claim 2, wherein said Tau-binding antibody or binding fragment thereof comprises a light chain variable region comprising SEQ ID NO: 9 and a heavy chain variable region comprising SEQ ID NO: 10.

15. The isolated monoclonal Tau-binding antibody or binding fragment thereof of claim 2, wherein said Tau-binding antibody or binding fragment thereof comprises a light chain variable region comprising SEQ ID NO: 9 and a heavy chain variable region comprising SEQ ID NO: 11.

16. The isolated monoclonal Tau-binding antibody or binding fragment thereof of claim 2, wherein said Tau-binding antibody or binding fragment thereof comprises a light chain variable region comprising SEQ ID NO: 9 and a heavy chain variable region comprising SEQ ID NO: 12.

17. The isolated monoclonal Tau-binding antibody or binding fragment thereof of claim 2, wherein said Tau-binding antibody or binding fragment thereof comprises a light chain variable region comprising SEQ ID NO: 9 and a heavy chain variable region comprising SEQ ID NO: 13.

18. The isolated monoclonal Tau-binding antibody or binding fragment thereof of claim 4, wherein said Tau-binding antibody or binding fragment thereof comprises a light chain comprising SEQ ID NO: 14 and a heavy chain comprising SEQ ID NO: 17.

19. The isolated monoclonal Tau-binding antibody or binding fragment thereof of claim 4, wherein said Tau-binding antibody or binding fragment thereof comprises a light chain comprising SEQ ID NO: 14 and a heavy chain comprising SEQ ID NO: 18.

20. The method of claim 11, wherein said monoclonal Tau-binding antibody or binding fragment thereof comprises a light chain variable region comprising SEQ ID NO: 9 and a heavy chain variable region comprising SEQ ID NO: 10.

21. The method of claim 11, wherein said monoclonal Tau-binding antibody or binding fragment thereof comprises a light chain variable region comprising SEQ ID NO: 9 and a heavy chain variable region comprising SEQ ID NO: 11.

22. The method of claim 11, wherein said monoclonal Tau-binding antibody or binding fragment thereof comprises a light chain variable region comprising SEQ ID NO: 9 and a heavy chain variable region comprising SEQ ID NO: 12.

23. The method of claim 11, wherein said monoclonal Tau-binding antibody or binding fragment thereof comprises a light chain variable region comprising SEQ ID NO: 9 and a heavy chain variable region comprising SEQ ID NO: 13.

24. The method of claim 11, wherein said monoclonal Tau-binding antibody or binding fragment thereof comprises a light chain comprising SEQ ID NO: 14 and a heavy chain comprising SEQ ID NO: 17.

25. The method of claim 11, wherein said monoclonal Tau-binding antibody or binding fragment thereof comprises a light chain comprising SEQ ID NO: 14 and a heavy chain comprising SEQ ID NO: 18.

26. The isolated nucleic acid molecule of claim 6, said nucleic acid molecule encoding:
   a) a light chain variable region comprising SEQ ID NO: 9;
   b) a heavy chain variable region comprising SEQ ID NO: 10;
   c) a light chain variable region comprising SEQ ID NO: 9 and a heavy chain variable region comprising SEQ ID NO: 10;
   d) a heavy chain variable region comprising SEQ ID NO: 11;
   e) a light chain variable region comprising SEQ ID NO: 9 and a heavy chain variable region comprising SEQ ID NO: 11;
   f) a heavy chain variable region comprising SEQ ID NO: 12;
   g) a light chain variable region comprising SEQ ID NO: 9 and a heavy chain variable region comprising SEQ ID NO: 12;
   h) a heavy chain variable region comprising SEQ ID NO: 13; or
   i) a light chain variable region comprising SEQ ID NO: 9 and a heavy chain variable region comprising SEQ ID NO: 13.

27. The isolated nucleic acid molecule of claim 6, said nucleic acid molecule encoding a light chain comprising SEQ ID NO: 14 and a heavy chain comprising SEQ ID NO: 17.

28. The isolated nucleic acid molecule of claim 6, said nucleic acid molecule encoding a light chain comprising SEQ ID NO: 14 and a heavy chain comprising SEQ ID NO: 18.

29. The cloning or expression vector of claim 7, said cloning or expression vector comprising a nucleic acid molecule encoding:
   a) a light chain variable region comprising SEQ ID NO: 9;
   b) a heavy chain variable region comprising SEQ ID NO: 10;
   c) a light chain variable region comprising SEQ ID NO: 9 and a heavy chain variable region comprising SEQ ID NO: 10;
   d) a heavy chain variable region comprising SEQ ID NO: 11;
   e) a light chain variable region comprising SEQ ID NO: 9 and a heavy chain variable region comprising SEQ ID NO: 11;
   f) a heavy chain variable region comprising SEQ ID NO: 12;
   g) a light chain variable region comprising SEQ ID NO: 9 and a heavy chain variable region comprising SEQ ID NO: 12;
   h) a heavy chain variable region comprising SEQ ID NO: 13; or
   i) a light chain variable region comprising SEQ ID NO: 9 and a heavy chain variable region comprising SEQ ID NO: 13.

30. The cloning or expression vector of claim 7, said cloning or expression vector comprising a nucleic acid molecule encoding a light chain comprising SEQ ID NO: 14 and a heavy chain comprising SEQ ID NO: 17.

31. The cloning or expression vector of claim 7, said cloning or expression vector comprising a nucleic acid molecule encoding a light chain comprising SEQ ID NO: 14 and a heavy chain comprising SEQ ID NO: 18.

32. A host cell comprising a nucleic acid molecule encoding:
   a) a light chain variable region comprising SEQ ID NO: 9;
   b) a heavy chain variable region comprising SEQ ID NO: 10;
   c) a light chain variable region comprising SEQ ID NO: 9 and a heavy chain variable region comprising SEQ ID NO: 10;
   d) a heavy chain variable region comprising SEQ ID NO: 11;
   e) a light chain variable region comprising SEQ ID NO: 9 and a heavy chain variable region comprising SEQ ID NO: 11;
   f) a heavy chain variable region comprising SEQ ID NO: 12;
   g) a light chain variable region comprising SEQ ID NO: 9 and a heavy chain variable region comprising SEQ ID NO: 12;
   h) a heavy chain variable region comprising SEQ ID NO: 13; or
   i) a light chain variable region comprising SEQ ID NO: 9 and a heavy chain variable region comprising SEQ ID NO: 13.

* * * * *

UNITED STATES PATENT AND TRADEMARK OFFICE
CERTIFICATE OF CORRECTION

PATENT NO. : 10,287,343 B2
APPLICATION NO. : 15/742087
DATED : May 14, 2019
INVENTOR(S) : David Edward Ormonde Knight et al.

It is certified that error appears in the above-identified patent and that said Letters Patent is hereby corrected as shown below:

In the Specification

Column 14,
Line 57, "8242" should read --R242--.

Column 15,
Line 1, "8242" should read --R242--.

Column 19,
Line 63, "Ifidium$^{192}$" should read --Iridium$^{192}$--.

Column 26,
Line 50, "Gerstmann-Stäqussler-Scheinker" should read --Gerstmann-Sträussler-Scheinker--.

Column 29,
Line 40, "8242" should read --R242--.

Column 30,
Line 22, "8242" should read --R242--.

Column 32,
Line 22, "8242" should read --R242--.

Column 36,
Line 54, "10$_1$1.1" should read --10 μl--.

Column 38,
Line 3, "100/well" should read --10μl/well--.
Line 23, "CMS" should read --CM5--.

Signed and Sealed this
First Day of October, 2019

Andrei Iancu
*Director of the United States Patent and Trademark Office*

Column 41,
Line 55, "(51)" should read --(S1)--.

Column 44,
Line 1, "(As)" should read --($\Delta\delta$)--.

SEQUENCE LISTING

<160> NUMBER OF SEQ ID NOS: 57

<210> SEQ ID NO 1
<211> LENGTH: 16
<212> TYPE: PRT
<213> ORGANISM: Rattus norvegicus

<400> SEQUENCE: 1

Arg Ser Ser Gln Ser Leu Glu Tyr Ser Asp Gly Tyr Thr Tyr Leu Glu
1               5                   10                  15

<210> SEQ ID NO 2
<211> LENGTH: 7
<212> TYPE: PRT
<213> ORGANISM: Rattus norvegicus

<400> SEQUENCE: 2

Glu Val Ser Asn Arg Phe Ser
1               5

<210> SEQ ID NO 3
<211> LENGTH: 9

```
<212> TYPE: PRT
<213> ORGANISM: Rattus norvegicus

<400> SEQUENCE: 3

Phe Gln Ala Thr His Asn Pro Tyr Thr
1               5

<210> SEQ ID NO 4
<211> LENGTH: 10
<212> TYPE: PRT
<213> ORGANISM: Rattus norvegicus

<400> SEQUENCE: 4

Gly Phe Ser Leu Thr Ser Asn Asp Ile Ala
1               5                   10

<210> SEQ ID NO 5
<211> LENGTH: 16
<212> TYPE: PRT
<213> ORGANISM: Rattus norvegicus
<220> FEATURE:
<221> NAME/KEY: misc_feature
<222> LOCATION: (12)..(12)
<223> OTHER INFORMATION: Xaa can be Ser, Ala, Thr

<400> SEQUENCE: 5

Thr Ile Trp Thr Asp Gly Ser Thr Asn Tyr Asn Xaa Ala Val Gln Ser
1               5                   10                  15

<210> SEQ ID NO 6
<211> LENGTH: 10
<212> TYPE: PRT
<213> ORGANISM: Rattus norvegicus

<400> SEQUENCE: 6

His Arg Leu Tyr Tyr Gly Ala Phe Asp Tyr
1               5                   10

<210> SEQ ID NO 7
<211> LENGTH: 112
<212> TYPE: PRT
<213> ORGANISM: Rattus norvegicus

<400> SEQUENCE: 7

Asp Ile Val Met Thr Gln Thr Pro Val Ser Leu Ser Val Thr Leu Gly
1               5                   10                  15

Asp Gln Ala Ser Ile Ser Cys Arg Ser Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asn Pro Tyr Thr Phe Gly Ala Gly Thr Lys Leu Glu Ile Lys
                100                 105                 110

<210> SEQ ID NO 8
<211> LENGTH: 117
<212> TYPE: PRT
<213> ORGANISM: Rattus norvegicus
```

```
<400> SEQUENCE: 8

Glu Val Lys Leu Glu Glu Ser Gly Pro Gly Leu Met Gln Pro Ser Glu
1               5                   10                  15

Thr Leu Ser Leu Thr Cys Thr Val Ser Gly Phe Ser Leu Thr Ser Asn
            20                  25                  30

Asp Ile Ala Trp Val Arg Gln Pro Leu Gly Lys Gly Leu Val Trp Met
        35                  40                  45

Gly Thr Ile Trp Thr Asp Gly Ser Thr Asn Tyr Asn Ser Ala Val Gln
    50                  55                  60

Ser Arg Leu Ser Ile Ser Arg Asp Thr Ser Lys Ser Gln Phe Phe Leu
65                  70                  75                  80

Lys Met Asn Ser Leu Gln Pro Glu Asp Thr Gly Thr Tyr Tyr Cys Ala
                85                  90                  95

Arg His Arg Leu Tyr Tyr Gly Ala Phe Asp Tyr Trp Gly Gln Gly Thr
            100                 105                 110

Met Val Thr Val Ser
            115

<210> SEQ ID NO 9
<211> LENGTH: 112
<212> TYPE: PRT
<213> ORGANISM: Artificial Sequence
<220> FEATURE:
<223> OTHER INFORMATION: humanized

<400> SEQUENCE: 9

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asn Pro Tyr Thr Phe Gly Gln Gly Thr Lys Leu Glu Ile Lys
            100                 105                 110

<210> SEQ ID NO 10
<211> LENGTH: 118
<212> TYPE: PRT
<213> ORGANISM: Artificial Sequence
<220> FEATURE:
<223> OTHER INFORMATION: humanized
<220> FEATURE:
<221> NAME/KEY: MISC_FEATURE
<222> LOCATION: (48)..(48)
<223> OTHER INFORMATION: Xaa can be Ile and Met
<220> FEATURE:
<221> NAME/KEY: MISC_FEATURE
<222> LOCATION: (61)..(61)
<223> OTHER INFORMATION: Xaa can be Ser, Ala, Thr

<400> SEQUENCE: 10

Glx Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Thr Ser Asn
            20                  25                  30

Asp Ile Ala Trp Ile Arg Gln Pro Pro Gly Lys Gly Leu Glu Trp Xaa
        35                  40                  45

Gly Thr Ile Trp Thr Asp Gly Ser Thr Asn Tyr Asn Xaa Ala Val Gln
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
            100                 105                 110

Met Val Thr Val Ser Ser
        115

<210> SEQ ID NO 11
<211> LENGTH: 118
<212> TYPE: PRT
<213> ORGANISM: Artificial Sequence
<220> FEATURE:
<223> OTHER INFORMATION: humanized

<400> SEQUENCE: 11

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Asp Ile Ala Trp Ile Arg Gln Pro Pro Gly Lys Gly Leu Glu Trp Met
        35                  40                  45

Gly Thr Ile Trp Thr Asp Gly Ser Thr Asn Tyr Asn Ser Ala Val Gln
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
            100                 105                 110

Met Val Thr Val Ser Ser
        115

<210> SEQ ID NO 12
<211> LENGTH: 118
<212> TYPE: PRT
<213> ORGANISM: Artificial Sequence
<220> FEATURE:
<223> OTHER INFORMATION: humanized

<400> SEQUENCE: 12

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Asp Ile Ala Trp Ile Arg Gln Pro Pro Gly Lys Gly Leu Glu Trp Met
        35                  40                  45

Gly Thr Ile Trp Thr Asp Gly Ser Thr Asn Tyr Asn Ala Ala Val Gln
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
            100                 105                 110

Met Val Thr Val Ser Ser
            115

<210> SEQ ID NO 13
<211> LENGTH: 118
<212> TYPE: PRT
<213> ORGANISM: Artificial Sequence
<220> FEATURE:
<223> OTHER INFORMATION: humanized

<400> SEQUENCE: 13

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Asp Ile Ala Trp Ile Arg Gln Pro Pro Gly Lys Gly Leu Glu Trp Met
        35                  40                  45

Gly Thr Ile Trp Thr Asp Gly Ser Thr Asn Tyr Asn Thr Ala Val Gln
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
            100                 105                 110

Met Val Thr Val Ser Ser
            115

<210> SEQ ID NO 14
<211> LENGTH: 219
<212> TYPE: PRT
<213> ORGANISM: Artificial Sequence
<220> FEATURE:
<223> OTHER INFORMATION: humanized

<400> SEQUENCE: 14

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asn Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
```

```
                130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 15
<211> LENGTH: 445
<212> TYPE: PRT
<213> ORGANISM: Artificial Sequence
<220> FEATURE:
<223> OTHER INFORMATION: humanized
<220> FEATURE:
<221> NAME/KEY: misc_feature
<222> LOCATION: (48)..(48)
<223> OTHER INFORMATION: Xaa can be Ile or Met
<220> FEATURE:
<221> NAME/KEY: misc_feature
<222> LOCATION: (61)..(61)
<223> OTHER INFORMATION: Xaa can be Ser Ala or Thr

<400> SEQUENCE: 15

Glx Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
                20                  25                  30

Asp Ile Ala Trp Ile Arg Gln Pro Pro Gly Lys Gly Leu Glu Trp Xaa
                35                  40                  45

Gly Thr Ile Trp Thr Asp Gly Ser Thr Asn Tyr Asn Xaa Ala Val Gln
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
                100                 105                 110

Met Val Thr Val Ser Ser Ala Ser Thr Lys Gly Pro Ser Val Phe Pro
                115                 120                 125

Leu Ala Pro Cys Ser Arg Ser Thr Ser Glu Ser Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205

Asn Thr Lys Val Asp Lys Arg Val Glu Ser Lys Tyr Gly Pro Pro Cys
                210                 215                 220

Pro Pro Cys Pro Ala Pro Glu Phe Leu Gly Gly Pro Ser Val Phe Leu
225                 230                 235                 240
```

```
Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 16
<211> LENGTH: 445
<212> TYPE: PRT
<213> ORGANISM: Artificial Sequence
<220> FEATURE:
<223> OTHER INFORMATION: humanized

<400> SEQUENCE: 16

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Asp Ile Ala Trp Ile Arg Gln Pro Pro Gly Lys Gly Leu Glu Trp Met
        35                  40                  45

Gly Thr Ile Trp Thr Asp Gly Ser Thr Asn Tyr Asn Ser Ala Val Gln
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160
```

-continued

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 17
<211> LENGTH: 445
<212> TYPE: PRT
<213> ORGANISM: Artificial Sequence
<220> FEATURE:
<223> OTHER INFORMATION: humanized

<400> SEQUENCE: 17

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Asp Ile Ala Trp Ile Arg Gln Pro Pro Gly Lys Gly Leu Glu Trp Met
        35                  40                  45

Gly Thr Ile Trp Thr Asp Gly Ser Thr Asn Tyr Asn Ala Ala Val Gln
    50                  55                  60

Ser Arg Val Thr Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 18
<211> LENGTH: 445
<212> TYPE: PRT
<213> ORGANISM: Artificial Sequence
<220> FEATURE:
<223> OTHER INFORMATION: humanized

<400> SEQUENCE: 18
```

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Asn
                20                  25                  30

Asp Ile Ala Trp Ile Arg Gln Pro Pro Gly Lys Gly Leu Glu Trp Met
            35                  40                  45

Gly Thr Ile Trp Thr Asp Gly Ser Thr Asn Tyr Asn Thr Ala Val Gln
 50                      55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
                100                 105                 110

Met Val Thr Val Ser Ser Ala Ser Thr Lys Gly Pro Ser Val Phe Pro
                115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Val Leu Asp Ser Asp Gly
385                 390                 395                 400

Ser Phe Phe Leu Tyr Ser Arg Leu Thr Val Asp Lys Ser Arg Trp Gln
                405                 410                 415
```

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 19
<211> LENGTH: 336
<212> TYPE: DNA
<213> ORGANISM: Rattus norvegicus

<400> SEQUENCE: 19
gatattgtga tgacccagac tccagtttcc ctgtctgtca cacttggaga tcaagcttct     60
atatcttgca ggtctagtca gagcctggaa tatagtgatg ctacacttat tttggaatgg    120
tacctacaga agccaggcca gtctcctcag ctcctcatct atgaagtttc caaccgattt    180
tctggggtcc cagacaggtt cattggcagt gggtcaggga cagatttcac cctcaagatc    240
agcagagtag agcctgagga cttggagagtt tattactgct ccaagctac acataatccg    300 tacacgtttg gagctgggac caagctggaa ataaaa                              336

<210> SEQ ID NO 20
<211> LENGTH: 354
<212> TYPE: DNA
<213> ORGANISM: Rattus norvegicus

<400> SEQUENCE: 20
gaggtgaagc tggaggagtc tggacctggc ttgatgcagc cctcagagac cctgtccctc     60
acctgcactg tctctggctt ctcactaacc agcaatgata tagcctgggt tcgacaacct    120
ctaggaaagg gtttggtgtg gatgggaaca atatggactg atggaagtac aaattataat    180
tcagctgtcc aatcccgact gagcatcagc agggacacct ccaagagcca atttttctta    240
aaaatgaaca gtctgcaacc tgaagacaca ggcacttact actgtgccag acatcgccta    300
tactacgggg ccttttgatta ctggggccaa ggaaccatgg tcaccgtctc gagt         354

<210> SEQ ID NO 21
<211> LENGTH: 336
<212> TYPE: DNA
<213> ORGANISM: Artificial Sequence
<220> FEATURE:
<223> OTHER INFORMATION: humanized

<400> SEQUENCE: 21
gatatcgtga tgactcagac cccactctca ctgtccgtca ccccgggaca gcccgcgtca     60
atctcgtgta ggagctccca atccctcgaa tactcggacg ctatacttac ctggagtgg    120 tacttgcaga agcccggaca gagcccgcag cttctgatct acgaagtgtc caacagattc    180
tccggcgtgc ctgaccgctt tcggggtcg ggctccggta ctgatttcac cctgaaaatc    240
tcccgggtgg aagccgagga cgtgggagtc tactactgct ccaagccac ccacaaccct    300 tacaccttcg gacaggggac caagctggag atcaag                              336

<210> SEQ ID NO 22
<211> LENGTH: 354
<212> TYPE: DNA
<213> ORGANISM: Artificial Sequence
<220> FEATURE:
<223> OTHER INFORMATION: humanized

<400> SEQUENCE: 22
gaggtgcagc tgcaggaatc cggtcccggc ctcgtgaagc cttcagaaac cctgtcgctc     60

```
acatgcactg tgtccgggtt ctccctgacc tctaacgaca tcgcctggat tcggcagccg    120
ccaggaaagg gactggagtg gatgggcacc atttggaccg acgggtcaac caactacaat    180
gccgcggtgc aatccagagt gaccatcagc gtggacacgt ccaagaacca gttctcgctg    240
aaattgagct ccgtgactgc cgctgatact gccgtgtatt actgtgcccg gcaccgcctt    300
tactacggcg catttgacta ctggggacag ggaaccatgg tcactgtctc gagt          354
```

<210> SEQ ID NO 23
<211> LENGTH: 354
<212> TYPE: DNA
<213> ORGANISM: Artificial Sequence
<220> FEATURE:
<223> OTHER INFORMATION: humanized

<400> SEQUENCE: 23

```
gaggtgcaac tgcaggaatc cggtcccggc ctcgtgaagc cttcagaaac cctgtcgctc     60
acatgcactg tgtccgggtt ctccctgacc tctaacgaca tcgcctggat tcggcagccg    120
ccaggaaagg gactggagtg gatgggcacc atttggaccg acgggtcaac caactacaat    180
accgcggtgc aatccagagt gaccatcagc gtggacacgt ccaagaacca gttctcgctg    240
aaattgagct ccgtgactgc cgctgatact gccgtgtatt actgtgcccg gcaccgcctt    300
tactacggcg catttgacta ctggggacag ggaaccatgg tcactgtctc gagt          354
```

<210> SEQ ID NO 24
<211> LENGTH: 657
<212> TYPE: DNA
<213> ORGANISM: Artificial Sequence
<220> FEATURE:
<223> OTHER INFORMATION: humanized

<400> SEQUENCE: 24

```
gatatcgtga tgactcagac cccactctca ctgtccgtca ccccgggaca gcccgcgtca     60
atctcgtgta ggagctccca atccctcgaa tactcggacg gctatactta cctggagtgg    120
tacttgcaga agcccggaca gagcccgcag cttctgatct acgaagtgtc caacagattc    180
tccggcgtgc ctgaccgctt ttcggggtcg ggctccggta ctgatttcac cctgaaaatc    240
tcccgggtgg aagccgagga cgtgggagtc tactactgct ccaagccac ccacaaccct    300 tacaccttcg gacaggggac caagctggag atcaagcgga ccgtggccgc tcccctccgtg   360 ttcatcttcc caccctccga cgagcagctt aagtccggca ccgcctccgt cgtgtgcctg    420
ctgaacaact ctaccccccg cgaggccaag gtgcagtgga aggtggacaa cgccctgcag    480
tccggcaact cccaggaatc cgtcaccgag caggactcca aggacagcac ctactccctg    540
tcctccaccc tgaccctgtc caaggccgac tacgagaagc acaaggtgta cgcctgcgaa    600
gtgacccacc agggcctgtc cagccccgtg accaagtcct caaccggggg cgagtgc       657
```

<210> SEQ ID NO 25
<211> LENGTH: 1335
<212> TYPE: DNA
<213> ORGANISM: Artificial Sequence
<220> FEATURE:
<223> OTHER INFORMATION: humanized

<400> SEQUENCE: 25

```
gaggtgcagc tgcaggaatc cggtcccggc ctcgtgaagc cttcagaaac cctgtcgctc     60
acatgcactg tgtccgggtt ctccctgacc tctaacgaca tcgcctggat tcggcagccg    120
```

| | |
|---|---|
| ccaggaaagg gactggagtg gatgggcacc atttggaccg acgggtcaac caactacaat | 180 |
| gccgcggtgc aatccagagt gaccatcagc gtggacacgt ccaagaacca gttctcgctg | 240 |
| aaattgagct ccgtgactgc cgctgatact gccgtgtatt actgtgcccg gcaccgcctt | 300 |
| tactacggca catttgacta ctggggacag ggaaccatgg tcactgtctc gagtgcctcc | 360 |
| accaagggcc cctccgtgtt ccctctggcc ccttgctccc ggtccacctc cgagtctacc | 420 |
| gccgctctgg gctgcctggt caaggactac ttccccgagc ccgtgacagt gtcctggaac | 480 |
| tctggcgccc tgacctccgg cgtgcacacc ttccctgccg tgctgcagtc ctccggcctg | 540 |
| tactccctgt cctccgtcgt gaccgtgccc tcctccagcc tgggcaccaa gacctacacc | 600 |
| tgtaacgtgg accacaagcc ctccaacacc aaggtggaca agcgggtgga atctaagtac | 660 |
| ggccctccct gccccccctg ccctgcccct gaatttctgg gcggaccttc cgtgttcctg | 720 |
| ttccccccaa agcccaagga caccctgatg atctcccgga ccccgaagt gacctgcgtg | 780 |
| gtggtggacg tgtcccagga agatcccgag gtccagttca attggtacgt ggacggcgtg | 840 |
| gaagtgcaca atgccaagac caagcccaga gaggaacagt tcaactccac ctaccgggtg | 900 |
| gtgtccgtgc tgaccgtgct gcaccaggac tggctgaacg gcaaagagta caagtgcaag | 960 |
| gtgtccaaca agggcctgcc ctccagcatc gaaaagacca ctctccaaggc caagggccag | 1020 |
| ccccgcgagc cccaggtgta caccctgccc cctagccagg aagagatgac caagaaccag | 1080 |
| gtgtccctga cctgtctggt caagggcttc taccctccc acattgccgt ggaatgggag | 1140 |
| tccaacggcc agcccgagaa caactacaag accaccccc ctgtgctgga cagcgacggc | 1200 |
| tccttcttcc tgtactctcg gctgaccgtg gacaagtccc ggtggcagga aggcaacgtc | 1260 |
| ttctcctgct ccgtgatgca cgaggccctg cacaaccact acacccagaa gtccctgtcc | 1320 |
| ctgagcctgg gcaag | 1335 |

<210> SEQ ID NO 26
<211> LENGTH: 1335
<212> TYPE: DNA
<213> ORGANISM: Artificial Sequence
<220> FEATURE:
<223> OTHER INFORMATION: humanized

<400> SEQUENCE: 26

| | |
|---|---|
| gaggtgcaac tgcaggaatc cggtcccggc ctcgtgaagc cttcagaaac cctgtcgctc | 60 |
| acatgcactg tgtccgggtt ctccctgacc tctaacgaca tcgcctggat tcggcagccg | 120 |
| ccaggaaagg gactggagtg gatgggcacc atttggaccg acgggtcaac caactacaat | 180 |
| accgcggtgc aatccagagt gaccatcagc gtggacacgt ccaagaacca gttctcgctg | 240 |
| aaattgagct ccgtgactgc cgctgatact gccgtgtatt actgtgcccg gcaccgcctt | 300 |
| tactacggcg catttgacta ctggggacag ggaaccatgg tcactgtctc gagtgcctcc | 360 |
| accaagggcc cctccgtgtt ccctctggcc ccttgctccc ggtccacctc cgagtctacc | 420 |
| gccgctctgg gctgcctggt caaggactac ttccccgagc ccgtgacagt gtcctggaac | 480 |
| tctggcgccc tgacctccgg cgtgcacacc ttccctgccg tgctgcagtc ctccggcctg | 540 |
| tactccctgt cctccgtcgt gaccgtgccc tcctccagcc tgggcaccaa gacctacacc | 600 |
| tgtaacgtgg accacaagcc ctccaacacc aaggtggaca agcgggtgga atctaagtac | 660 |
| ggccctccct gccccccctg ccctgcccct gaatttctgg gcggaccttc cgtgttcctg | 720 |
| ttccccccaa agcccaagga caccctgatg atctcccgga ccccgaagt gacctgcgtg | 780 |
| gtggtggacg tgtcccagga agatcccgag gtccagttca attggtacgt ggacggcgtg | 840 |

```
gaagtgcaca atgccaagac caagcccaga gaggaacagt tcaactccac ctaccgggtg    900
gtgtccgtgc tgaccgtgct gcaccaggac tggctgaacg gcaaagagta caagtgcaag    960
gtgtccaaca agggcctgcc ctccagcatc gaaaagacca tctccaaggc caagggccag   1020
ccccgcgagc cccaggtgta caccctgccc ctagccagga agagatgacc aagaaccag    1080
gtgtccctga cctgtctggt caagggcttc taccctccg acattgccgt ggaatgggag   1140
tccaacggcc agcccgagaa caactacaag accaccccc ctgtgctgga cagcgacggc   1200
tccttcttcc tgtactctcg gctgaccgtg gacaagtccc ggtggcagga aggcaacgtc   1260
ttctcctgct ccgtgatgca cgaggccctg cacaaccact acacccagaa gtccctgtcc   1320
ctgagcctgg gcaag                                                    1335
```

<210> SEQ ID NO 27
<211> LENGTH: 134
<212> TYPE: PRT
<213> ORGANISM: Rattus norvegicus
<220> FEATURE:
<221> NAME/KEY: MISC_FEATURE
<222> LOCATION: (1)..(22)
<223> OTHER INFORMATION: leader sequence

<400> SEQUENCE: 27

```
Met Asp Met Arg Val Pro Ala Gln Val Phe Gly Phe Leu Leu Leu Trp
1               5                   10                  15
Phe Pro Gly Thr Arg Cys Asp Ile Val Met Thr Gln Thr Pro Val Ser
            20                  25                  30
Leu Ser Val Thr Leu Gly Asp Gln Ala Ser Ile Ser Cys Arg Ser Ser
        35                  40                  45
Gln Ser Leu Glu Tyr Ser Asp Gly Tyr Thr Tyr Leu Glu Trp Tyr Leu
    50                  55                  60
Gln Lys Pro Gly Gln Ser Pro Gln Leu Leu Ile Tyr Glu Val Ser Asn
65                  70                  75                  80
Arg Phe Ser Gly Val Pro Asp Arg Phe Ile Gly Ser Gly Ser Gly Thr
                85                  90                  95
Asp Phe Thr Leu Lys Ile Ser Arg Val Glu Pro Glu Asp Leu Gly Val
            100                 105                 110
Tyr Tyr Cys Phe Gln Ala Thr His Asn Pro Tyr Thr Phe Gly Ala Gly
        115                 120                 125
Thr Lys Leu Glu Ile Lys
    130
```

<210> SEQ ID NO 28
<211> LENGTH: 136
<212> TYPE: PRT
<213> ORGANISM: Rattus norvegicus

<400> SEQUENCE: 28

```
Met Glu Trp Ser Trp Val Phe Leu Phe Phe Leu Ser Val Thr Thr Gly
1               5                   10                  15
Val His Ser Glu Val Lys Leu Glu Glu Ser Gly Pro Gly Leu Met Gln
            20                  25                  30
Pro Ser Glu Thr Leu Ser Leu Thr Cys Thr Val Ser Gly Phe Ser Leu
        35                  40                  45
Thr Ser Asn Asp Ile Ala Trp Val Arg Gln Pro Leu Gly Lys Gly Leu
    50                  55                  60
Val Trp Met Gly Thr Ile Trp Thr Asp Gly Ser Thr Asn Tyr Asn Ser
```

```
                65                  70                  75                  80
Ala Val Gln Ser Arg Leu Ser Ile Ser Arg Asp Thr Ser Lys Ser Gln
                    85                  90                  95

Phe Phe Leu Lys Met Asn Ser Leu Gln Pro Glu Asp Thr Gly Thr Tyr
                100                 105                 110

Tyr Cys Ala Arg His Arg Leu Tyr Tyr Gly Ala Phe Asp Tyr Trp Gly
        115                 120                 125

Gln Gly Thr Met Val Thr Val Ser
    130                 135

<210> SEQ ID NO 29
<211> LENGTH: 402
<212> TYPE: DNA
<213> ORGANISM: Rattus norvegicus
<220> FEATURE:
<221> NAME/KEY: misc_feature
<222> LOCATION: (1)..(66)
<223> OTHER INFORMATION: leader sequence

<400> SEQUENCE: 29
atggacatga gggttcctgc tcaggttttt ggcttcttgt tgctctggtt tccaggcacc      60
aggtgtgata ttgtgatgac ccagactcca gtttccctgt ctgtcacact ggagatcaa     120 gcttctatat cttgcaggtc tagtcagagc ctggaatata gtgatggcta cacttatttg     180
gaatggtacc tacagaagcc aggccagtct cctcagctcc tcatctatga gtttccaac     240 cgattttctg ggtcccaga caggttcatt ggcagtgggt cagggacaga tttcaccctc     300
aagatcagca gagtagagcc tgaggacttg ggagtttatt actgcttcca agctacacat     360
aatccgtaca cgtttggagc tgggaccaag ctggaaataa aa                        402

<210> SEQ ID NO 30
<211> LENGTH: 411
<212> TYPE: DNA
<213> ORGANISM: Rattus norvegicus
<220> FEATURE:
<221> NAME/KEY: misc_feature
<222> LOCATION: (1)..(57)
<223> OTHER INFORMATION: leader sequence

<400> SEQUENCE: 30
atggaatgga gctgggtctt tctcttcttc ctgtcagtaa ctaccggtgt ccattctgag      60
gtgaagctgg aggagtctgg acctggcttg atgcagccct cagagaccct gtccctcacc     120
tgcactgtct ctggcttctc actaaccagc aatgatatag cctgggttcg acaacctcta     180
ggaaagggtt tggtgtggat gggaacaata tggactgatg gaagtacaaa ttataattca     240
gctgtccaat cccgactgag catcagcagg gacacctcca gagccaatt tttcttaaaa     300 atgaacagtc tgcaacctga agacacaggc acttactact gtgccagaca tcgcctatac     360
tacggggcct tgattactg gggccaagga accatggtca ccgtctcgag t              411

<210> SEQ ID NO 31
<211> LENGTH: 112
<212> TYPE: PRT
<213> ORGANISM: Homo sapiens

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30
```

Asp Gly Lys Thr Tyr Leu Tyr Trp Tyr Leu Gln Lys Pro Gly Gln Ser
            35                  40                  45

Pro Gln Leu Leu Ile Tyr Glu Val Ser Ser Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro Tyr Thr Phe Gly Gln Gly Thr Lys Leu Glu Ile Lys
            100                 105                 110

<210> SEQ ID NO 32
<211> LENGTH: 113
<212> TYPE: PRT
<213> ORGANISM: Homo sapiens

<400> SEQUENCE: 32

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Ala Phe Asp Val Trp Gly Gln Gly Thr Met Val Thr Val Ser
            100                 105                 110

Ser

<210> SEQ ID NO 33
<211> LENGTH: 336
<212> TYPE: DNA
<213> ORGANISM: Homo sapiens

<400> SEQUENCE: 33
gatattgtga tgacccagac tccactctct ctgtccgtca cccctggaca gccggcctcc      60
atctcctgca agtctagtca gagcctcctg catagtgatg aaagaccta tttgtattgg     120 tacctgcaga agccaggcca gtctccacag ctcctaatct atgaagtttc agccggttc     180 tctggagtgc cagataggtt cagtggcagc gggtcaggga cagatttcac actgaaaatc     240
agccgggtgg aggctgagga tgttggggtt tattactgca tgcaaggtat acaccttcct     300 tacactttg gccaggggac caagctggag atcaaa                               336

<210> SEQ ID NO 34
<211> LENGTH: 339
<212> TYPE: DNA
<213> ORGANISM: Homo sapiens

<400> SEQUENCE: 34
caggtgcagc tgcaggagtc gggcccagga ctggtgaagc cttcggagac cctgtccctc      60
acctgcactg tctctggtgg ctccatcagt agttactact ggagctggat ccggcagccc     120

```
ccagggaagg gactggagtg gattgggtat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag agatgctttt     300
gatgtctggg gccaagggac aatggtcacc gtctcttca                            339
```

<210> SEQ ID NO 35
<211> LENGTH: 441
<212> TYPE: PRT
<213> ORGANISM: Homo sapiens

<400> SEQUENCE: 35

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335
```

```
Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 36
<211> LENGTH: 16
<212> TYPE: PRT
<213> ORGANISM: Rattus norvegicus

<400> SEQUENCE: 36

Thr Ile Trp Thr Asp Gly Ser Thr Asn Tyr Asn Ser Ala Val Gln Ser
1               5                   10                  15

<210> SEQ ID NO 37
<211> LENGTH: 16
<212> TYPE: PRT
<213> ORGANISM: Rattus norvegicus

<400> SEQUENCE: 37

Thr Ile Trp Thr Asp Gly Ser Thr Asn Tyr Asn Ala Ala Val Gln Ser
1               5                   10                  15

<210> SEQ ID NO 38
<211> LENGTH: 16
<212> TYPE: PRT
<213> ORGANISM: Rattus norvegicus

<400> SEQUENCE: 38

Thr Ile Trp Thr Asp Gly Ser Thr Asn Tyr Asn Thr Ala Val Gln Ser
1               5                   10                  15

<210> SEQ ID NO 39
<211> LENGTH: 6757
<212> TYPE: DNA
<213> ORGANISM: Artificial Sequence
<220> FEATURE:
<223> OTHER INFORMATION: synthetic

<400> SEQUENCE: 39
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aacccatctc ggtctattc      360 ttttgattta taagggattt tgccgatttc ggcctattgg ttaaaaaatg agctgattta     420
acaaaaattt aacgcgaatt ttaacaaaat attaacgttt acaatttcag gtggcacttt     480
```

```
tcggggaaat gtgcgcggaa cccctatttg tttattttc taaatacatt caaatatgta    540
tccgctcatg agacaataac cctgataaat gcttcaataa tattgaaaaa ggaagagtat    600
gagtattcaa catttccgtg tcgcccttat tccctttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacgatggc atgacagtaa gagaattatg    960
cagtgctgcc ataaccatga gtgataacac tgcggccaac ttacttctga acgatcgg    1020 aggaccgaag gagctaaccg ctttttgca acatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca gtttactca tatatacttt agattgattt    1500
aaaacttcat ttttaattta aaaggatcta ggtgaagatc cttttttgata atctcatgac    1560 caaaatccct taacgtgagt tttcgttcca ctgagcgtca gaccccgtag aaaagatcaa    1620
aggatcttct tgagatcctt ttttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtccctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggccttttg ctcacatgtt    2280
ctttcctgcg ttatccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
```

```
ttttttcctg tttggtcact gatgcctccg tgtaaggggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattat gttgttgctc aggtcgcag     3180 acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg cgataatgg cctgcttctc gccgaaacgt ttggtggcgg     3360
gaccagtgac gaaggcttga cgagggcgt gcaagattcc gaataccgca agcgacaggc     3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagatg tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg caacgccaa tcagcaacga ctgtttgccc     4560
gccagttgtt gtgccacgcg gttgggaatg taattcagct ccgccatcgc cgcttccact    4620 tttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg cgctatcat gccataccgc gaaaggtttt gcgccattcg    4800
atggtgtccg ggatctcgac gctctcccct atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccatacc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
cgatctcgat cccgcgaaat taatacgact cactataggg gaattgtgag cggataacaa    5160
ttcccctcta gaaataattt tgtttaactt taagaaggag atatacatat gggctcaagc    5220
```

-continued

```
caccaccacc accaccacag cagcggcgag aacttgtact ttcaaggatc cgcagaacca    5280
cgtcaagaat ttgaggttat ggaagatcac gcgggcactt acggtttggg tgatcgtaaa    5340
gaccagggcg gctataccat gcatcaagat caagagggcg acaccgatgc tggcttgaaa    5400
gagtcgccgc tgcagactcc gaccgaggat ggcagcgaag agccgggcag cgagactagc    5460
gatgcgaagt cgaccccgac cgccgaggac gttaccgcac cgctggtcga cgagggtgct    5520
ccgggtaaac aggcggctgc acagccgcac acggagattc cggaaggcac caccgcagaa    5580
gaggcgggta tcggcgacac tccgtccctg aagatgaggc agccggtca tgtcacgcag    5640 gcgcgtatgg tgagcaagag caaagatggt acgggtagcg acgacaagaa ggcgaagggc    5700
gcagatggca agaccaaaat tgcgacgccg cgtggtgcgg caccgccagg ccagaaaggt    5760
caggcgaatg ccacgcgcat cccggcaaag acgccaccgg ctccgaaaac cccgccttcc    5820
agcggtgaac cgccgaaatc cggtgaccgc agcggttata gctctccggg tagcccgggt    5880
accccaggca gccgtagccg caccccgagc ctgccgaccc caccgacccg cgagccgaag    5940
aaagtggcgg tggttcgtac gccgccaaaa agcccgagct ctgccaagag ccgtctgcaa    6000
accgctcctg tgccgatgcc ggacctgaag aacgttaagt ctaaaatcgg tagcaccgaa    6060
aatctgaagc accaacctgg tggcggtaag gttcaaatca tcaacaaaaa gctggacttg    6120
agcaatgtac aaagcaagtg tggtagcaag gacaatatca acacgtccc gggtggtggt    6180 tccgtccaga ttgtgtacaa accggtggac ctgagcaagg ttaccagcaa atgcggttcc    6240
ctgggtaaca tccatcataa accgggtggc ggccaagttg aggtcaagag cgagaaactg    6300
gacttcaaag accgcgttca gtccaaaatc ggttctctgg acaacattac gcacgtgcct    6360
ggtggtggca caagaagat tgaaacccat aaactgacgt ttcgtgaaaa tgcgaaggcg    6420
aaaaccgacc acggcgcaga gattgtctac aaaagcccgg tggtgagcgg tgataccagc    6480
ccgcgtcacc tgtccaacgt cagcagcacg ggcagcattg atatggtgga tagcccgcag    6540
ttggctacgc tggccgatga ggttagcgcg agcctggcga agcagggtct gtgactcgag    6600
caccaccacc accaccactg agatccggct gctaacaaag cccgaaagga agctgagttg    6660
gctgctgcca ccgctgagca ataactagca taacccttg gggcctctaa acgggtcttg    6720
aggggttttt tgctgaaagg aggaactata tccggat                             6757
```

<210> SEQ ID NO 40
<211> LENGTH: 461
<212> TYPE: PRT
<213> ORGANISM: Artificial Sequence
<220> FEATURE:
<223> OTHER INFORMATION: synthetic

<400> SEQUENCE: 40

Met Gly Ser Ser His His His His His Ser Ser Gly Glu Asn Leu
1               5                   10                  15

Tyr Phe Gln Gly Ser Ala Glu Pro Arg Gln Glu Phe Glu Val Met Glu
            20                  25                  30

Asp His Ala Gly Thr Tyr Gly Leu Gly Asp Arg Lys Asp Gln Gly Gly
        35                  40                  45

Tyr Thr Met His Gln Asp Gln Glu Gly Asp Thr Asp Ala Gly Leu Lys
    50                  55                  60

Glu Ser Pro Leu Gln Thr Pro Thr Glu Asp Gly Ser Glu Glu Pro Gly
65                  70                  75                  80

Ser Glu Thr Ser Asp Ala Lys Ser Thr Pro Thr Ala Glu Asp Val Thr

```
            85                  90                  95
Ala Pro Leu Val Asp Glu Gly Ala Pro Gly Lys Gln Ala Ala Gln
            100                 105                 110

Pro His Thr Glu Ile Pro Glu Gly Thr Thr Ala Glu Glu Ala Gly Ile
            115                 120                 125

Gly Asp Thr Pro Ser Leu Glu Asp Glu Ala Ala Gly His Val Thr Gln
        130                 135                 140

Ala Arg Met Val Ser Lys Ser Lys Asp Gly Thr Gly Ser Asp Asp Lys
145                 150                 155                 160

Lys Ala Lys Gly Ala Asp Gly Lys Thr Lys Ile Ala Thr Pro Arg Gly
                165                 170                 175

Ala Ala Pro Pro Gly Gln Lys Gly Gln Ala Asn Ala Thr Arg Ile Pro
            180                 185                 190

Ala Lys Thr Pro Pro Ala Pro Lys Thr Pro Pro Ser Ser Gly Glu Pro
        195                 200                 205

Pro Lys Ser Gly Asp Arg Ser Gly Tyr Ser Ser Pro Gly Ser Pro Gly
        210                 215                 220

Thr Pro Gly Ser Arg Ser Arg Thr Pro Ser Leu Pro Thr Pro Pro Thr
225                 230                 235                 240

Arg Glu Pro Lys Lys Val Ala Val Val Arg Thr Pro Pro Lys Ser Pro
                245                 250                 255

Ser Ser Ala Lys Ser Arg Leu Gln Thr Ala Pro Val Pro Met Pro Asp
            260                 265                 270

Leu Lys Asn Val Lys Ser Lys Ile Gly Ser Thr Glu Asn Leu Lys His
        275                 280                 285

Gln Pro Gly Gly Gly Lys Val Gln Ile Ile Asn Lys Lys Leu Asp Leu
        290                 295                 300

Ser Asn Val Gln Ser Lys Cys Gly Ser Lys Asp Asn Ile Lys His Val
305                 310                 315                 320

Pro Gly Gly Gly Ser Val Gln Ile Val Tyr Lys Pro Val Asp Leu Ser
                325                 330                 335

Lys Val Thr Ser Lys Cys Gly Ser Leu Gly Asn Ile His His Lys Pro
            340                 345                 350

Gly Gly Gly Gln Val Glu Val Lys Ser Glu Lys Leu Asp Phe Lys Asp
        355                 360                 365

Arg Val Gln Ser Lys Ile Gly Ser Leu Asp Asn Ile Thr His Val Pro
        370                 375                 380

Gly Gly Gly Asn Lys Lys Ile Glu Thr His Lys Leu Thr Phe Arg Glu
385                 390                 395                 400

Asn Ala Lys Ala Lys Thr Asp His Gly Ala Glu Ile Val Tyr Lys Ser
                405                 410                 415

Pro Val Val Ser Gly Asp Thr Ser Pro Arg His Leu Ser Asn Val Ser
            420                 425                 430

Ser Thr Gly Ser Ile Asp Met Val Asp Ser Pro Gln Leu Ala Thr Leu
        435                 440                 445

Ala Asp Glu Val Ser Ala Ser Leu Ala Lys Gln Gly Leu
450                 455                 460

<210> SEQ ID NO 41
<211> LENGTH: 442
<212> TYPE: PRT
<213> ORGANISM: Artificial Sequence
<220> FEATURE:
<223> OTHER INFORMATION: synthetic
```

<400> SEQUENCE: 41

```
Gly Ser Ala Glu Pro Arg Gln Glu Phe Glu Val Met Glu Asp His Ala
1               5                   10                  15

Gly Thr Tyr Gly Leu Gly Asp Arg Lys Asp Gln Gly Gly Tyr Thr Met
            20                  25                  30

His Gln Asp Gln Glu Gly Asp Thr Asp Ala Gly Leu Lys Glu Ser Pro
        35                  40                  45

Leu Gln Thr Pro Thr Glu Asp Gly Ser Glu Glu Pro Gly Ser Glu Thr
    50                  55                  60

Ser Asp Ala Lys Ser Thr Pro Thr Ala Glu Asp Val Thr Ala Pro Leu
65                  70                  75                  80

Val Asp Glu Gly Ala Pro Gly Lys Gln Ala Ala Gln Pro His Thr
                85                  90                  95

Glu Ile Pro Glu Gly Thr Thr Ala Glu Glu Ala Gly Ile Gly Asp Thr
                100                 105                 110

Pro Ser Leu Glu Asp Glu Ala Ala Gly His Val Thr Gln Ala Arg Met
            115                 120                 125

Val Ser Lys Ser Lys Asp Gly Thr Gly Ser Asp Asp Lys Lys Ala Lys
130                 135                 140

Gly Ala Asp Gly Lys Thr Lys Ile Ala Thr Pro Arg Gly Ala Ala Pro
145                 150                 155                 160

Pro Gly Gln Lys Gly Gln Ala Asn Ala Thr Arg Ile Pro Ala Lys Thr
                165                 170                 175

Pro Pro Ala Pro Lys Thr Pro Pro Ser Ser Gly Glu Pro Pro Lys Ser
            180                 185                 190

Gly Asp Arg Ser Gly Tyr Ser Ser Pro Gly Ser Pro Gly Thr Pro Gly
            195                 200                 205

Ser Arg Ser Arg Thr Pro Ser Leu Pro Thr Pro Pro Thr Arg Glu Pro
210                 215                 220

Lys Lys Val Ala Val Arg Thr Pro Pro Lys Ser Pro Ser Ser Ala
225                 230                 235                 240

Lys Ser Arg Leu Gln Thr Ala Pro Val Pro Met Pro Asp Leu Lys Asn
                245                 250                 255

Val Lys Ser Lys Ile Gly Ser Thr Glu Asn Leu Lys His Gln Pro Gly
                260                 265                 270

Gly Gly Lys Val Gln Ile Ile Asn Lys Lys Leu Asp Leu Ser Asn Val
            275                 280                 285

Gln Ser Lys Cys Gly Ser Lys Asp Asn Ile Lys His Val Pro Gly Gly
290                 295                 300

Gly Ser Val Gln Ile Val Tyr Lys Pro Val Asp Leu Ser Lys Val Thr
305                 310                 315                 320

Ser Lys Cys Gly Ser Leu Gly Asn Ile His His Lys Pro Gly Gly Gly
                325                 330                 335

Gln Val Glu Val Lys Ser Glu Lys Leu Asp Phe Lys Asp Arg Val Gln
            340                 345                 350

Ser Lys Ile Gly Ser Leu Asp Asn Ile Thr His Val Pro Gly Gly Gly
            355                 360                 365

Asn Lys Lys Ile Glu Thr His Lys Leu Thr Phe Arg Glu Asn Ala Lys
            370                 375                 380

Ala Lys Thr Asp His Gly Ala Glu Ile Val Tyr Lys Ser Pro Val Val
385                 390                 395                 400

Ser Gly Asp Thr Ser Pro Arg His Leu Ser Asn Val Ser Ser Thr Gly
            405                 410                 415
```

Ser Ile Asp Met Val Asp Ser Pro Gln Leu Ala Thr Leu Ala Asp Glu
    420                 425                 430

Val Ser Ala Ser Leu Ala Lys Gln Gly Leu
    435                 440

<210> SEQ ID NO 42
<211> LENGTH: 6583
<212> TYPE: DNA
<213> ORGANISM: Artificial Sequence
<220> FEATURE:
<223> OTHER INFORMATION: synthetic

<400> SEQUENCE: 42

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt tcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt ttttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
```

-continued

```
agtggctgct gccagtggcg ataagtcgtg tcttaccggg ttggactcaa gacgatagtt  1920
accggataag gcgcagcggt cgggctgaac gggggttcg tgcacacagc ccagcttgga   1980
gcgaacgacc tacaccgaac tgagatacct acagcgtgag ctatgagaaa gcgccacgct  2040
tcccgaaggg agaaaggcgg acaggtatcc ggtaagcggc agggtcggaa caggagagcg  2100
cacgagggag cttccagggg gaaacgcctg gtatctttat agtcctgtcg ggtttcgcca  2160
cctctgactt gagcgtcgat ttttgtgatg ctcgtcaggg gggcggagcc tatggaaaaa  2220
cgccagcaac gcggccttt tacggttcct ggccttttgc tggccttttg ctcacatgtt   2280
ctttcctgcg ttatccctg attctgtgga taaccgtatt accgcctttg agtgagctga    2340
taccgctcgc cgcagccgaa cgaccgagcg cagcgagtca gtgagcgagg aagcggaaga  2400
gcgcctgatg cggtattttc tccttacgca tctgtgcggt atttcacacc gcatatatgg  2460
tgcactctca gtacaatctg ctctgatgcc gcatagttaa ccagtatac actccgctat    2520 cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaagggg atttctgttc atggggtaa    2880 tgataccgat gaaacgagag aggatgctca cgatacgggt tactgatgat gaacatgccc   2940
ggttactgga acgttgtgag ggtaaacaac tggcggtatg gatgcggcgg gaccagaaa    3000 aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300
cccgtggggc cgccatgccg gcgataatgg cctgcttctc gccgaaacgt ttggtggcgg   3360
gaccagtgac gaaggcttga gcgagggcgt gcaagattcc gaataccgca agcgacaggc   3420
cgatcatcgt cgcgctccag cgaaagcggt cctcgccgaa aatgacccag agcgctgccg   3480
gcacctgtcc tacgagttgc atgataaaga agacagtcat aagtgcggcg acgatagtca   3540
tgccccgcgc ccaccggaag gagctgactg ggttgaaggc tctcaagggc atcggtcgag   3600
atcccggtgc ctaatgagtg agctaactta cattaattgc gttgcgctca ctgcccgctt   3660
tccagtcggg aaacctgtcg tgccagctgc attaatgaat cggccaacgc gcggggagag   3720
gcggtttgcg tattgggcgc cagggtggtt tttcttttca ccagtgagac gggcaacagc   3780
tgattgccct tcaccgcctg gccctgagag agttgcagca agcggtccac gctggtttgc   3840
cccagcaggc gaaaatcctg tttgatggtg gttaacggcg ggatataaca tgagctgtct   3900
tcggtatcgt cgtatcccac taccgagatg tccgcaccaa cgcgcagccc ggactcggta   3960
atggcgcgca ttgcgcccag cgccatctga tcgttggcaa ccagcatcgc agtgggaacg   4020
atgccctcat tcagcatttg catggtttgt tgaaaaccgg acatggcact ccagtcgcct   4080
tcccgttccg ctatcggctg aatttgattg cgagtgagat atttatgcca gccagccaga   4140
cgcagacgcg ccgagacaga acttaatggg cccgctaaca gcgcgatttg ctggtgaccc   4200
aatgcgacca gatgctccac gcccagtcgc gtaccgtctt catgggagaa aataatactg   4260
```

```
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga acggtctga    4680
taagagacac cggcatactc tgcgacatcg tataacgtta ctggtttcac attcaccacc    4740
ctgaattgac tctcttccgg gcgctatcat gccataccgc gaaaggtttt cgcgccattcg   4800
atggtgtccg gatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
cgatctcgat cccgcgaaat taatacgact cactataggg gaattgtgag cggataacaa    5160
ttcccctcta gaaataattt tgtttaactt taagaaggag atatacatat gggctcaagc    5220
caccaccacc accaccacag cagcggcgag aacttgtact ttcaaggatc cgcagaacca    5280
cgtcaagaat ttgaggttat ggaagatcac gcgggcactt acggtttggg tgatcgtaaa    5340
gaccagggcg gctataccat gcatcaagat caagagggcg acaccgatgc tggcttgaaa    5400
gcagaagagg cgggtatcgg cgacactccg tccctggaag atgaggcagc cggtcatgtc    5460
acgcaggcgc gtatggtgag caagagcaaa gatggtacgg gtagcgacga caagaaggcg    5520
aagggcgcag atggcaagac caaaattgcg acgccgcgtg gtgcggcacc gccaggccag    5580
aaaggtcagg cgaatgccac gcgcatcccg gcaaagacgc caccggctcc gaaaaccccg    5640
ccttccagcg gtgaaccgcc gaaatccggt gaccgcagcg gttatagctc tccgggtagc    5700
ccgggtaccc caggcagccg tagccgcacc ccgagcctgc cgaccccacc gacccgcgag    5760
ccgaagaaag tggcggtggt tcgtacgccg ccaaaaagcc cgagctctgc caagagccgt    5820
ctgcaaaccg ctcctgtgcc gatgccggac ctgaagaacg ttaagtctaa aatcggtagc    5880
accgaaaatc tgaagcacca acctggtggc ggtaaggttc aaatcatcaa caaaaagctg    5940
gacttgagca atgtacaaag caagtgtggt agcaaggaca atatcaaaca cgtcccgggt    6000
ggtggttccg tccagattgt gtacaaaccg gtggacctga gcaaggttac cagcaaatgc    6060
ggttccctgg gtaacatcca tcataaaccg ggtggcggcc aagttgaggt caagagcgag    6120
aaactggact tcaaagaccg cgttcagtcc aaaatcggtt ctctggacaa cattacgcac    6180
gtgcctggtg gtggcaacaa gaagattgaa acccataaac tgacgtttcg tgaaaatgcg    6240
aaggcgaaaa ccgaccacgg cgcagagatt gtctacaaaa gcccggtggt gagcggtgat    6300
accagcccgc gtcacctgtc caacgtcagc agcacgggca gcattgatat ggtggatagc    6360
ccgcagttgg ctacgctggc cgatgaggtt agcgcgagcc tggcgaagca gggtctgtga    6420
ctcgagcacc accaccacca ccactgagat ccggctgcta acaaagcccg aaaggaagct    6480
gagttggctg ctgccaccgc tgagcaataa ctagcataac cccttggggc ctctaaacgg    6540
gtcttgaggg gttttttgct gaaaggagga actatatccg gat                      6583
```

<210> SEQ ID NO 43
<211> LENGTH: 403
<212> TYPE: PRT
<213> ORGANISM: Artificial Sequence
<220> FEATURE:
<223> OTHER INFORMATION: synthetic

<400> SEQUENCE: 43

```
Met Gly Ser Ser His His His His His Ser Ser Gly Glu Asn Leu
1               5                   10                  15

Tyr Phe Gln Gly Ser Ala Glu Pro Arg Gln Glu Phe Glu Val Met Glu
            20                  25                  30

Asp His Ala Gly Thr Tyr Gly Leu Gly Asp Arg Lys Asp Gln Gly Gly
        35                  40                  45

Tyr Thr Met His Gln Asp Gln Glu Gly Asp Thr Asp Ala Gly Leu Lys
    50                  55                  60

Ala Glu Glu Ala Gly Ile Gly Asp Thr Pro Ser Leu Glu Asp Glu Ala
65                  70                  75                  80

Ala Gly His Val Thr Gln Ala Arg Met Val Ser Lys Ser Lys Asp Gly
                85                  90                  95

Thr Gly Ser Asp Asp Lys Lys Ala Lys Gly Ala Asp Gly Lys Thr Lys
            100                 105                 110

Ile Ala Thr Pro Arg Gly Ala Ala Pro Pro Gly Gln Lys Gly Gln Ala
        115                 120                 125

Asn Ala Thr Arg Ile Pro Ala Lys Thr Pro Pro Ala Pro Lys Thr Pro
    130                 135                 140

Pro Ser Ser Gly Glu Pro Pro Lys Ser Gly Asp Arg Ser Gly Tyr Ser
145                 150                 155                 160

Ser Pro Gly Ser Pro Gly Thr Pro Gly Ser Arg Ser Arg Thr Pro Ser
                165                 170                 175

Leu Pro Thr Pro Pro Thr Arg Glu Pro Lys Lys Val Ala Val Val Arg
            180                 185                 190

Thr Pro Pro Lys Ser Pro Ser Ser Ala Lys Ser Arg Leu Gln Thr Ala
        195                 200                 205

Pro Val Pro Met Pro Asp Leu Lys Asn Val Lys Ser Lys Ile Gly Ser
    210                 215                 220

Thr Glu Asn Leu Lys His Gln Pro Gly Gly Gly Lys Val Gln Ile Ile
225                 230                 235                 240

Asn Lys Lys Leu Asp Leu Ser Asn Val Gln Ser Lys Cys Gly Ser Lys
                245                 250                 255

Asp Asn Ile Lys His Val Pro Gly Gly Gly Ser Val Gln Ile Val Tyr
            260                 265                 270

Lys Pro Val Asp Leu Ser Lys Val Thr Ser Lys Cys Gly Ser Leu Gly
        275                 280                 285

Asn Ile His His Lys Pro Gly Gly Gly Gln Val Glu Val Lys Ser Glu
    290                 295                 300

Lys Leu Asp Phe Lys Asp Arg Val Gln Ser Lys Ile Gly Ser Leu Asp
305                 310                 315                 320

Asn Ile Thr His Val Pro Gly Gly Gly Asn Lys Lys Ile Glu Thr His
                325                 330                 335

Lys Leu Thr Phe Arg Glu Asn Ala Lys Ala Lys Thr Asp His Gly Ala
            340                 345                 350

Glu Ile Val Tyr Lys Ser Pro Val Val Ser Gly Asp Thr Ser Pro Arg
        355                 360                 365
```

```
His Leu Ser Asn Val Ser Ser Thr Gly Ser Ile Asp Met Val Asp Ser
    370                 375                 380

Pro Gln Leu Ala Thr Leu Ala Asp Glu Val Ser Ala Ser Leu Ala Lys
385                 390                 395                 400

Gln Gly Leu

<210> SEQ ID NO 44
<211> LENGTH: 384
<212> TYPE: PRT
<213> ORGANISM: Artificial Sequence
<220> FEATURE:
<223> OTHER INFORMATION: synthetic

<400> SEQUENCE: 44

Gly Ser Ala Glu Pro Arg Gln Glu Phe Glu Val Met Glu Asp His Ala
1               5                   10                  15

Gly Thr Tyr Gly Leu Gly Asp Arg Lys Asp Gln Gly Gly Tyr Thr Met
            20                  25                  30

His Gln Asp Gln Glu Gly Asp Thr Asp Ala Gly Leu Lys Ala Glu Glu
        35                  40                  45

Ala Gly Ile Gly Asp Thr Pro Ser Leu Glu Asp Glu Ala Ala Gly His
    50                  55                  60

Val Thr Gln Ala Arg Met Val Ser Lys Ser Lys Asp Gly Thr Gly Ser
65                  70                  75                  80

Asp Asp Lys Lys Ala Lys Gly Ala Asp Gly Lys Thr Lys Ile Ala Thr
                85                  90                  95

Pro Arg Gly Ala Ala Pro Pro Gly Gln Lys Gly Gln Ala Asn Ala Thr
            100                 105                 110

Arg Ile Pro Ala Lys Thr Pro Ala Pro Lys Thr Pro Pro Ser Ser
        115                 120                 125

Gly Glu Pro Pro Lys Ser Gly Asp Arg Ser Gly Tyr Ser Ser Pro Gly
    130                 135                 140

Ser Pro Gly Thr Pro Gly Ser Arg Ser Arg Thr Pro Ser Leu Pro Thr
145                 150                 155                 160

Pro Pro Thr Arg Glu Pro Lys Lys Val Ala Val Val Arg Thr Pro Pro
                165                 170                 175

Lys Ser Pro Ser Ser Ala Lys Ser Arg Leu Gln Thr Ala Pro Val Pro
            180                 185                 190

Met Pro Asp Leu Lys Asn Val Lys Ser Lys Ile Gly Ser Thr Glu Asn
        195                 200                 205

Leu Lys His Gln Pro Gly Gly Gly Lys Val Gln Ile Ile Asn Lys Lys
    210                 215                 220

Leu Asp Leu Ser Asn Val Gln Ser Lys Cys Gly Ser Lys Asp Asn Ile
225                 230                 235                 240

Lys His Val Pro Gly Gly Gly Ser Val Gln Ile Val Tyr Lys Pro Val
                245                 250                 255

Asp Leu Ser Lys Val Thr Ser Lys Cys Gly Ser Leu Gly Asn Ile His
            260                 265                 270

His Lys Pro Gly Gly Gly Gln Val Glu Val Lys Ser Glu Lys Leu Asp
        275                 280                 285

Phe Lys Asp Arg Val Gln Ser Lys Ile Gly Ser Leu Asp Asn Ile Thr
    290                 295                 300

His Val Pro Gly Gly Gly Asn Lys Lys Ile Glu Thr His Lys Leu Thr
305                 310                 315                 320

Phe Arg Glu Asn Ala Lys Ala Lys Thr Asp His Gly Ala Glu Ile Val
```

```
                 325                 330                 335
Tyr Lys Ser Pro Val Val Ser Gly Asp Thr Ser Pro Arg His Leu Ser
             340                 345                 350

Asn Val Ser Ser Thr Gly Ser Ile Asp Met Val Asp Ser Pro Gln Leu
             355                 360                 365

Ala Thr Leu Ala Asp Glu Val Ser Ala Ser Leu Ala Lys Gln Gly Leu
             370                 375                 380

<210> SEQ ID NO 45
<211> LENGTH: 6490
<212> TYPE: DNA
<213> ORGANISM: Artificial Sequence
<220> FEATURE:
<223> OTHER INFORMATION: synthetic

<400> SEQUENCE: 45
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt gccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt tcgccccga     780 agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct aacgtgagt tttcgttcca ctgagcgtca gaccccgtag aaaagatcaa    1620
aggatcttct tgagatcctt ttttctgcg cgtaatctgc tgcttgcaaa caaaaaaacc    1680
accgctacca gcggtggttt gtttgccgga tcaagagcta ccaactcttt ttccgaaggt    1740
```

```
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag cgcagcggt cgggctgaac gggggttcg tgcacacagc ccagcttgga      1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggccttttg ctcacatgtt    2280
ctttcctgcg ttatccctg attctgtgga taaccgtatt accgcctttg agtgagctga     2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacaccgcc aacacccgct gacgcgccct     2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggg atttctgttc atgggggtaa     2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg cgataatgg cctgcttctc gccgaaacgt tggtggcgg      3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg ttaacggga ggatataaca tgagctgtct     3900
tcggtatcgt cgtatcccac taccgagatg tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
```

```
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga acggtctga     4680
taagagacac cggcatactc tgcgacatcg tataacgtta ctggtttcac attcaccacc    4740
ctgaattgac tctcttccgg gcgctatcat gccataccgc gaaaggtttt cgccattcg     4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccatacce acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
cgatctcgat cccgcgaaat taatacgact cactataggg gaattgtgag cggataacaa    5160
ttcccctcta gaaataattt tgtttaactt taagaaggag atatacatat gggctcaagc    5220
caccaccacc accaccacag cagcggcgag aacttgtact ttcaaggatc cgcagaacca    5280
cgtcaagaat ttgaggttat ggaagatcac gcgggcactt acggtttggg tgatcgtaaa    5340
gaccagggcg gctataccat gcatcaagat caagagggcg acaccgatgc tggcttgaaa    5400
gcagaagagg cgggtatcgg cgacactccg tccctggaag atgaggcagc cggtcatgtc    5460
acgcaggcgc gtatggtgag caagagcaaa gatggtacgg gtagcgacga caagaaggcg    5520
aagggcgcag atggcaagac caaaattgcg acgccgcgtg gtgcggcacc gccaggccag    5580
aaaggtcagg cgaatgccac gcgcatcccg gcaaagacgc caccggctcc gaaaaccccg    5640
ccttccagcg gtgaaccgcc gaaatccggt gaccgcagcg ttatagctc tccgggtagc     5700
ccgggtaccc caggcagccg tagccgcacc ccgagcctgc cgaccccacc gacccgcgag    5760
ccgaagaaag tggcggtggt tcgtacgccg ccaaaaagcc cgagctctgc caagagccgt    5820
ctgcaaaccg ctcctgtgcc gatgccggac ctgaagaacg ttaagtctaa aatcggtagc    5880
accgaaaatc tgaagcacca acctggtggc ggtaaggtcc agattgtgta caaaccggtg    5940
gacctgagca aggttaccag caaatgcggt tccctgggta acatccatca taaaccgggt    6000
ggcggccaag ttgaggtcaa gagcgagaaa ctggacttca agaccgcgt tcagtccaaa     6060
atcggttctc tggacaacat tacgcacgtg cctggtggtg gcaacaagaa gattgaaacc    6120
cataaactga cgtttcgtga aaatgcgaag gcgaaaaccg accacggcgc agagattgtc    6180
tacaaaagcc cggtggtgag cggtgatacc agcccgcgtc acctgtccaa cgtcagcagc    6240
acgggcagca ttgatatggt ggatagcccg cagttggcta cgctggccga tgaggttagc    6300
gcgagcctgg cgaagcaggg tctgtgactc gagcaccacc accaccacca ctgagatccg    6360
gctgctaaca aagcccgaaa ggaagctgag ttggctgctg ccaccgctga gcaataacta    6420
gcataaccccc ttggggcctc taaacgggtc ttgaggggtt ttttgctgaa aggaggaact    6480
```

```
atatccggat                                                               6490
```

<210> SEQ ID NO 46
<211> LENGTH: 372
<212> TYPE: PRT
<213> ORGANISM: Artificial Sequence
<220> FEATURE:
<223> OTHER INFORMATION: synthetic

<400> SEQUENCE: 46

Met Gly Ser Ser His His His His His Ser Ser Gly Glu Asn Leu
1               5                   10                  15

Tyr Phe Gln Gly Ser Ala Glu Pro Arg Gln Glu Phe Glu Val Met Glu
            20                  25                  30

Asp His Ala Gly Thr Tyr Gly Leu Gly Asp Arg Lys Asp Gln Gly Gly
        35                  40                  45

Tyr Thr Met His Gln Asp Gln Glu Gly Asp Thr Asp Ala Gly Leu Lys
    50                  55                  60

Ala Glu Glu Ala Gly Ile Gly Asp Thr Pro Ser Leu Glu Asp Glu Ala
65                  70                  75                  80

Ala Gly His Val Thr Gln Ala Arg Met Val Ser Lys Ser Lys Asp Gly
                85                  90                  95

Thr Gly Ser Asp Asp Lys Lys Ala Lys Gly Ala Asp Gly Lys Thr Lys
            100                 105                 110

Ile Ala Thr Pro Arg Gly Ala Ala Pro Pro Gly Gln Lys Gly Gln Ala
        115                 120                 125

Asn Ala Thr Arg Ile Pro Ala Lys Thr Pro Pro Ala Pro Lys Thr Pro
    130                 135                 140

Pro Ser Ser Gly Glu Pro Pro Lys Ser Gly Asp Arg Ser Gly Tyr Ser
145                 150                 155                 160

Ser Pro Gly Ser Pro Gly Thr Pro Gly Ser Arg Ser Arg Thr Pro Ser
                165                 170                 175

Leu Pro Thr Pro Pro Thr Arg Glu Pro Lys Lys Val Ala Val Val Arg
            180                 185                 190

Thr Pro Pro Lys Ser Pro Ser Ser Ala Lys Ser Arg Leu Gln Thr Ala
        195                 200                 205

Pro Val Pro Met Pro Asp Leu Lys Asn Val Lys Ser Lys Ile Gly Ser
    210                 215                 220

Thr Glu Asn Leu Lys His Gln Pro Gly Gly Gly Lys Val Gln Ile Val
225                 230                 235                 240

Tyr Lys Pro Val Asp Leu Ser Lys Val Thr Ser Lys Cys Gly Ser Leu
                245                 250                 255

Gly Asn Ile His His Lys Pro Gly Gly Gly Gln Val Glu Val Lys Ser
            260                 265                 270

Glu Lys Leu Asp Phe Lys Asp Arg Val Gln Ser Lys Ile Gly Ser Leu
        275                 280                 285

Asp Asn Ile Thr His Val Pro Gly Gly Gly Asn Lys Lys Ile Glu Thr
    290                 295                 300

His Lys Leu Thr Phe Arg Glu Asn Ala Lys Ala Lys Thr Asp His Gly
305                 310                 315                 320

Ala Glu Ile Val Tyr Lys Ser Pro Val Val Ser Gly Asp Thr Ser Pro
                325                 330                 335

Arg His Leu Ser Asn Val Ser Ser Thr Gly Ser Ile Asp Met Val Asp
            340                 345                 350

Ser Pro Gln Leu Ala Thr Leu Ala Asp Glu Val Ser Ala Ser Leu Ala

```
                355                 360                 365

Lys Gln Gly Leu
    370

<210> SEQ ID NO 47
<211> LENGTH: 353
<212> TYPE: PRT
<213> ORGANISM: Artificial Sequence
<220> FEATURE:
<223> OTHER INFORMATION: synthetic

<400> SEQUENCE: 47

Gly Ser Ala Glu Pro Arg Gln Glu Phe Glu Val Met Glu Asp His Ala
1               5                   10                  15

Gly Thr Tyr Gly Leu Gly Asp Arg Lys Asp Gln Gly Gly Tyr Thr Met
            20                  25                  30

His Gln Asp Gln Glu Gly Asp Thr Asp Ala Gly Leu Lys Ala Glu Glu
        35                  40                  45

Ala Gly Ile Gly Asp Thr Pro Ser Leu Glu Asp Glu Ala Ala Gly His
    50                  55                  60

Val Thr Gln Ala Arg Met Val Ser Lys Ser Lys Asp Gly Thr Gly Ser
65                  70                  75                  80

Asp Asp Lys Lys Ala Lys Gly Ala Asp Gly Lys Thr Lys Ile Ala Thr
                85                  90                  95

Pro Arg Gly Ala Ala Pro Pro Gly Gln Lys Gly Gln Ala Asn Ala Thr
            100                 105                 110

Arg Ile Pro Ala Lys Thr Pro Pro Ala Pro Lys Thr Pro Pro Ser Ser
        115                 120                 125

Gly Glu Pro Pro Lys Ser Gly Asp Arg Ser Gly Tyr Ser Ser Pro Gly
    130                 135                 140

Ser Pro Gly Thr Pro Gly Ser Arg Ser Arg Thr Pro Ser Leu Pro Thr
145                 150                 155                 160

Pro Pro Thr Arg Glu Pro Lys Lys Val Ala Val Val Arg Thr Pro Pro
                165                 170                 175

Lys Ser Pro Ser Ser Ala Lys Ser Arg Leu Gln Thr Ala Pro Val Pro
            180                 185                 190

Met Pro Asp Leu Lys Asn Val Lys Ser Lys Ile Gly Ser Thr Glu Asn
        195                 200                 205

Leu Lys His Gln Pro Gly Gly Gly Lys Val Gln Ile Val Tyr Lys Pro
    210                 215                 220

Val Asp Leu Ser Lys Val Thr Ser Lys Cys Gly Ser Leu Gly Asn Ile
225                 230                 235                 240

His His Lys Pro Gly Gly Gly Gln Val Glu Val Lys Ser Glu Lys Leu
                245                 250                 255

Asp Phe Lys Asp Arg Val Gln Ser Lys Ile Gly Ser Leu Asp Asn Ile
            260                 265                 270

Thr His Val Pro Gly Gly Gly Asn Lys Lys Ile Glu Thr His Lys Leu
        275                 280                 285

Thr Phe Arg Glu Asn Ala Lys Ala Lys Thr Asp His Gly Ala Glu Ile
    290                 295                 300

Val Tyr Lys Ser Pro Val Val Ser Gly Asp Thr Ser Pro Arg His Leu
305                 310                 315                 320

Ser Asn Val Ser Ser Thr Gly Ser Ile Asp Met Val Asp Ser Pro Gln
                325                 330                 335

Leu Ala Thr Leu Ala Asp Glu Val Ser Ala Ser Leu Ala Lys Gln Gly
```

Leu

<210> SEQ ID NO 48
<211> LENGTH: 6670
<212> TYPE: DNA
<213> ORGANISM: Artificial Sequence
<220> FEATURE:
<223> OTHER INFORMATION: synthetic

<400> SEQUENCE: 48

| | | | | | | |
|---|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tcccttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | tgacgttgg | agtccacgtt | 300 |
| ctttaatagt | ggactcttgt | tccaaactgg | aacaacactc | aaccctatct | cggtctattc | 360 |
| ttttgattta | aagggatttt | gccgatttc | ggctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttattttc | taaatacatt | caaatatgta | 540 |
| tccgctcatg | agacaataac | cctgataaat | gcttcaataa | tattgaaaaa | ggaagagtat | 600 |
| gagtattcaa | catttccgtg | tcgcccttat | tcccttttt | gcggcatttt | gccttcctgt | 660 |
| ttttgctcac | ccagaaacgc | tggtgaaagt | aaaagatgct | gaagatcagt | tgggtgcacg | 720 |
| agtgggttac | atcgaactgg | atctcaacag | cggtaagatc | cttgagagtt | ttcgccccga | 780 |
| agaacgtttt | ccaatgatga | gcacttttaa | agttctgcta | tgtggcgcgg | tattatcccg | 840 |
| tattgacgcc | gggcaagagc | aactcggtcg | ccgcatacac | tattctcaga | atgacttggt | 900 |
| tgagtactca | ccagtcacag | aaaagcatct | tacggatggc | atgacagtaa | gagaattatg | 960 |
| cagtgctgcc | ataaccatga | gtgataacac | tgcggccaac | ttacttctga | caacgatcgg | 1020 |
| aggaccgaag | gagctaaccg | cttttttgca | caacatgggg | gatcatgtaa | ctcgccttga | 1080 |
| tcgttgggaa | ccggagctga | atgaagccat | accaaacgac | gagcgtgaca | ccacgatgcc | 1140 |
| tgcagcaatg | gcaacaacgt | tgcgcaaact | attaactggc | gaactactta | ctctagcttc | 1200 |
| ccggcaacaa | ttaatagact | ggatggaggc | ggataaagtt | gcaggaccac | ttctgcgctc | 1260 |
| ggcccttccg | gctggctggt | ttattgctga | taaatctgga | gccggtgagc | gtgggtctcg | 1320 |
| cggtatcatt | gcagcactgg | ggccagatgg | taagccctcc | cgtatcgtag | ttatctacac | 1380 |
| gacggggagt | caggcaacta | tggatgaacg | aaatagacag | atcgctgaga | taggtgcctc | 1440 |
| actgattaag | cattggtaac | tgtcagacca | agtttactca | tatatacttt | agattgattt | 1500 |
| aaaacttcat | ttttaattta | aaaggatcta | ggtgaagatc | cttttgata | atctcatgac | 1560 |
| caaaatccct | taacgtgagt | tttcgttcca | ctgagcgtca | gaccccgtag | aaaagatcaa | 1620 |
| aggatcttct | tgagatcctt | tttttctgcg | cgtaatctgc | tgcttgcaaa | caaaaaaacc | 1680 |
| accgctacca | gcggtggttt | gtttgccgga | tcaagagcta | ccaactcttt | ttccgaaggt | 1740 |
| aactggcttc | agcagagcgc | agataccaaa | tactgtcctt | ctagtgtagc | cgtagttagg | 1800 |
| ccaccacttc | aagaactctg | tagcaccgcc | tacatacctc | gctctgctaa | tcctgttacc | 1860 |
| agtggctgct | gccagtggcg | ataagtcgtg | tcttaccggg | ttggactcaa | gacgatagtt | 1920 |
| accggataag | gcgcagcggt | cgggctgaac | ggggggttcg | tgcacacagc | ccagcttgga | 1980 |

```
gcgaacgacc tacaccgaac tgagatacct acagcgtgag ctatgagaaa gcgccacgct      2040
tcccgaaggg agaaaggcgg acaggtatcc ggtaagcggc agggtcggaa caggagagcg      2100
cacgagggag cttccagggg gaaacgcctg gtatctttat agtcctgtcg ggtttcgcca      2160
cctctgactt gagcgtcgat ttttgtgatg ctcgtcaggg gggcggagcc tatggaaaaa      2220
cgccagcaac gcggcctttt tacggttcct ggccttttgc tggccttttg ctcacatgtt      2280
ctttcctgcg ttatccsctg attctgtgga taaccgtatt accgcctttg agtgagctga      2340
taccgctcgc cgcagccgaa cgaccgagcg cagcgagtca gtgagcgagg aagcggaaga      2400
gcgcctgatg cggtattttc tccttacgca tctgtgcggt atttcacacc gcatatatgg      2460
tgcactctca gtacaatctg ctctgatgcc gcatagttaa gccagtatac actccgctat      2520
cgctacgtga ctgggtcatg gctgcgcccc gacacccgcc aacacccgct gacgcgccct      2580
gacgggcttg tctgctcccg gcatccgctt acagacaagc tgtgaccgtc tccgggagct      2640
gcatgtgtca gaggttttca ccgtcatcac cgaaacgcgc gaggcagctg cggtaaagct      2700
catcagcgtg gtcgtgaagc gattcacaga tgtctgcctg ttcatccgcg tccagctcgt      2760
tgagtttctc cagaagcgtt aatgtctggc ttctgataaa gcgggccatg ttaagggcgg      2820
ttttttcctg tttggtcact gatgcctccg tgtaaggggg atttctgttc atgggggtaa      2880
tgataccgat gaaacgagag aggatgctca cgatacgggt tactgatgat gaacatgccc      2940
ggttactgga acgttgtgag ggtaaacaac tggcggtatg gatgcggcgg gaccagagaa      3000
aaatcactca gggtcaatgc cagcgcttcg ttaatacaga tgtaggtgtt ccacagggta      3060
gccagcagca tcctgcgatg cagatccgga acataatggt gcagggcgct gacttccgcg      3120
tttccagact ttacgaaaca cggaaaccga agaccattca tgttgttgct caggtcgcag      3180
acgttttgca gcagcagtcg cttcacgttc gctcgcgtat cggtgattca ttctgctaac      3240
cagtaaggca accccgccag cctagccggg tcctcaacga caggagcacg atcatgcgca      3300
cccgtggggc cgccatgccg cgataatggc ctgcttctc gccgaaacgt tggtggcgg       3360 gaccagtgac gaaggcttga gcgagggcgt gcaagattcc gaataccgca agcgacaggc      3420
cgatcatcgt cgcgctccag cgaaagcggt cctcgccgaa aatgacccag agcgctgccg      3480
gcacctgtcc tacgagttgc atgataaaga agacagtcat aagtgcggcg acgatagtca      3540
tgccccgcgc ccaccggaag gagctgactg ggttgaaggc tctcaagggc atcggtcgag      3600
atcccggtgc ctaatgagtg agctaactta cattaattgc gttgcgctca ctgcccgctt      3660
tccagtcggg aaacctgtcg tgccagctgc attaatgaat cggccaacgc gcggggagag      3720
gcggtttgcg tattgggcgc cagggtggtt tttcttttca ccagtgagac gggcaacagc      3780
tgattgccct tcaccgcctg gccctgagag agttgcagca agcggtccac gctggtttgc      3840
cccagcaggc gaaaatcctg tttgatggtg gttaacggcg ggatataaca tgagctgtct      3900
tcggtatcgt cgtatcccac taccgagatg tccgcaccaa cgcgcagccc ggactcggta      3960
atggcgcgca ttgcgcccag cgccatctga tcgttggcaa ccagcatcgc agtgggaacg      4020
atgccctcat tcagcatttg catggtttgt tgaaaaccgg acatggcact ccagtcgcct      4080
tcccgttccg ctatcggctg aatttgattg cgagtgagat atttatgcca gccagccaga      4140
cgcagacgcg ccgagacaga acttaatggg cccgctaaca gcgcgatttg ctggtgaccc      4200
aatgcgacca gatgctccac gcccagtcgc gtaccgtctt catgggagaa ataatactg       4260 ttgatgggtg tctggtcaga gacatcaaga aataacgccg gaacattagt gcaggcagct      4320
```

```
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcaggggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
cgatctcgat cccgcgaaat taatacgact cactataggg gaattgtgag cggataacaa    5160
ttcccctcta gaaataattt tgtttaactt taagaaggag atatacatat gggctcaagc    5220
caccaccacc accaccacag cagcggcgag aacttgtact ttcaaggatc cgcagaacca    5280
cgtcaagaat ttgaggttat ggaagatcac gcgggcactt acgtttggg tgatcgtaaa    5340
gaccagggcg gctataccat gcatcaagat caagagggcg acaccgatgc tggcttgaaa    5400
gagtcgccgc tgcagactcc gaccgaggat ggcagcgaag agccgggcag cgagactagc    5460
gatgcgaagt cgaccccgac cgccgaggca gaagaggcgg gtatcggcga cactccgtcc    5520
ctggaagatg aggcagccgg tcatgtcacg caggcgcgta tggtgagcaa gagcaaagat    5580
ggtacgggta gcgacgacaa gaaggcgaag ggcgcagatg gcaagaccaa aattgcgacg    5640
ccgcgtggtg cggcaccgcc aggccagaaa ggtcaggcga atgccacgcg catcccggca    5700
aagacgccac cggctccgaa aaccccgcct tccagcggtg aaccgccgaa atccggtgac    5760
cgcagcggtt atagctctcc gggtagcccg ggtaccccag gcagccgtag ccgcaccccg    5820
agcctgccga ccccaccgac ccgcgagccg aagaaagtgg cggtggttcg tacgccgcca    5880
aaaagcccga gctctgccaa gagccgtctg caaaccgctc ctgtgccgat gccggaccgt    5940
aagaacgtta agtctaaaat cggtagcacc gaaaatctga agcaccaacc tggtggcggt    6000
aaggttcaaa tcatcaacaa aaagctggac ttgagcaatg tacaaagcaa gtgtggtagc    6060
aaggacaata tcaaacacgt cccgggtggt ggttccgtcc agattgtgta caaaccggtg    6120
gacctgagca aggttaccag caaatgcggt tccctgggta acatccatca taaaccgggt    6180
ggcggccaag ttgaggtcaa gagcgagaaa ctggacttca aagaccgcgt tcagtccaaa    6240
atcggttctc tggacaacat tacgcacgtg cctggtggtg gcaacaagaa gattgaaacc    6300
cataaactga cgtttcgtga aaatgcgaag gcgaaaaccg accacggcgc agagattgtc    6360
tacaaaagcc cggtggtgag cggtgatacc agcccgcgtc acctgtccaa cgtcagcagc    6420
acgggcagca ttgatatggt ggatagcccg cagttggcta cgctggccga tgaggttagc    6480
gcgagcctgg cgaagcaggg tctgtgactc gagcaccacc accaccacca ctgagatccg    6540
gctgctaaca aagcccgaaa ggaagctgag ttggctgctg ccaccgctga gcaataacta    6600
gcataacccc ttggggcctc taaacgggtc ttgaggggtt ttttgctgaa aggaggaact    6660
atatccggat                                                           6670
```

<210> SEQ ID NO 49
<211> LENGTH: 432
<212> TYPE: PRT
<213> ORGANISM: Artificial Sequence
<220> FEATURE:
<223> OTHER INFORMATION: synthetic

<400> SEQUENCE: 49

```
Met Gly Ser Ser His His His His His His Ser Ser Gly Glu Asn Leu
1               5                   10                  15

Tyr Phe Gln Gly Ser Ala Glu Pro Arg Gln Glu Phe Glu Val Met Glu
            20                  25                  30

Asp His Ala Gly Thr Tyr Gly Leu Gly Asp Arg Lys Asp Gln Gly Gly
        35                  40                  45

Tyr Thr Met His Gln Asp Gln Glu Gly Asp Thr Asp Ala Gly Leu Lys
    50                  55                  60

Glu Ser Pro Leu Gln Thr Pro Thr Glu Asp Gly Ser Glu Glu Pro Gly
65                  70                  75                  80

Ser Glu Thr Ser Asp Ala Lys Ser Thr Pro Thr Ala Glu Ala Glu Glu
                85                  90                  95

Ala Gly Ile Gly Asp Thr Pro Ser Leu Glu Asp Glu Ala Ala Gly His
            100                 105                 110

Val Thr Gln Ala Arg Met Val Ser Lys Ser Lys Asp Gly Thr Gly Ser
        115                 120                 125

Asp Asp Lys Lys Ala Lys Gly Ala Asp Gly Lys Thr Lys Ile Ala Thr
    130                 135                 140

Pro Arg Gly Ala Ala Pro Pro Gly Gln Lys Gly Gln Ala Asn Ala Thr
145                 150                 155                 160

Arg Ile Pro Ala Lys Thr Pro Pro Ala Pro Lys Thr Pro Pro Ser Ser
                165                 170                 175

Gly Glu Pro Pro Lys Ser Gly Asp Arg Ser Gly Tyr Ser Ser Pro Gly
            180                 185                 190

Ser Pro Gly Thr Pro Gly Ser Arg Ser Arg Thr Pro Ser Leu Pro Thr
        195                 200                 205

Pro Pro Thr Arg Glu Pro Lys Lys Val Ala Val Val Arg Thr Pro Pro
    210                 215                 220

Lys Ser Pro Ser Ser Ala Lys Ser Arg Leu Gln Thr Ala Pro Val Pro
225                 230                 235                 240

Met Pro Asp Leu Lys Asn Val Lys Ser Lys Ile Gly Ser Thr Glu Asn
                245                 250                 255

Leu Lys His Gln Pro Gly Gly Gly Lys Val Gln Ile Ile Asn Lys Lys
            260                 265                 270

Leu Asp Leu Ser Asn Val Gln Ser Lys Cys Gly Ser Lys Asp Asn Ile
        275                 280                 285

Lys His Val Pro Gly Gly Gly Ser Val Gln Ile Val Tyr Lys Pro Val
    290                 295                 300

Asp Leu Ser Lys Val Thr Ser Lys Cys Gly Ser Leu Gly Asn Ile His
305                 310                 315                 320

His Lys Pro Gly Gly Gly Gln Val Glu Val Lys Ser Glu Lys Leu Asp
                325                 330                 335

Phe Lys Asp Arg Val Gln Ser Lys Ile Gly Ser Leu Asp Asn Ile Thr
            340                 345                 350

His Val Pro Gly Gly Gly Asn Lys Lys Ile Glu Thr His Lys Leu Thr
        355                 360                 365
```

```
Phe Arg Glu Asn Ala Lys Ala Lys Thr Asp His Gly Ala Glu Ile Val
    370                 375                 380

Tyr Lys Ser Pro Val Val Ser Gly Asp Thr Ser Pro Arg His Leu Ser
385                 390                 395                 400

Asn Val Ser Ser Thr Gly Ser Ile Asp Met Val Asp Ser Pro Gln Leu
                405                 410                 415

Ala Thr Leu Ala Asp Glu Val Ser Ala Ser Leu Ala Lys Gln Gly Leu
            420                 425                 430
```

<210> SEQ ID NO 50
<211> LENGTH: 413
<212> TYPE: PRT
<213> ORGANISM: Artificial Sequence
<220> FEATURE:
<223> OTHER INFORMATION: synthetic

<400> SEQUENCE: 50

```
Gly Ser Ala Glu Pro Arg Gln Glu Phe Glu Val Met Glu Asp His Ala
1               5                   10                  15

Gly Thr Tyr Gly Leu Gly Asp Arg Lys Asp Gln Gly Gly Tyr Thr Met
            20                  25                  30

His Gln Asp Gln Glu Gly Asp Thr Asp Ala Gly Leu Lys Glu Ser Pro
        35                  40                  45

Leu Gln Thr Pro Thr Glu Asp Gly Ser Glu Glu Pro Gly Ser Glu Thr
    50                  55                  60

Ser Asp Ala Lys Ser Thr Pro Thr Ala Glu Ala Glu Ala Gly Ile
65                  70                  75                  80

Gly Asp Thr Pro Ser Leu Glu Asp Glu Ala Ala Gly His Val Thr Gln
                85                  90                  95

Ala Arg Met Val Ser Lys Ser Lys Asp Gly Thr Gly Ser Asp Asp Lys
            100                 105                 110

Lys Ala Lys Gly Ala Asp Gly Lys Thr Lys Ile Ala Thr Pro Arg Gly
        115                 120                 125

Ala Ala Pro Pro Gly Gln Lys Gly Gln Ala Asn Ala Thr Arg Ile Pro
    130                 135                 140

Ala Lys Thr Pro Pro Ala Pro Lys Thr Pro Pro Ser Ser Gly Glu Pro
145                 150                 155                 160

Pro Lys Ser Gly Asp Arg Ser Gly Tyr Ser Ser Pro Gly Ser Pro Gly
                165                 170                 175

Thr Pro Gly Ser Arg Ser Arg Thr Pro Ser Leu Pro Thr Pro Pro Thr
            180                 185                 190

Arg Glu Pro Lys Lys Val Ala Val Val Arg Thr Pro Pro Lys Ser Pro
        195                 200                 205

Ser Ser Ala Lys Ser Arg Leu Gln Thr Ala Pro Val Pro Met Pro Asp
    210                 215                 220

Leu Lys Asn Val Lys Ser Lys Ile Gly Ser Thr Glu Asn Leu Lys His
225                 230                 235                 240

Gln Pro Gly Gly Gly Lys Val Gln Ile Ile Asn Lys Lys Leu Asp Leu
                245                 250                 255

Ser Asn Val Gln Ser Lys Cys Gly Ser Lys Asp Asn Ile Lys His Val
            260                 265                 270

Pro Gly Gly Gly Ser Val Gln Ile Val Tyr Lys Pro Val Asp Leu Ser
        275                 280                 285

Lys Val Thr Ser Lys Cys Gly Ser Leu Gly Asn Ile His His Lys Pro
    290                 295                 300
```

Gly Gly Gly Gln Val Glu Val Lys Ser Glu Lys Leu Asp Phe Lys Asp
305                 310                 315                 320

Arg Val Gln Ser Lys Ile Gly Ser Leu Asp Asn Ile Thr His Val Pro
            325                 330                 335

Gly Gly Gly Asn Lys Lys Ile Glu Thr His Lys Leu Thr Phe Arg Glu
        340                 345                 350

Asn Ala Lys Ala Lys Thr Asp His Gly Ala Glu Ile Val Tyr Lys Ser
    355                 360                 365

Pro Val Val Ser Gly Asp Thr Ser Pro Arg His Leu Ser Asn Val Ser
370                 375                 380

Ser Thr Gly Ser Ile Asp Met Val Asp Ser Pro Gln Leu Ala Thr Leu
385                 390                 395                 400

Ala Asp Glu Val Ser Ala Ser Leu Ala Lys Gln Gly Leu
                405                 410

<210> SEQ ID NO 51
<211> LENGTH: 6016
<212> TYPE: DNA
<213> ORGANISM: Artificial Sequence
<220> FEATURE:
<223> OTHER INFORMATION: synthetic

<400> SEQUENCE: 51

```
gctgcttcgc gatgtacggg ccagatatac gcgttttgag atttctgtcg ccgactaaat      60
tcatgtcgcg cgatagtggt gtttatcgcc gatagagatg gcgatattgg aaaaatcggc     120
ggccgccgat atttgaaaat atggcatatt gaaaatgtcg ccgatgtgag tttctgtgta     180
actgacatcg ccatttttcc aaaagtgatt tttgggcata cgcggtatct ggcgatagcg     240
cttatatcgt ttacggggga tggcgataga cgactttggt gacttgggcg attctgtgtg     300
tcgcaaatat cgcagtttcg ataggtgaca cagacgatat gaggctatat cgccgataga     360
ggcgacatca agctggcaca tggccaatgc atatcgatct atacattgaa tcaatattgg     420
ccattagcca tattattcat tggttatata gcataaatca atattggcta ttggccattg     480
catacgttgt atccatatca taatatgtac atttatattg gctcatgtcc aacattaccg     540
ccatgttgac attgattatt gactagttat taatagtaat caattacggg gtcattagtt     600
catagcccat atatggagtt ccgcgttaca taacttacgg taaatggccc gcctggctga     660
ccgcccaacg accccgcccc attgacgtca ataatgacgt atgttcccat agtaacgcca     720
atagggactt tccattgacg tcaatgggtg gagtatttac ggtaaactgc ccacttggca     780
gtacatcaag tgtatcatat gccaagtacg ccccctattg acgtcaatga cggtaaatgg     840
cccgcctggc attatgccca gtacatgacc ttatgggact ttcctacttg gcagtacatc     900
tacgtattag tcatcgctat tacaatggtg atgcggtttt ggcagtacat caatgggcgt     960
ggatagcggt ttgactcacg gggatttcca agtctccacc ccattgacgt caatgggagt    1020
ttgttttggc accaaaatca acgggacttt ccaaaatgtc gtaacaactc cgccccattg    1080
acgcaaatgg gcggtaggcg tgtacggtgg gaggtctata taagcagaac tcgtttagtg    1140
aaccgtcaga tcgcctggag acgccatcca cgctgttttg acctccatag aagacaccgg    1200
gaccgatcca gcctccgcgg ccgggaacgg tgcattggaa cgcggattcc ccgtgccaag    1260
agtgacgtaa gtaccgccta gagtctatag gcccaccc cattggcttc ttatgcatgc    1320
tatactgttt ttggcttggg gtctatacac cccgcttcc tcatgttata ggtgatggta    1380
tagcttagcc tataggtgtg ggttattgac cattattgac cactccccta ttggtgacga    1440
```

```
tactttccat tactaatcca taacatggct ctttgccaca actctcttta ttggctatat    1500
gccaatacac tgtccttcag agactgacac ggactctgta tttttacagg atggggtctc    1560
atttattatt tacaaattca catatacaac accaccgtcc ccagtgcccg cagtttttat    1620
taaacataac gtgggatctc cacgcgaatc tagggtacgt gttacggaca tgggctattc    1680
tcaggtagcg gcggagcttc tacatccgag ccctgctccc atgcctccag cgaatcatgg    1740
tcgctcggca gctccttgct cctaacagtg gaggccagac ttaggcacag cacgatgccc    1800
accaccacca gtgtgccgca caaggccgtg gcggtagggt atgtgtctga aaatgaacta    1860
ggggagcggg cttgcaccgc tgacgcattt ggaagactta aggcagcggc agaagaagat    1920
gcaggcaact gagttgttgt gttctgataa gagtcagagg taactcccgt tgcggtgctg    1980
ttaacggtgg agggcagtgt agtctgagca gtactcgttg ctgccgcacg cgccaccaga    2040
cataatagct gacagactaa cagactgttc ctttcaatgg gtctttatg cagtcaccgt      2100
ccttgacacg aagcttgcca ccatgggctc aagccaccat caccaccacc atcatcacca    2160
ccacagcagc ggcgagaact tgtactttca aggatccgct gagccccgcc aggagttcga    2220
agtgatggaa gatcacgctg ggacgtacgg gttgggggac aggaaagatc aggggggcta    2280
caccatgcac caagaccaag agggtgacac ggacgctggc ctgaaagaat ctcccctgca    2340
gacccccact gaggacggat ctgaggaacc gggctctgaa acctctgatg ctaagagcac    2400
tccaacagcg gaagatgtga cagcacccct tagtggatgag ggagctcccg gcaagcaggc    2460
tgccgcgcag ccccacacgg agatcccaga aggaaccaca gctgaagaag caggcattgg    2520
agacaccccc agcctggaag acgaagctgc tggtcacgtg acccaagctc gcatggtcag    2580
taaaagcaaa gacgggactg gaagcgatga caaaaaagcc aagggggctg atggtaaaac    2640
gaagatcgcc acaccgcggg gagcagcccc tccaggccag aagggccagg ccaacgccac    2700
caggattcca gcaaaaaccc cgcccgctcc aaagacacca cccagctctg gtgaacctcc    2760
aaaatcaggg gatcgcagcg gctacagcag cccccggctcc ccaggcactc ccggcagccg    2820
ctcccgcacc ccgtcccttc aaccccacc caccgggag cccaagaagg tggcagtggt      2880
ccgtactcca cccaagtcgc cgtcttccgc caagagccgc ctgcagacag ccccgtgcc      2940
catgccagac ctgaagaatg tcaagtccaa gatcggctcc actgagaacc tgaagcacca    3000
gccgggaggc gggaaggtgc agataattaa taagaagctg gatcttagca acgtccagtc    3060
caagtgtggc tcaaaggata atatcaaaca cgtcccggga ggcggcagtg tgcaaatagt    3120
ctacaaacca gttgacctga gcaaggtgac ctccaagtgt ggctcattag caacatcca    3180
tcataaacca ggaggtggcc aggtggaagt aaaatctgag aagctagact caaggacag    3240
agtccagtcg aagattgggt ccctggacaa tatcacccac gtccctggcg gagaaataa    3300
aaagattgaa acccacaagc tgaccttccg cgagaacgcc aaagccaaga cagaccacgg    3360
ggcggagatc gtgtacaagt cgccagtggt gtctggggac acgtctccac ggcatctcag    3420
caatgtctcc tccaccggca gcatcgacat ggtagactcg ccccagctcg ccacgctagc    3480
tgacgaggtg tctgcctccc tggccaagca gggtttgtga ctcgaggaga acttgtactt    3540
ccagggaagt ggtggcagtc atcaccatca ccatcaccat caccatcact gagaattcat    3600
tgatcataat cagccatacc acatttgtag aggttttact tgctttaaaa aacctcccac    3660
acctcccct gaacctgaaa cataaaatga atgcaattgt tgttgttaac ttgtttattg    3720
cagcttataa tggttacaaa taaagcaata gcatcacaaa tttcacaaat aaagcatttt    3780
```

```
tttcactgca ttctagttgt ggtttgtcca aactcatcaa tgtatcttat catgtctgaa   3840
tcctctacgc cggacgcatc gtggccggca tcaccggcgc cacaggtgcg gttgctggcg   3900
cctatatcgc cgacatcacc gatggggaag atcgggctcg ccacttcggg ctcatgagcg   3960
cttgtttcgg cgtgggtatg gtggcaggcc ccgtggccgg gggactgttg ggcgccatct   4020
ccttgcatgc accattcctt gcggcggcgg tgctcaacgg cctcaaccta ctactgggct   4080
gcttcctaat gcaggagtcg cataaggag agcgtcgact ggggcgccct ctggtaaggt   4140
tgggaagccc tgcaaagtaa actggatggc tttctcgccg ccaagcatct gatggcgcag   4200
gggatcaagc tctgatcaag agacaggatg aggatcgttt cgcatgattg aacaagatgg   4260
attgcacgca ggttctccgg ccgcttgggt ggagaggcta ttcggctatg actgggcaca   4320
acagacaatc ggctgctctg atgccgccgt gttccggctg tcagcgcagg ggcgcccggt   4380 tcttttttgtc aagaccgacc tgtccggtgc cctgaatgaa ctgcaagacg aggcagcgcg   4440
gctatcgtgg ctggccacga cgggcgttcc ttgcgcagca gtgctcgacg ttgtcactga   4500
agcgggaagg gactggctgc tattgggcga agtgccgggg caggatctcc tgtcatctca   4560
ccttgctcct gccgagaaag tatccatcat ggctgatgca atgcggcggc tgcatacgct   4620
tgatccggct acctgcccat tcgaccacca agcgaaacat cgcatcgagc gagcacgtac   4680
tcggatggaa gccggtcttg tcgatcagga tgatctggac gaagagcatc aggggctcgc   4740
gccagccgaa ctgttcgcca ggctcaaggc gagcatgccc gacggcgagg atctcgtcgt   4800
gacccacggc gatgcctgct tgccgaatat catggtggaa aatggccgct tttctggatt   4860
catcgactgt ggccggctgg gtgtggcgga ccgctatcag gacatagcgt tggctacccg   4920
tgatattgct gaagagcttg gcggcgaatg ggctgaccgc ttcctcgtgc tttacggtat   4980
cgccgctccc gattcgcagc gcatcgcctt ctatcgcctt cttgacgagt tcttctgaat   5040
tattaacgct tacaatttcc tgatgcggta ttttctcctt acgcatctgt gcggtatttc   5100
acaccgcatc aggtggcact tttcggggaa atgtgcgcgg aaccCCtatt tgtttatttt   5160
tctaaataca ttcaaatatg tatccgctca tgagacaata accctgataa atgcttcaat   5220
aatagcacgt gctaaaactt catttttaat ttaaaaggat ctaggtgaag atccttttg   5280 ataatctcat gaccaaaatc ccttaacgtg agttttcgtt ccactgagcg tcagacccccg   5340 tagaaaagat caaaggatct tcttgagatc ctttttttct gcgcgtaatc tgctgcttgc   5400
aaacaaaaaa accaccgcta ccagcggtgg tttgtttgcc ggatcaagag ctaccaactc   5460
tttttccgaa ggtaactggc ttcagcagag cgcagatacc aaatactgtt cttctagtgt   5520
agccgtagtt aggccaccac ttcaagaact ctgtagcacc gcctacatac ctcgctctgc   5580
taatcctgtt accagtggct gctgccagtg gcgataagtc gtgtcttacc gggttggact   5640
caagacgata gttaccggat aaggcgcagc ggtcgggctg aacggggggt tcgtgcacac   5700
agcccagctt ggagcgaacg acctacaccg aactgagata cctacagcgt gagctatgag   5760
aaagcgccac gcttcccgaa gggagaaagg cggacaggta tccggtaagc ggcagggtcg   5820
gaacaggaga gcgcacgagg gagcttccag ggggaaacgc ctggtatctt tatagtcctg   5880
tcgggtttcg ccacctctga cttgagcgtc gatttttgtg atgctcgtca gggggggcgga   5940 gcctatggaa aaacgccagc aacgcggcct ttttacggtt cctggccttt tgctggcctt   6000
ttgctcacat gttctt                                                  6016
```

<210> SEQ ID NO 52
<211> LENGTH: 465

```
<212> TYPE: PRT
<213> ORGANISM: Artificial Sequence
<220> FEATURE:
<223> OTHER INFORMATION: synthetic

<400> SEQUENCE: 52

Met Gly Ser Ser His His His His His His His His Ser Ser
1               5                   10                  15

Gly Glu Asn Leu Tyr Phe Gln Gly Ser Ala Glu Pro Arg Gln Glu Phe
            20                  25                  30

Glu Val Met Glu Asp His Ala Gly Thr Tyr Gly Leu Gly Asp Arg Lys
        35                  40                  45

Asp Gln Gly Gly Tyr Thr Met His Gln Asp Gln Glu Gly Asp Thr Asp
    50                  55                  60

Ala Gly Leu Lys Glu Ser Pro Leu Gln Thr Pro Thr Glu Asp Gly Ser
65                  70                  75                  80

Glu Glu Pro Gly Ser Glu Thr Ser Asp Ala Lys Ser Thr Pro Thr Ala
                85                  90                  95

Glu Asp Val Thr Ala Pro Leu Val Asp Glu Gly Ala Pro Gly Lys Gln
            100                 105                 110

Ala Ala Ala Gln Pro His Thr Glu Ile Pro Glu Gly Thr Thr Ala Glu
        115                 120                 125

Glu Ala Gly Ile Gly Asp Thr Pro Ser Leu Glu Asp Glu Ala Ala Gly
    130                 135                 140

His Val Thr Gln Ala Arg Met Val Ser Lys Ser Lys Asp Gly Thr Gly
145                 150                 155                 160

Ser Asp Asp Lys Lys Ala Lys Gly Ala Asp Gly Lys Thr Lys Ile Ala
                165                 170                 175

Thr Pro Arg Gly Ala Ala Pro Pro Gly Gln Lys Gly Gln Ala Asn Ala
            180                 185                 190

Thr Arg Ile Pro Ala Lys Thr Pro Pro Ala Pro Lys Thr Pro Pro Ser
        195                 200                 205

Ser Gly Glu Pro Pro Lys Ser Gly Asp Arg Ser Gly Tyr Ser Ser Pro
    210                 215                 220

Gly Ser Pro Gly Thr Pro Gly Ser Arg Ser Arg Thr Pro Ser Leu Pro
225                 230                 235                 240

Thr Pro Pro Thr Arg Glu Pro Lys Lys Val Ala Val Val Arg Thr Pro
                245                 250                 255

Pro Lys Ser Pro Ser Ser Ala Lys Ser Arg Leu Gln Thr Ala Pro Val
            260                 265                 270

Pro Met Pro Asp Leu Lys Asn Val Lys Ser Lys Ile Gly Ser Thr Glu
        275                 280                 285

Asn Leu Lys His Gln Pro Gly Gly Gly Lys Val Gln Ile Ile Asn Lys
    290                 295                 300

Lys Leu Asp Leu Ser Asn Val Gln Ser Lys Cys Gly Ser Lys Asp Asn
305                 310                 315                 320

Ile Lys His Val Pro Gly Gly Gly Ser Val Gln Ile Val Tyr Lys Pro
                325                 330                 335

Val Asp Leu Ser Lys Val Thr Ser Lys Cys Gly Ser Leu Gly Asn Ile
            340                 345                 350

His His Lys Pro Gly Gly Gly Gln Val Glu Val Lys Ser Glu Lys Leu
        355                 360                 365

Asp Phe Lys Asp Arg Val Gln Ser Lys Ile Gly Ser Leu Asp Asn Ile
    370                 375                 380
```

```
Thr His Val Pro Gly Gly Asn Lys Lys Ile Glu Thr His Lys Leu
385                 390                 395                 400

Thr Phe Arg Glu Asn Ala Lys Ala Lys Thr Asp His Gly Ala Glu Ile
                405                 410                 415

Val Tyr Lys Ser Pro Val Val Ser Gly Asp Thr Ser Pro Arg His Leu
                420                 425                 430

Ser Asn Val Ser Thr Gly Ser Ile Asp Met Val Asp Ser Pro Gln
                435                 440                 445

Leu Ala Thr Leu Ala Asp Glu Val Ser Ala Ser Leu Ala Lys Gln Gly
450                 455                 460

Leu
465

<210> SEQ ID NO 53
<211> LENGTH: 442
<212> TYPE: PRT
<213> ORGANISM: Artificial Sequence
<220> FEATURE:
<223> OTHER INFORMATION: synthetic

<400> SEQUENCE: 53

Gly Ser Ala Glu Pro Arg Gln Glu Phe Glu Val Met Glu Asp His Ala
1               5                   10                  15

Gly Thr Tyr Gly Leu Gly Asp Arg Lys Asp Gln Gly Gly Tyr Thr Met
                20                  25                  30

His Gln Asp Gln Glu Gly Asp Thr Asp Ala Gly Leu Lys Glu Ser Pro
            35                  40                  45

Leu Gln Thr Pro Thr Glu Asp Gly Ser Glu Pro Gly Ser Glu Thr
50                  55                  60

Ser Asp Ala Lys Ser Thr Pro Thr Ala Glu Asp Val Thr Ala Pro Leu
65                  70                  75                  80

Val Asp Glu Gly Ala Pro Gly Lys Gln Ala Ala Ala Gln Pro His Thr
                85                  90                  95

Glu Ile Pro Glu Gly Thr Thr Ala Glu Glu Ala Gly Ile Gly Asp Thr
            100                 105                 110

Pro Ser Leu Glu Asp Glu Ala Ala Gly His Val Thr Gln Ala Arg Met
        115                 120                 125

Val Ser Lys Ser Lys Asp Gly Thr Gly Ser Asp Asp Lys Lys Ala Lys
130                 135                 140

Gly Ala Asp Gly Lys Thr Lys Ile Ala Thr Pro Arg Gly Ala Ala Pro
145                 150                 155                 160

Pro Gly Gln Lys Gly Gln Ala Asn Ala Thr Arg Ile Pro Ala Lys Thr
                165                 170                 175

Pro Pro Ala Pro Lys Thr Pro Pro Ser Ser Gly Glu Pro Pro Lys Ser
            180                 185                 190

Gly Asp Arg Ser Gly Tyr Ser Ser Pro Gly Ser Pro Gly Thr Pro Gly
        195                 200                 205

Ser Arg Ser Arg Thr Pro Ser Leu Pro Thr Pro Pro Thr Arg Glu Pro
210                 215                 220

Lys Lys Val Ala Val Val Arg Thr Pro Pro Lys Ser Pro Ser Ser Ala
225                 230                 235                 240

Lys Ser Arg Leu Gln Thr Ala Pro Val Pro Met Pro Asp Leu Lys Asn
                245                 250                 255

Val Lys Ser Lys Ile Gly Ser Thr Glu Asn Leu Lys His Gln Pro Gly
            260                 265                 270
```

```
Gly Gly Lys Val Gln Ile Ile Asn Lys Lys Leu Asp Leu Ser Asn Val
            275                 280                 285

Gln Ser Lys Cys Gly Ser Lys Asp Asn Ile Lys His Val Pro Gly Gly
        290                 295                 300

Gly Ser Val Gln Ile Val Tyr Lys Pro Val Asp Leu Ser Lys Val Thr
305                 310                 315                 320

Ser Lys Cys Gly Ser Leu Gly Asn Ile His His Lys Pro Gly Gly Gly
                325                 330                 335

Gln Val Glu Val Lys Ser Glu Lys Leu Asp Phe Lys Asp Arg Val Gln
            340                 345                 350

Ser Lys Ile Gly Ser Leu Asp Asn Ile Thr His Val Pro Gly Gly Gly
        355                 360                 365

Asn Lys Lys Ile Glu Thr His Lys Leu Thr Phe Arg Glu Asn Ala Lys
370                 375                 380

Ala Lys Thr Asp His Gly Ala Glu Ile Val Tyr Lys Ser Pro Val Val
385                 390                 395                 400

Ser Gly Asp Thr Ser Pro Arg His Leu Ser Asn Val Ser Ser Thr Gly
                405                 410                 415

Ser Ile Asp Met Val Asp Ser Pro Gln Leu Ala Thr Leu Ala Asp Glu
            420                 425                 430

Val Ser Ala Ser Leu Ala Lys Gln Gly Leu
            435                 440

<210> SEQ ID NO 54
<211> LENGTH: 448
<212> TYPE: PRT
<213> ORGANISM: Artificial Sequence
<220> FEATURE:
<223> OTHER INFORMATION: humanized

<400> SEQUENCE: 54

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Asp Ile Ala Trp Ile Arg Gln Pro Pro Gly Lys Gly Leu Glu Trp Met
        35                  40                  45

Gly Thr Ile Trp Thr Asp Gly Ser Thr Asn Tyr Asn Ala Ala Val Gln
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

-continued

```
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 55
<211> LENGTH: 448
<212> TYPE: PRT
<213> ORGANISM: Artificial Sequence
<220> FEATURE:
<223> OTHER INFORMATION: humanized

<400> SEQUENCE: 55

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Asp Ile Ala Trp Ile Arg Gln Pro Pro Gly Lys Gly Leu Glu Trp Met
        35                  40                  45

Gly Thr Ile Trp Thr Asp Gly Ser Thr Asn Tyr Asn Thr Ala Val Gln
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Arg Leu Tyr Tyr Gly Ala Phe Asp Tyr Trp Gly Gln Gly Thr
            100                 105                 110
```

Met Val Thr Val Ser Ser Ala Ser Thr Lys Gly Pro Ser Val Phe Pro
115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 56
<211> LENGTH: 1344
<212> TYPE: DNA
<213> ORGANISM: Artificial Sequence
<220> FEATURE:
<223> OTHER INFORMATION: humanized

<400> SEQUENCE: 56
gaggtgcagc tgcaggaatc cggtcccggc ctcgtgaagc cttcagaaac cctgtcgctc     60
acatgcactg tgtccgggtt ctccctgacc tctaacgaca tcgcctggat tcggcagccg    120
ccaggaaagg gactggagtg gatgggcacc atttggaccg acgggtcaac caactacaat    180

| | |
|---|---|
| gccgcggtgc aatccagagt gaccatcagc gtggacacgt ccaagaacca gttctcgctg | 240 |
| aaattgagct ccgtgactgc cgctgatact gccgtgtatt actgtgcccg gcaccgcctt | 300 |
| tactacggcg catttgacta ctggggacag ggaaccatgg tcactgtctc gagtgcctcc | 360 |
| accaagggcc cctccgtgtt cccgctcgct ccatcatcga agtctaccag cggaggcact | 420 |
| gcggctctcg gttgcctcgt gaaggactac ttcccggagc cggtgaccgt gtcgtggaac | 480 |
| agcggagccc tgaccagcgg ggtgcacacc tttccggccg tcttgcagtc aagcggcctt | 540 |
| tactccctgt catcagtggt gactgtcccg tccagctcat gggaaccca aacctacatc | 600 |
| tgcaatgtga atcacaaacc tagcaacacc aaggttgaca agaaagtcga gcccaaatcg | 660 |
| tgtgacaaga ctcacacttg tccgccgtgc ccggcacccg aactgctggg aggtcccagc | 720 |
| gtctttctgt tccctccaaa gccgaaagac acgctgatga tctcccgcac cccggaggtc | 780 |
| acttgcgtgg tcgtggacgt gtcacatgag gacccagagg tgaagttcaa ttggtacgtg | 840 |
| gatggcgtcg aagtccacaa tgccaaaact aagcccagag aagaacagta caattcgacc | 900 |
| taccgcgtcg tgtccgtgct cacggtgttg catcaggatt ggctgaacgg gaaggaatac | 960 |
| aagtgcaaag tgtccaacaa ggcgctgccg gcaccgatcg agaaaactat ctccaaagcg | 1020 |
| aagggacagc ctagggaacc tcaagtctac acgctgccaa catcacggga tgaactgact | 1080 |
| aagaatcaag tctcactgac ttgtctggtg aagggggtttt accctagcga cattgccgtg | 1140 |
| gagtgggaat ccaacggcca gccagagaac aactacaaga ctacccctcc agtgctcgac | 1200 |
| tcggatggat cgttcttcct ttactcgaag ctcaccgtgg ataagtcccg gtggcagcag | 1260 |
| ggaaacgtgt tctcctgctc ggtgatgcat gaagccctcc ataaccacta tacccaaaag | 1320 |
| tcgctgtccc tgtcgccggg aaag | 1344 |

<210> SEQ ID NO 57
<211> LENGTH: 1344
<212> TYPE: DNA
<213> ORGANISM: Artificial Sequence
<220> FEATURE:
<223> OTHER INFORMATION: humanized

<400> SEQUENCE: 57

| | |
|---|---|
| gaggtgcaac tgcaggaatc cggtcccggc ctcgtgaagc cttcagaaac cctgtcgctc | 60 |
| acatgcactg tgtccgggtt ctccctgacc tctaacgaca tcgcctggat tcggcagccg | 120 |
| ccaggaaagg gactggagtg gatgggcacc atttggaccg acgggtcaac caactacaat | 180 |
| accgcggtgc aatccagagt gaccatcagc gtggacacgt ccaagaacca gttctcgctg | 240 |
| aaattgagct ccgtgactgc cgctgatact gccgtgtatt actgtgcccg gcaccgcctt | 300 |
| tactacggcg catttgacta ctggggacag ggaaccatgg tcactgtctc gagtgcctcc | 360 |
| accaagggcc cctccgtgtt cccgctcgct ccatcatcga agtctaccag cggaggcact | 420 |
| gcggctctcg gttgcctcgt gaaggactac ttcccggagc cggtgaccgt gtcgtggaac | 480 |
| agcggagccc tgaccagcgg ggtgcacacc tttccggccg tcttgcagtc aagcggcctt | 540 |
| tactccctgt catcagtggt gactgtcccg tccagctcat gggaaccca aacctacatc | 600 |
| tgcaatgtga atcacaaacc tagcaacacc aaggttgaca agaaagtcga gcccaaatcg | 660 |
| tgtgacaaga ctcacacttg tccgccgtgc ccggcacccg aactgctggg aggtcccagc | 720 |
| gtctttctgt tccctccaaa gccgaaagac acgctgatga tctcccgcac cccggaggtc | 780 |
| acttgcgtgg tcgtggacgt gtcacatgag gacccagagg tgaagttcaa ttggtacgtg | 840 |
| gatggcgtcg aagtccacaa tgccaaaact aagcccagag aagaacagta caattcgacc | 900 |

```
taccgcgtcg tgtccgtgct cacggtgttg catcaggatt ggctgaacgg gaaggaatac    960
aagtgcaaag tgtccaacaa ggcgctgccg gcaccgatcg agaaaactat ctccaaagcg   1020
aagggacagc ctagggaacc tcaagtctac acgctgccac catcacggga tgaactgact   1080
aagaatcaag tctcactgac ttgtctggtg aaggggtttt accctagcga cattgccgtg   1140
gagtgggaat ccaacggcca gccagagaac aactacaaga ctacccctcc agtgctcgac   1200
tcggatggat cgttcttcct ttactcgaag ctcaccgtgg ataagtcccg gtggcagcag   1260
ggaaacgtgt tctcctgctc ggtgatgcat gaagccctcc ataaccacta tacccaaaag   1320
tcgctgtccc tgtcgccggg aaag                                         1344
```